US010072296B2

(12) United States Patent
Mougeot et al.

(10) Patent No.: US 10,072,296 B2
(45) Date of Patent: Sep. 11, 2018

(54) COMPOSITIONS AND METHODS FOR SJÖGREN'S SYNDROME

(71) Applicant: The Charlotte Mecklenburg Hospital Authority, Charlotte, NC (US)

(72) Inventors: Jean-Luc C. Mougeot, Charlotte, NC (US); Farah K. B. Mougeot, Charlotte, NC (US); Nirav Shah, Fort Mill, SC (US)

(73) Assignee: The Charlotte Mecklenburg Hospital Authority, Charlotte, NC (US)

( * ) Notice: Subject to any disclaimer, the term of this patent is extended or adjusted under 35 U.S.C. 154(b) by 0 days.

(21) Appl. No.: 15/709,152

(22) Filed: Sep. 19, 2017

(65) Prior Publication Data

US 2018/0080082 A1 Mar. 22, 2018

Related U.S. Application Data

(60) Provisional application No. 62/396,770, filed on Sep. 19, 2016.

(51) Int. Cl.
*C12Q 1/68* (2018.01)
*C12Q 1/6883* (2018.01)
*G01N 33/68* (2006.01)

(52) U.S. Cl.
CPC ....... *C12Q 1/6883* (2013.01); *G01N 33/6893* (2013.01); *C12Q 2600/118* (2013.01); *C12Q 2600/154* (2013.01); *C12Q 2600/158* (2013.01); *G01N 2333/47* (2013.01); *G01N 2800/101* (2013.01); *G01N 2800/52* (2013.01)

(58) Field of Classification Search
None
See application file for complete search history.

(56) References Cited

U.S. PATENT DOCUMENTS

2005/0148643 A1* 7/2005 Rui .................. A61K 31/00 514/366
2015/0273083 A1* 10/2015 Chiorini ............. G01N 33/6893 424/9.1

OTHER PUBLICATIONS

Miceli-Richard et al "Overlap between differentially methylated DNA regions in blood B lymphocytes and genetic at-risk loci in primary Sjögren's syndrome" (Ann Rheum Dis 2016; vol. 75: 933-940; published online Jul. 13, 2015). (Year: 2015).*
Perez et al in "Gene expression and chromosomal location for susceptibility to Sjögren's syndrome" (Journal of Autoimmunity 2009, vol. 33, pp. 99-108). (Year: 2009).*
Altorok et al in "Genome-wide DNA methylation patterns in naïve CD4+ T cells from patients with primary Sjogren's syndrome." (Arthritis Rheum 2014; vol. 66, pp. 731-739). (Year: 2014).*
Song et al in "Meta-analysis of differentially expressed genes in primary by using microarray" (Human Immunology, 2014 vol. 75, pp. 98-104, available online Sep. 30, 2013), (Year: 2013).*
Alevizos, Ilias "Clinical Investigations of Sjogren's Syndrome" *National Institute of Dental & Craniofacial Research (NIDCR)* (2014) (Abstract only).
Arismendi et al. "Identification of NF-kB and PLCL2 as new susceptibility genes and highlights on a potential role of IRF8 through interferon signature modulation in systemic sclerosis" *Arthritis Research & Therapy* 17(71):1-11 (2015).
Crampton et al. "Integration of the β-Catenin-Dependent Wnt Pathway with Integrin Signaling through the Adaptor Molecule Grb2" *PLoS One* 4(11):e7841 (2009).
De Bin, R. "Boosting in Cox regression: a comparison between the likelihood-based and the model-based approaches with focus on the R-packages CoxBoost and mboosf" *Computational Statistics* 31(2):513-531 (2016) (Abstract only).
Delaleu et al. "Sjögren's syndrome: studying the disease in mice" *Arthritis Research & Therapy* 13(217):1-16 (2011).
Furlan et al. "Ets-1 triggers and orchestrates the malignant phenotype of mammary cancer cells within their matrix environment" *Journal of Cellular Physiology* 215(3):782-793 (Abstract only).
Gade et al. "Graph based function of miRNA and mRNA expression data improves clinical outcome prediction in prostate cancer" *BMC Bioinformatics* 12(488):1-10 (2011).
Ghosh et al. "ETS-1 Protein Regulates Vascular Endothelial Growth Factor-induced Matrix Metalloproteinase-9 and Matrix Metalloproteinase-13 Expression in Human Ovarian Carcinoma Cell Line SKOV-3" *The Journal of Biological Chemistry* 287(18):15001-15015 (2012).
Jelier et al. "Literature-based concept profiles for gene annotation: the issue of weighting" *International Journal of Medical Informatics* 77(5):354-362 (2008) (Abstract only).
Jessie et al. "Protein Precipitation Method for Salivary Proteins and Rehydration Buffer for Two-Dimensional Electrophoresis" *Biotechnology* 7(4):686-693 (2008).
Lessard et al. "Variants at multiple loci implicated in both innate and adaptive immune responses are associated with Sjögren's syndrome" *Nature Genetics* 45(11):1-26 (2013).
Nagarajan et al. "Ets1 Induces Dysplastic Changes When Expressed in Terminally-Differentiating Squamous Epidermal Cells" *PLoS One* 4(1):e4179 (2009).
Perez et al. "Increased Acinar Damage of Salivary Glands of Patients With Sjögren's Syndrome is Paralleled by Simultaneous Imbalance of Matrix Metalloproteinase 3/Tissue Inhibitor of Metalloproteinases 1 and Matrix Metalloproteinase 9/Tissue Inhibitor of Metalloproteinases 1 Ratios" *Arthritis & Rheumatism* 52(9):2751-2760 (2005).
Shah et al. "Biosemantics guided gene expression profiling of Sjögren's syndrome: a comparative analysis with systemic lupus erythematosus and rheumatoid arthritis" *Arthritis Research & Therapy* 19(192):1-14 (2017).
Song et al. "Meta-analysis of differentially expressed genes in primary Sjögren's syndrome by using microarray" *Human Immunology* 75(1):98-104 (2014) (Abstract only).
Toro-Dominguez et al. "Shared signatures between rheumatoid arthritis, systemic lupus erythematosus and Sjögren's syndrome uncovered through gene expression meta-analysis" *Arthritis Research & Therapy* 16(6):1-8 (2014).

(Continued)

*Primary Examiner* — Catherine S Hibbert
(74) *Attorney, Agent, or Firm* — Myers Bigel, P.A.

(57) ABSTRACT

The present invention provides methods and compositions involving epigenetic and gene expression signatures and their association with Sjögren's syndrome.

4 Claims, 10 Drawing Sheets

(56) References Cited

OTHER PUBLICATIONS

Wang et al. "Knockdown of Lymphoid Enhancer factor 1 Inhibits Colon Cancer Progression In Vitro and In Vivo" *PLoS One* 8(10):e76596 (2013).

Wei et al. "Novel Candidate Biomarkers of Sjögren's Syndrome Pathogenesis" *Poster Presented at the Carolina's HealthCare System Summer Scholars Program*, May 30, 2017-Aug. 4, 2017 (1 page) (presented on Aug. 3, 2017).

* cited by examiner

FIG. 7

| Genes | NGR | TNGR | NG | TNG | Hyp | Hyp* | Annotations |
|---|---|---|---|---|---|---|---|
| 15 genes | 181 | 34208 | 15 | 76 | 8.47587e-20 | 5.95006e-17 | GO:0019221: cytokine-mediated signaling pathway (BP) |
| 14 genes | 382 | 34208 | 14 | 76 | 1.35832e-13 | 4.76772e-11 | GO:0006955: immune response (BP) |
| 8 genes | 75 | 34208 | 8 | 76 | 6.08085e-12 | 1.42292e-09 | GO:0060337: type I interferon-mediated signaling pathway (BP) |
| 11 genes | 259 | 34208 | 11 | 76 | 1.40564e-11 | 2.46689e-09 | GO:0006954: inflammatory response (BP) |
| 9 genes | 171 | 34208 | 9 | 76 | 1.68561e-10 | 2.36659e-08 | GO:0007166: cell surface receptor signaling pathway (BP) |
| 8 genes | 126 | 34208 | 8 | 76 | 4.13608e-10 | 4.83921e-08 | GO:0006935: chemotaxis (BP) |
| 8 genes | 136 | 34208 | 8 | 76 | 7.61429e-10 | 7.63604e-08 | GO:0032496: response to lipopolysaccharide (BP) |
| 5 genes | 51 | 34208 | 5 | 76 | 1.02701e-07 | 9.01203e-06 | GO:0071260: cellular response to mechanical stimulus (BP) |
| 9 genes | 361 | 34208 | 9 | 76 | 1.12401e-07 | 8.76728e-06 | GO:0008284: positive regulation of cell proliferation (BP) |
| 5 genes | 54 | 34208 | 5 | 76 | 1.3755e-07 | 9.658e-06 | GO:0019882: antigen processing and presentation (BP) |
| 3 genes | 7 | 34208 | 3 | 76 | 3.66477e-07 | 2.33879e-05 | GO:0002544: chronic inflammatory response (BP) |
| 8 genes | 309 | 34208 | 8 | 76 | 4.48142e-07 | 2.62163e-05 | GO:0045087: innate immune response (BP) |
| 6 genes | 144 | 34208 | 6 | 76 | 8.59636e-07 | 4.64203e-05 | GO:0009615: response to virus (BP) |
| 5 genes | 82 | 34208 | 5 | 76 | 1.13067e-06 | 5.66952e-05 | GO:0060333: interferon-gamma-mediated signaling pathway (BP) |
| 5 genes | 89 | 34208 | 5 | 76 | 1.69935e-06 | 7.95296e-05 | GO:0032355: response to estradiol stimulus (BP) |
| 13 genes | 1176 | 34208 | 13 | 76 | 1.79419e-06 | 7.872e-05 | GO:0007165: signal transduction (BP) |

FIG. 8

| Id | Items | Disease | Support | List size | Hyp | Hyp_c | Genes |
|---|---|---|---|---|---|---|---|
| 28 | Kegg:05162 | Measles | 12 | 76 | 1.36E-16 | 1.26E-14 | STAT1, STAT2, OAS2, MX1, FAS, IFNG, DDX58, IL2RB, OAS3, IFIH1, TACR1, TLR2 |
| 1 | Kegg:05160 | Hepatitis C | 7 | 76 | 2.00E-08 | 4.61E-07 | STAT1, STAT2, OAS2, IFIT1, DDX58, OAS1, LDLR |
| 20 | Kegg:05145 | Toxoplasmosis | 6 | 76 | 3.49E-07 | 5.21E-06 | STAT1, MAP2K3, IFNG, LY96, ITGB1 |
| 74 | Kegg:05142 | Chagas disease (American trypanosomiasis) | 5 | 76 | 3.33E-06 | 3.41E-05 | FAS, IFNG, CALR, CD247, CFLAR |
| 38 | Kegg:05152 | Tuberculosis | 3 | 76 | 0.00671216 | 0.0205839 | STAT1, CD74, IFNG |
| 70 | Kegg:05140 | Leishmaniasis | 3 | 76 | 0.000436047 | 0.00026744 | STAT1, IFNG, ITGB1 |
| 84 | Kegg:05146 | Amoebiasis | 3 | 76 | 0.001546506 | 0.0071073 | IFNG, CD1D, COL5A1 |
| 89 | Kegg:05332 | Graft-versus-host disease | 3 | 76 | 4.19E-05 | 0.0003427 | KLRC1, FAS, IFNG |
| 39 | Kegg:05320 | Autoimmune thyroid disease | 2 | 76 | 0.0045332 | 0.0149943 | FAS, TSHR |
| 41 | Kegg:05143 | African trypanosomiasis | 2 | 76 | 0.0024597 | 0.0098388 | FAS, IFNG |
| 51 | Kegg:05130 | Pathogenic Escherichia coli infection | 2 | 76 | 0.00644B6 | 0.0205211 | LY96, ITGB1 |
| 62 | Kegg:04940 | Type 1 diabetes mellitus | 2 | 76 | 0.0028 | 0.0100038 | FAS, IFNG |
| 67 | Kegg:05323 | Rheumatoid arthritis | 2 | 76 | 0.0150972 | 0.0408512 | CXCL5, IFNG |
| 76 | Kegg:05212 | Pancreatic cancer | 2 | 76 | 0.01088 | 0.0306755 | STAT1, RAD51 | ically used gene expression data containing both male and
female patients. There is a mounting body of evidence
suggesting that higher susceptibility to SS in females could
be associated with the aberrant expression of specific genes
located on the X chromosome in conjunction with X chromosome linked epigenetic events possibly involving the
activation of endogenous retroviruses.

COMPOSITIONS AND METHODS FOR SJÖGREN'S SYNDROME

STATEMENT OF PRIORITY

This application claims the benefit, under 35 U.S.C. § 119(e), of U.S. Provisional Application Ser. No. 62/396,770, filed Sep. 19, 2016, the entire contents of which are incorporated by reference herein.

FIELD OF THE INVENTION

The present invention relates to compositions and methods employing epigenetic and gene expression signatures to predict risk and monitor the development and response to treatment of exocrine and systemic complications of Sjögren's syndrome.

BACKGROUND OF THE INVENTION

Sjögren's syndrome (SS) is a chronic autoimmune disease affecting about 0.5-3% of the given population. SS is primarily characterized by dysfunctional exocrine glands due to lymphocytic infiltration resulting in excessive dry mouth (xerostomia) and dry eyes (keroconjunctivitis Sicca). Autoimmune diseases often share common clinical and pathological features with each other such as an active innate immune response, chronic inflammation, development of specific autoantibodies, systemic dysfunction of multiple organs, etc. SS is most closely associated with the two autoimmune disorders, systemic lupus erythematosus (SLE) and rheumatoid arthritis (RA). Auto-immune diseases are usually more common in females than males. In particular, SS and SLE overwhelmingly affect females to males, with a 9:1 ratio. RA also affects more females than males but less drastically (2-3:1).

Despite overlapping pathophysiological markers shared among SS, SLE and RA patients, the exact mechanism responsible for the onset and progression of these diseases is not fully understood. In recent years, in the search for biomarkers unique to SS or common to SS, SLE and RA several meta-analyses studies have attempted to compare multiple SS gene expression datasets with each other or in conjunction with SLE and RA. In these studies, expression analyses were conducted using peripheral blood mononuclear cells (PBMCs) or biopsies of tissues affected in each disease, i.e., salivary glands in SS, and synovial biopsies in SLE and RA. These meta-analyses studies mostly focused on the identification of genes demonstrating the largest fold changes in mRNA expression in SS patient samples compared to controls. However, large fold changes in transcriptional expression of certain genes observed in these studies could be irrelevant to disease etiology as these may be characteristic of the symptomatology in advanced stages of the disease, rather than disease-onset or pre-symptomatic stages. For example, high levels of type I interferon related genes (e.g., IFN-alpha) are expressed in PBMCs and salivary gland biopsies in SS. However, in salivary glands, increased type I IFN expression could be largely attributed to the frequently observed lymphocytic infiltration and not directly related to etiological mechanisms that would initiate in the salivary glands. Indeed, recently identified potential disease susceptibility genes and infection by viruses with high tropism for exocrine glands are suspected to play an important role in the etiology of SS ahead of the development of systemic autoimmune responses.

Moreover, while SS predominantly occurs in females and an X-chromosome dosage effect has been identified, previous meta-analysis studies comparing SS, SLE, and RA mostly used gene expression data containing both male and female patients. There is a mounting body of evidence suggesting that higher susceptibility to SS in females could be associated with the aberrant expression of specific genes located on the X chromosome in conjunction with X chromosome linked epigenetic events possibly involving the activation of endogenous retroviruses.

In addition, the use of concept profile analysis (CPA) has emerged as a promising approach for biomedical discoveries especially when the amount of data is limited, inadequate or limited categories of controls are used, or there is a lack of general understanding in disease mechanisms. Similar to gene ontology analysis approaches, in CPA each biological entity (e.g., genes, diseases, symptoms, pathways, chemicals, drugs, tissues, toxins . . . etc.) can represent a concept of a concept list (or profile) of another concept and be ranked in order of relevance within the list defining a hierarchy, based on literature mining.

The present invention overcomes previous shortcomings in the art by providing methods and compositions employing epigenetic and gene expression signatures as biomarkers for prediction of risk, progression and response to treatment for exocrine and systemic complications associated with Sjögren's syndrome.

SUMMARY OF THE INVENTION

In one aspect, the present invention provides a method of identifying a subject as having Sjögren's syndrome (SS), or as having an increased risk of developing SS, comprising: a) measuring a level of messenger RNA (mRNA) transcripts for the genes ETS1, LEF1, TIMP1, CHEK1, CXCL10, MMP9 and TLR7 (or encoded proteins) in a sample from the subject; b) determining the DNA methylation status of the genes: ETS1, LEF1, MMP-9, CHEK1, CXCL10, TIMP1 and TLR7 in a sample from the subject; c) determining the levels of long interspersed nuclear elements (LINEs) and the protein encoded by LINE1 (ORF1(p40)) in a sample from the subject; and d) comparing the mRNA transcript levels of (a), the DNA methylation status of (b) and the levels of LINEs and the protein encoded by LINE1 of (c) with a level of messenger RNA (mRNA) transcripts (or encoded proteins) for the genes ETS1, LEF1, TIMP1, CHEK1, CXCL10, MMP9 and TLR7 correlated with SS, DNA methylation status of the genes ETS1, LEF1, TIMP1, CHEK1, CXCL10, MMP9 and TLR7 correlated with SS and levels of LINEs and the protein encoded by LINE1 correlated with SS, wherein mRNA transcript levels, DNA methylation status and levels of LINEs and the protein encoded by LINE1 of the subject having similarity with mRNA transcript (or encoded protein) levels, DNA methylation status and levels of LINEs and the protein encoded by LINE1 correlated with SS identifies the subject as having SS or as having an increased risk of developing SS.

An additional aspect of the invention provides a method of identifying a subject having an increased likelihood of a poor prognosis related to SS, comprising: a) measuring a level of messenger RNA (mRNA) transcripts (or encoded proteins) for the genes ETS1, LEF1, TIMP1, CHEK1, CXCL10, MMP9 and TLR7 in a sample from the subject; b) determining the DNA methylation status of the genes ETS1, LEF1, MMP-9, CHEK1, CXCL10, TIMP1 and TLR7 in a sample from the subject; c) determining the levels of long interspersed nuclear elements (LINEs) and the protein encoded by LINE1 in a sample from the subject; and d) comparing the level of mRNA transcripts (or encoded proteins) of (a), the DNA methylation status of (b) and the levels of LINEs and protein encoded by LINE1 of (c) correlated with mRNA transcript (or encoded protein) levels of the genes ETS1, LEF1, TIMP1, CHEK1, CXCL10, MMP9 and TLR7 correlated with severe or advanced SS, the DNA methylation status of the genes ETS1, LEF1, TIMP1, CHEK1, CXCL10, MMP9 and TLR7 correlated with severe or advanced SS, and the levels of LINEs and the protein encoded by LINE1 correlated with severe or advanced SS, wherein mRNA transcript (or encoded protein) levels, DNA methylation status and levels of LINEs and the protein encoded by LINEs of the subject having similarity with the mRNA transcript levels, DNA methylation status and levels of LINEs and the protein encoded by LINE1 correlated with severe or advanced SS identifies the subject as having an increased likelihood of a poor prognosis related to SS.

Another aspect of this invention is a method of monitoring a subject's response to treatment for SS, comprising: a) measuring a level of messenger RNA (mRNA) transcripts (or encoded proteins) for the genes ETS1, LEF1, TIMP1, CHEK1, CXCL10, MMP9 and TLR7 in a sample from the subject prior to treatment of the subject for SS; b) determining the DNA methylation status of the genes ETS1, LEF1, MMP-9, CHEK1, CXCL10, TIMP1 and TLR7 in a sample from the subject prior to treatment of the subject for SS; c) determining levels of long interspersed nuclear elements (LINEs) and protein encoded by LINE1 in a sample from the subject prior to treatment of the subject for SS; d) initiating treatment of the subject for SS; e) measuring a levels of messenger RNA (mRNA) transcripts (or encoded proteins) for the genes ETS1, LEF1, TIMP1, CHEK1, CXCL10, MMP9 and TLR7 in a sample from the subject at one or more time points after initiation of treatment of the subject for SS; f) determining the DNA methylation status of the genes ETS1, LEF1, MMP-9, CHEK1, CXCL10, TIMP1 and TLR7 in a sample from the subject at one or more time points after initiation of treatment of the subject for SS; g) determining levels of long interspersed nuclear elements (LINEs) and protein encoded by LINE1 in a sample from the subject at one or more time points after initiation of treatment of the subject for SS; and h) comparing the mRNA transcript (or encoded protein) levels of (a) and (e), the DNA methylation status of (b) and (f) and the levels of LINEs and the protein encoded by LINE1 of (c) and (g), wherein mRNA transcript levels, DNA methylation status and levels of LINEs and the protein encoded by LINE1 determined after initiation of treatment for SS having less similarity with the mRNA transcript levels, DNA methylation status and levels of LINES and the protein encoded by LINE1 correlated with SS identifies the subject as having a positive response to the treatment and wherein mRNA transcript levels, DNA methylation status and levels of LINEs and the protein encoded by LINE1 determined after initiation of treatment for SS having more similarity with mRNA transcript levels, DNA methylation status and levels of LINES and the protein encoded by LINE1 correlated with SS identifies the subject as having a negative response to treatment.

In a further aspect, the present invention provides a method of monitoring a subject's response to treatment for severe or advanced SS, comprising: a) measuring a level of messenger RNA (mRNA) transcripts (or encoded protein) for the genes ETS1, LEF1, TIMP1, CHEK1, CXCL10, MMP9 and TLR7 in a sample from the subject prior to treatment of the subject for severe or advanced SS; b) determining the DNA methylation status of the genes ETS1, LEF1, MMP-9, CHEK1, CXCL10, TIMP1 and TLR7 in a sample from the subject prior to treatment of the subject for severe or advanced SS; c) determining levels of long interspersed nuclear elements (LINEs) and protein encoded by LINE1 in a sample from the subject prior to treatment of the subject for severe or advanced SS; d) initiating treatment of the subject for severe or advanced SS; e) measuring a levels of messenger RNA (mRNA) transcripts (or encoded protein) for the genes ETS1, LEF1, TIMP1, CHEK1, CXCL10, MMP9 and TLR7 in a sample from the subject at one or more time points after initiation of treatment of the subject for severe or advanced SS; f) determining the DNA methylation status of the genes ETS1, LEF1, MMP-9, CHEK1, CXCL10, TIMP1 and TLR7 in a sample from the subject at one or more time points after initiation of treatment of the subject for severe or advanced SS; g) determining levels of long interspersed nuclear elements (LINEs) and protein encoded by LINE1 in a sample from the subject at one or more time points after initiation of treatment of the subject for severe or advanced SS; and h) comparing the mRNA transcript levels of (a) and (e), the DNA methylation status of (b) and (f) and the levels of LINEs and the protein encoded by LINE1 of (c) and (g), wherein mRNA transcript levels, DNA methylation status and levels of LINEs and the protein encoded by LINE1 determined after initiation of treatment for severe or advanced SS having less similarity with the mRNA transcript levels, DNA methylation status and levels of LINES and the protein encoded by LINE1 correlated with severe or advanced SS identifies the subject as having a positive response to the treatment and wherein mRNA transcript levels, DNA methylation status and levels of LINEs and the protein encoded by LINE1 determined after initiation of treatment for severe or advanced SS having more similarity with mRNA transcript levels, DNA methylation status and levels of LINES and the protein encoded by LINE1 correlated with severe or advanced SS identifies the subject as having a negative response to the treatment.

Further provided herein is a method of correlating a biomarker profile of a subject with an increased risk of having or developing SS, comprising: a) identifying a subject or population of subjects having SS, b) determining the biomarker profile of the subject or of each of the subjects of the population of (a) by: 1) measuring a level of messenger RNA (mRNA) transcripts (or encoded proteins) for the genes ETS1, LEF1, TIMP1, CHEK1, CXCL10, MMP9 and TLR7 in a sample from the subject; 2) determining the DNA methylation status of the genes ETS1, LEF1, MMP-9, CHEK1, CXCL10, TIMP1 and TLR7 in a sample from the subject; and 3) determining the levels of long interspersed nuclear elements (LINEs) and the protein encoded by LINE1 in a sample from the subject; and c) correlating the presence of the biomarker profile of step (b) with SS in the subject or population of subjects.

As an additional aspect, the present invention provides a method of correlating a biomarker profile of a subject with an increased risk of having or developing severe or advanced SS, comprising: a) identifying a subject or population of subjects having severe or advanced SS, b) determining the biomarker profile of the subject or of each of the subjects of the population of (a) by: 1) measuring a level of messenger RNA (mRNA) transcripts (or encoded proteins) for the genes ETS1, LEF1, TIMP1, CHEK1, CXCL10, MMP9 and TLR7 in a sample from the subject; 2) determining the DNA methylation status of the genes ETS1, LEF1, MMP-9, CHEK1, CXCL10, TIMP1 and TLR7 in a sample from the subject; and 3) determining the levels of long interspersed nuclear elements (LINEs) and the protein encoded by LINE1 in a sample from the subject; and c) correlating the presence of the biomarker profile of step (b) with severe or advanced SS in the subject or population of subjects.

Another aspect of this invention is a method of identifying a biomarker profile correlated with SS; comprising: a) identifying a subject having SS; b) detecting in the subject the presence of a biomarker profile by: 1) measuring the levels of messenger RNA (mRNA) transcripts (or encoded proteins) for the genes ETS1, LEF1, TIMP1, CHEK1, CXCL10, MMP9 and TLR7 in a sample from the subject; 2) determining the DNA methylation status of the genes ETS1, LEF1, MMP-9, CHEK1, CXCL10, TIMP1 and TLR7 in a sample from the subject; and 3) determining levels of long interspersed nuclear elements (LINEs) and the protein encoded by LINE1 in a sample from the subject; and c) correlating the presence of the biomarker profile of step (b) with SS, thereby identifying a biomarker profile correlated with SS.

Further provided herein is a method of identifying a biomarker profile correlated with severe or advanced SS; comprising: a) identifying a subject having severe or advanced SS; b) detecting in the subject the presence of a biomarker profile by: 1) measuring the levels of messenger RNA (mRNA) transcripts (or encoded proteins) for the genes ETS1, LEF1, TIMP1, CHEK1, CXCL10, MMP9 and TLR7 in a sample from the subject; 2) determining the DNA methylation status of the genes ETS1, LEF1, MMP-9, CHEK1, CXCL10, TIMP1 and TLR7 in a sample from the subject; and 3) determining levels of long interspersed nuclear elements (LINEs) and the protein encoded by LINE1 in a sample from the subject; and c) correlating the presence of biomarker profile of step (b) with severe or advanced SS, thereby identifying a biomarker profile correlated with severe or advanced SS.

The present invention is explained in greater detail in the drawings herein and the specification set forth below. The disclosures of all United States patent references cited herein are incorporated by reference herein in their entirety.

BRIEF DESCRIPTION OF THE DRAWINGS

FIG. 7. Common genes between CPA and PBMC expression data sets sorted by GO function categories using GeneCodis.

FIG. 8. Common genes between CPA and PBMC expression data sets sorted by KEGG disease pathways using GeneCodis.

DETAILED DESCRIPTION OF THE INVENTION

Figure 1:
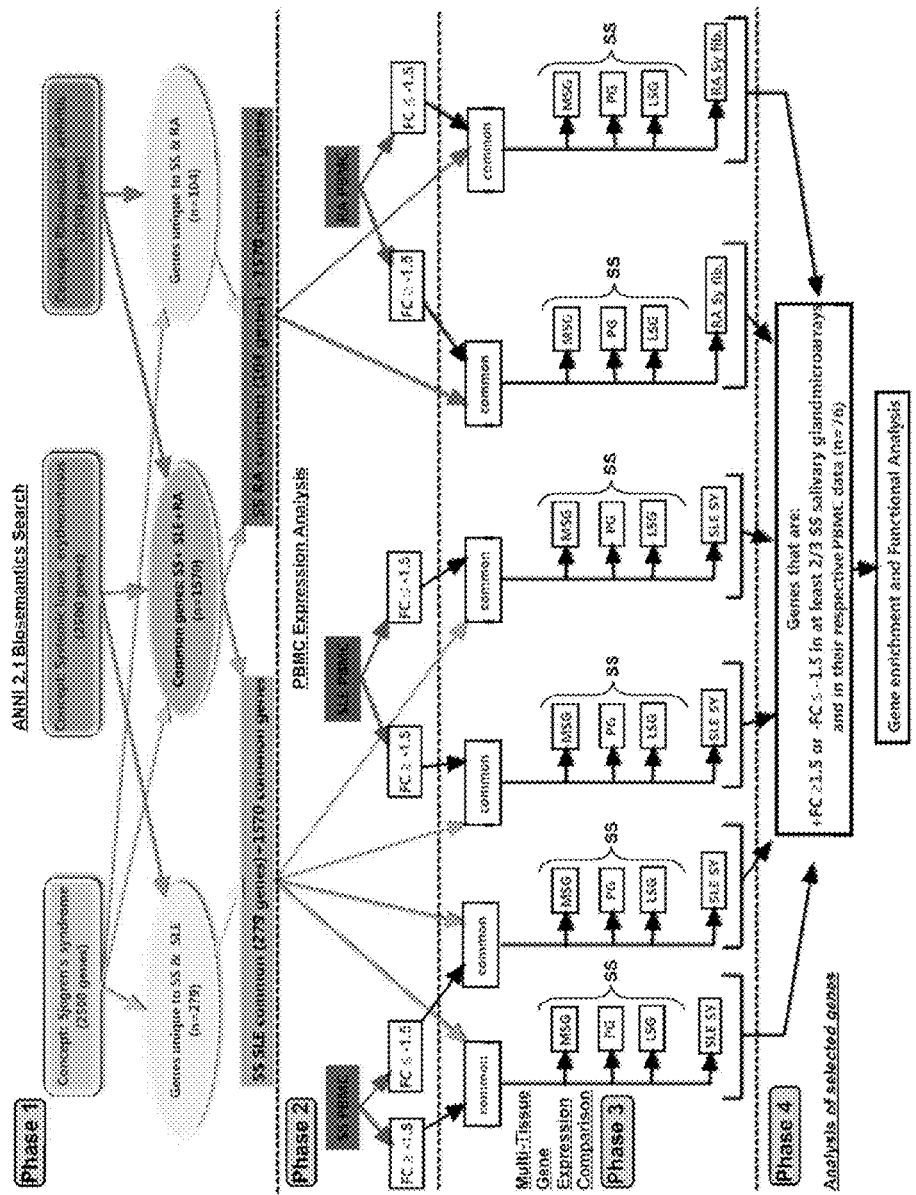
FIG. 1. Flowchart explaining the workflow of the study. (Phase 1) Concept mining of human genes associated with each concept: "Sjögren's syndrome," "systemic lupus erythematosus," "rheumatoid arthritis" and finding common genes between SS-SLE and SS-RA. (Phase 2) Comparison of common genes from Phase 1 with PBMC datasets of each disease: SS, SLE, RA. The criteria for comparison per disease were only female subjects and a gene cut-off of ≥1.5 or ≤1.5 fold change. (Phase 3) Gene expression of selected common genes from PBMC data sets and at the disease site (e.g. salivary gland for SS) is compared to identify differentially regulated genes. (Phase 4) 76 differentially regulated genes were identified from SS patient salivary gland datasets and used for the gene enrichment and functional analysis.

For the purposes of promoting an understanding of the principles of the present invention, reference will now be made to particular embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the invention relates.

The present invention is based on the unexpected discovery that a subject's epigenetic and gene expression signature (e.g., biomarker profile) can be used to diagnose and/or predict the subject's risk of having or developing Sjogren's syndrome (SS) and/or exocrine and systemic complications associated SS, as well as, e.g., to monitor and guide treatment and/or establish a prognosis, among other uses. Accordingly, in one embodiment, the present invention provides a method of identifying a subject as having Sjögren's syndrome (SS), or as having an increased risk of developing SS, comprising: a) measuring a level of messenger RNA (mRNA) transcripts (or encoded proteins) for the genes ETS1, LEF1, TIMP1, CHEK1, CXCL10, MMP9 and TLR7 in a sample from the subject; b) determining the DNA methylation status of the genes: ETS1, LEF1, MMP-9, CHEK1, CXCL10, TIMP1 and TLR7 in a sample from the subject; c) determining the levels of long interspersed nuclear elements (LINEs) and the protein encoded by LINE1 (ORF1(p40)) in a sample from the subject; and d) comparing the mRNA transcript levels of (a), the DNA methylation status of (b) and the levels of LINEs and the protein encoded by LINE1 of (c) with a level of messenger RNA (mRNA) transcripts (or encoded protein) for the genes ETS1, LEF1, TIMP1, CHEK1, CXCL10, MMP9 and TLR7 correlated with SS, DNA methylation status of the genes ETS1, LEF1, TIMP1, CHEK1, CXCL10, MMP9 and TLR7 correlated with SS and levels of LINEs and the protein encoded by LINE1 correlated with SS, wherein mRNA transcript levels, DNA methylation status and levels of LINEs and the protein encoded by LINE1 of the subject having similarity with mRNA transcript levels, DNA methylation status and levels of LINEs and the protein encoded by LINE1 correlated with SS identifies the subject as having SS or as having an increased risk of developing SS.

The present invention also provides a method of identifying a subject having an increased likelihood of a poor prognosis related to SS, comprising: a) measuring a level of messenger RNA (mRNA) transcripts (or encoded proteins) for the genes ETS1, LEF1, TIMP1, CHEK1, CXCL10, MMP9 and TLR7 in a sample from the subject; b) determining the DNA methylation status of the genes ETS1, LEF1, MMP-9, CHEK1, CXCL10, TIMP1 and TLR7 in a sample from the subject; c) determining the levels of long interspersed nuclear elements (LINEs) and the protein encoded by LINE1 in a sample from the subject; and d) comparing the level of mRNA transcripts of (a), the DNA methylation status of (b) and the levels of LINEs and protein encoded by LINE1 of (c) correlated with mRNA transcript (or encoded protein) levels of the genes ETS1, LEF1, TIMP1, CHEK1, CXCL10, MMP9 and TLR7 correlated with severe or advanced SS, the DNA methylation status of the genes ETS1, LEF1, TIMP1, CHEK1, CXCL10, MMP9 and TLR7 correlated with severe or advanced SS, and the levels of LINEs and the protein encoded by LINE1 correlated with severe or advanced SS, wherein mRNA transcript levels, DNA methylation status and levels of LINEs and the protein encoded by LINEs of the subject having similarity with the mRNA transcript levels, DNA methylation status and levels of LINEs and the protein encoded by LINE1 correlated with severe or advanced SS identifies the subject as having an increased likelihood of a poor prognosis related to SS.

As an additional embodiment, the present invention provides a method of treating a subject for Sjögren's syndrome (SS), wherein the subject has a level of messenger RNA (mRNA) transcripts for the genes ETS1, LEF1, TIMP1, CHEK1, CXCL10, MMP9 and TLR7 correlated with SS, DNA methylation status of the genes ETS1, LEF1, TIMP1, CHEK1, CXCL10, MMP9 and TLR7 correlated with SS and levels of LINES and the protein encoded by LINE1.

In some embodiments, higher or increased mRNA transcript levels of the genes ETS1, LEF1, CHEK1, CXCL10, MMP9 and TLR7, and lower or decreased levels of TIMP1 can be correlated with SS, as well as severe or advanced SS. The increase or decrease is relative to levels in subjects or controls without SS.

Using a recursive descent partition analysis approach, threshold and odds ratios (to be determined from large sample size data), will be based on a fold changes range in minor salivary glands (MSG), parotid glands (PG), labial salivary glands. Current metadata on small sample sizes yielded the results shown in Table 11.

The mRNA transcript levels can be determined by using any assay that measures mRNA transcript levels in a sample. Nonlimiting examples include quantitative reverse transcriptase-polymerase chain reaction (qRT-PCR), and a custom designed microarray chip.

In some embodiments, a protein level of the gene products of the genes recited herein (as determined or measured, e.g., by ELISA, quantitative mass spectrometry and/or other immunoassay or protein assay) may be used in the methods of this invention. In addition, since TIMP1 is critical for MMP9 inactivation, a small decrease may be biologically significant. Hence, unchanged TIMP levels and an increase in other factors that increase MMP9 expression, may be detrimental to the salivary glands as well.

Similarly, the DNA methylation status of the genes ETS1, LEF1, TIMP1, CHEK1, CXCL10, MMP9 and TLR7 can be correlated with SS, as well as severe or advanced SS according to the methods described herein. Methods of determining the DNA methylation status of a gene include, as nonlimiting examples, methylation specific quantitative polymerase chain reaction (qPCR), and/or a custom methylation microarray.

In some embodiments, increased levels of LINEs and the protein encoded by LINE1 (ORF1(p40)) are also correlated with SS, as well as severe or advanced SS, with an increase or decrease determined in comparison with normal subjects or subjects that no not have SS or sever or advanced SS.

Determination of levels of LINES can be carried out by qRT-PCR, custom designed microarray, and/or F-PERT (fluorescence product-enhanced reverse transcriptase) assay, as a few nonlimiting examples. The level of protein encoded by LINE1 (ORF1(p40)) can be determined by any assay for quantitating protein in a sample, including but not limited to enzyme linked immunosorbent assay (ELISA), quantitative mass spectrometry.

As used herein, the terms "severe SS" refers to or "advanced SS" refer to advanced destruction of salivary glands, severe dry mouth or eyes, more frequent and/or extensive B-cells and T-cells infiltrations.

Prognosis of Sjögren's syndrome may include the duration, chances of complications, prospects for recovery, recovery period. Some patients experience mild symptoms of dry eyes and mouth, while others go through cycles of good health followed by severe disease (e.g., not being able to open eyes when waking up).

Also as used herein, the term "poor prognosis" refers in some embodiments to frequent repeated autoimmune attacks by lymphocytes attracted by signals mediated by biomarker differential expression possibly stimulated by transient viral/microbial infections.

Furthermore, the methods of this invention can be used to identify a subject as a fast progressor. As used herein, a "fast progressor" refers to a subject with repeated frequent lymphocyte infiltrations.

In some embodiments, the methods described herein can include the step of treating the subject for SS or for severe/advanced SS. In some embodiments, the treatment or treatments are based on individual's disease-related symptoms. For example, in some embodiments, for saliva production, para-sympathomimetic drugs such as cevimeline and pilocarpine can be administered. As another example, for certain SS associated complications, including SS-associated arthritis and arthralgia, non-steroidal anti-inflammatory drugs (NSAIDs) and/or acetaminophen, can be administered. In some embodiments for systemic symptoms, as a nonlimiting example, hydroxychloroquine, an anti-malarial drug and/or methotrexate (e.g., immune-suppressive drugs) can be administered, e.g., to suppress severe symptoms associated with Sjogren's syndrome.

The present invention additionally provides a method of monitoring a subject's response to treatment for SS, comprising: a) measuring a level of messenger RNA (mRNA) transcripts for the genes ETS1, LEF1, TIMP1, CHEK1, CXCL10, MMP9 and TLR7 (or protein product) in a sample from the subject prior to treatment of the subject for SS; b) determining the DNA methylation status of the genes ETS1, LEF1, MMP-9, CHEK1, CXCL10, TIMP1 and TLR7 in a sample from the subject prior to treatment of the subject for SS; c) determining levels of long interspersed nuclear elements (LINEs) and protein encoded by LINE1 in a sample from the subject prior to treatment of the subject for SS; d) initiating treatment of the subject for SS; e) measuring a levels of messenger RNA (mRNA) transcripts (or encoded proteins) for the genes ETS1, LEF1, TIMP1, CHEK1, CXCL10, MMP9 and TLR7 (or protein product) in a sample from the subject at one or more time points after initiation of treatment of the subject for SS; f) determining the DNA methylation status of the genes ETS1, LEF1, MMP-9, CHEK1, CXCL10, TIMP1 and TLR7 in a sample from the subject at one or more time points after initiation of treatment of the subject for SS; g) determining levels of long interspersed nuclear elements (LINEs) and protein encoded by LINE1 in a sample from the subject at one or more time points after initiation of treatment of the subject for SS; and h) comparing the mRNA transcript levels of (a) and (e), the DNA methylation status of (b) and (f) and the levels of LINEs and the protein encoded by LINE1 of (c) and (g), wherein mRNA transcript levels, DNA methylation status and levels of LINEs and the protein encoded by LINE1 determined after initiation of treatment for SS having less similarity (e.g., as compared with pre-treatment values) with the mRNA transcript levels, DNA methylation status and levels of LINES and the protein encoded by LINE1 correlated with SS identifies the subject as having a positive response to the treatment and wherein mRNA transcript levels, DNA methylation status and levels of LINEs and the protein encoded by LINE1 determined after initiation of treatment for SS having no change or more similarity (e.g., as compared with pretreatment values) with mRNA transcript levels, DNA methylation status and levels of LINES and the protein encoded by LINE1 correlated with SS identifies the subject as having no response or a negative response to treatment.

Also provided herein is a method of monitoring a subject's response to treatment for severe or advanced SS, comprising: a) measuring a level of messenger RNA (mRNA) transcripts for the genes ETS1, LEF1, TIMP1, CHEK1, CXCL10, MMP9 and TLR7 (or protein product) in a sample from the subject prior to treatment of the subject for severe or advanced SS; b) determining the DNA methylation status of the genes ETS1, LEF1, MMP-9, CHEK1, CXCL10, TIMP1 and TLR7 in a sample from the subject prior to treatment of the subject for severe or advanced SS; c) determining levels of long interspersed nuclear elements (LINEs) and protein encoded by LINE1 in a sample from the subject prior to treatment of the subject for severe or advanced SS; d) initiating treatment of the subject for severe or advanced SS; e) measuring a levels of messenger RNA (mRNA) transcripts for the genes ETS1, LEF1, TIMP1, CHEK1, CXCL10, MMP9 and TLR7 (or protein product) in a sample from the subject at one or more time points after initiation of treatment of the subject for severe or advanced SS; f) determining the DNA methylation status of the genes ETS1, LEF1, MMP-9, CHEK1, CXCL10, TIMP1 and TLR7 in a sample from the subject at one or more time points after initiation of treatment of the subject for severe or advanced SS; g) determining levels of long interspersed nuclear elements (LINEs) and protein encoded by LINE1 in a sample from the subject at one or more time points after initiation of treatment of the subject for severe or advanced SS; and h) comparing the mRNA transcript levels of (a) and (e), the DNA methylation status of (b) and (f) and the levels of LINEs and the protein encoded by LINE1 of (c) and (g), wherein mRNA transcript levels, DNA methylation status and levels of LINEs and the protein encoded by LINE1 determined after initiation of treatment for severe or advanced SS having less similarity (e.g., as compared with pre-treatment values) with the mRNA transcript levels, DNA methylation status and levels of LINES and the protein encoded by LINE1 correlated with severe or advanced SS identifies the subject as having a positive response to the treatment and wherein mRNA transcript levels, DNA methylation status and levels of LINEs and the protein encoded by LINE1 determined after initiation of treatment for severe or advanced SS having no change or more similarity (e.g., as compared with pre-treatment values) with mRNA transcript levels, DNA methylation status and levels of LINES and the protein encoded by LINE1 correlated with severe or advanced SS identifies the subject as having no response or a negative response to the treatment.

A subject identified according to the methods described herein as having a positive response to treatment can continue the treatment without modification or the subject can receive treatment modified to reduce the amount (dose) of drug and/or other therapeutic agent that is part of the treatment. Alternatively, a subject identified according to the methods described herein as having a negative response to treatment can receive a different treatment and/or receive treatment modified to increase the amount (dose) of drug and/or other therapeutic agent that is part of the treatment.

A sample for use in the methods of this invention can include, but is not limited to, saliva salivary gland tissue, synovial fluid, synovial biopsy tissue, oral mucosal cells obtained by brush biopsy, and/or any other tissue or fluid in which mRNA transcripts or encoded proteins can be measured, DNA methylation status can be determined and levels of LINEs and the protein product of LINE1 can be determined for the genes recited in the methods of this invention.

A subject of this invention can include any animal that is susceptible to having or developing SS. Nonlimiting examples of subjects of this invention include mammals, such as humans, nonhuman primates, domesticated mammals (e.g., dogs, cats, rabbits, guinea pigs, rats, mice), livestock and agricultural mammals (e.g., horses, bovine, pigs, goats). In other embodiments, a subject may additionally be an animal such as a bird or reptile. Thus, in some embodiments, a subject can be any domestic, commercially or clinically valuable animal. Subjects may be male or female and may be any age including neonate, infant, juvenile, adolescent, adult, and geriatric subjects. In particular embodiments, the subject is a human. A human subject of this invention can be of any age, gender, race or ethnic group (e.g., Caucasian (white), Asian, African, black, African American, African European, Hispanic, Mideastern, etc.).

Further provided herein is a method of correlating a biomarker profile of a subject with an increased risk of having or developing SS, comprising: a) identifying a subject or population of subjects having SS, b) determining the biomarker profile of the subject or of each of the subjects of the population of (a) by: 1) measuring a level of messenger RNA (mRNA) transcripts for the genes ETS1, LEF1, TIMP1, CHEK1, CXCL10, MMP9 and TLR7 in a sample from the subject; 2) determining the DNA methylation status of the genes ETS1, LEF1, MMP-9, CHEK1, CXCL10, TIMP1 and TLR7 in a sample from the subject; and 3) determining the levels of long interspersed nuclear elements (LINEs) and the protein encoded by LINE1 in a sample from the subject; and c) correlating the presence of the biomarker profile of step (b) with SS in the subject or population of subjects.

As another aspect of this invention, a method is provided herein of correlating a biomarker profile of a subject with an increased risk of having or developing severe or advanced SS, comprising: a) identifying a subject or population of subjects having severe or advanced SS, b) determining the biomarker profile of the subject or of each of the subjects of the population of (a) by: 1) measuring a level of messenger RNA (mRNA) transcripts for the genes ETS1, LEF1, TIMP1, CHEK1, CXCL10, MMP9 and TLR7 in a sample from the subject; 2) determining the DNA methylation status of the genes ETS1, LEF1, MMP-9, CHEK1, CXCL10, TIMP1 and TLR7 in a sample from the subject; and 3) determining the levels of long interspersed nuclear elements (LINEs) and the protein encoded by LINE1 in a sample from the subject; and c) correlating the presence of the biomarker profile of step (b) with severe or advanced SS in the subject or population of subjects.

An additional aspect of this invention is a method of identifying a biomarker profile correlated with SS; comprising: a) identifying a subject having SS; b) detecting in the subject the presence of a biomarker profile by: 1) measuring the levels of messenger RNA (mRNA) transcripts for the genes ETS1, LEF1, TIMP1, CHEK1, CXCL10, MMP9 and TLR7 in a sample from the subject; 2) determining the DNA methylation status of the genes ETS1, LEF1, MMP-9, CHEK1, CXCL10, TIMP1 and TLR7 in a sample from the subject; and 3) determining levels of long interspersed nuclear elements (LINEs) and the protein encoded by LINE1 in a sample from the subject; and c) correlating the presence of the biomarker profile of step (b) with SS, thereby identifying a biomarker profile correlated with SS.

Further provided herein is a method of identifying a biomarker profile correlated with severe or advanced SS;

comprising: a) identifying a subject having severe or advanced SS; b) detecting in the subject the presence of a biomarker profile by: 1) measuring the levels of messenger RNA (mRNA) transcripts for the genes ETS1, LEF1, TIMP1, CHEK1, CXCL10, MMP9 and TLR7 in a sample from the subject; 2) determining the DNA methylation status of the genes ETS1, LEF1, MMP-9, CHEK1, CXCL10, TIMP1 and TLR7 in a sample from the subject; and 3) determining levels of long interspersed nuclear elements (LINEs) and the protein encoded by LINE1 in a sample from the subject; and c) correlating the presence of biomarker profile of step (b) with severe or advanced SS, thereby identifying a biomarker profile correlated with severe or advanced SS.

In addition, the present invention provides a method of correlating a biomarker profile of a subject with an increased risk of having or developing SS, comprising: a) identifying a subject or population of subjects having SS, b) determining the biomarker profile of the subject or of each of the subjects of the population of (a) by: 1) measuring a level of messenger RNA (mRNA) transcripts for the genes ETS1, LEF1, TIMP1, CHEK1, CXCL10, MMP9 and TLR7 in a sample from the subject; 2) determining the DNA methylation status of the genes ETS1, LEF1, MMP-9, CHEK1, CXCL10, TIMP1 and TLR7 in a sample from the subject; and 3) determining the levels of long interspersed nuclear elements (LINEs) and the protein encoded by LINE1 in a sample from the subject; and c) correlating the presence of the biomarker profile of step (b) with SS in the subject or population of subjects.

As an additional aspect, the present invention provides a method of correlating a biomarker profile of a subject with an increased risk of having or developing severe or advanced SS, comprising: a) identifying a subject or population of subjects having severe or advanced SS, b) determining the biomarker profile of the subject or of each of the subjects of the population of (a) by: 1) measuring a level of messenger RNA (mRNA) transcripts for the genes ETS1, LEF1, TIMP1, CHEK1, CXCL10, MMP9 and TLR7 in a sample from the subject; 2) determining the DNA methylation status of the genes ETS1, LEF1, MMP-9, CHEK1, CXCL10, TIMP1 and TLR7 in a sample from the subject; and 3) determining the levels of long interspersed nuclear elements (LINEs) and the protein encoded by LINE1 in a sample from the subject; and c) correlating the presence of the biomarker profile of step (b) with severe or advanced SS in the subject or population of subjects.

An additional aspect of this invention is a method of identifying a biomarker profile correlated with SS; comprising: a) identifying a subject having SS; b) detecting in the subject the presence of a biomarker profile by: 1) measuring the levels of messenger RNA (mRNA) transcripts for the genes ETS1, LEF1, TIMP1, CHEK1, CXCL10, MMP9 and TLR7 in a sample from the subject; 2) determining the DNA methylation status of the genes ETS1, LEF1, MMP-9, CHEK1, CXCL10, TIMP1 and TLR7 in a sample from the subject; and 3) determining levels of long interspersed nuclear elements (LINEs) and the protein encoded by LINE1 in a sample from the subject; and c) correlating the presence of the biomarker profile of step (b) with SS, thereby identifying a biomarker profile correlated with SS.

Further provided herein is a method of identifying a biomarker profile correlated with severe or advanced SS; comprising: a) identifying a subject having severe or advanced SS; b) detecting in the subject the presence of a biomarker profile by: 1) measuring the levels of messenger RNA (mRNA) transcripts for the genes ETS1, LEF1, TIMP1, CHEK1, CXCL10, MMP9 and TLR7 in a sample from the subject; 2) determining the DNA methylation status of the genes ETS1, LEF1, MMP-9, CHEK1, CXCL10, TIMP1 and TLR7 in a sample from the subject; and 3) determining levels of long interspersed nuclear elements (LINEs) and the protein encoded by LINE1 in a sample from the subject; and c) correlating the presence of biomarker profile of step (b) with severe or advanced SS, thereby identifying a biomarker profile correlated with severe or advanced SS.

The biomarkers of this invention are correlated with (i.e., identified to be statistically associated with) SS or severe/advanced SS as described herein according to methods well known in the art and as disclosed in the examples provided herein for statistically correlating biomarkers with various phenotypic traits, including disease states and pathological conditions as well as determining levels of risk associated with developing a particular phenotype, such as a disease or pathological condition. In general, identifying such correlation involves conducting analyses that establish a statistically significant association and/or a statistically significant correlation between the presence of a biomarker or a combination of biomarkers and the phenotypic trait in a population of subjects and controls (e.g., matched controls). The correlation can involve one or more than one biomarker of this invention (e.g., two, three, four, five, or more) in any combination. An analysis that identifies a statistical association (e.g., a significant association) between the biomarker or combination of biomarkers and the phenotype establishes a correlation between the presence of the biomarker or combination of biomarkers in a population of subjects and the particular phenotype being analyzed. In particular embodiments, a level of risk (e.g., increased or decreased) can then be determined for a subject on the basis of such population-based analyses. Such correlation analyses can be carried out with a computer, as would be known in the art.

In further embodiments of this invention, a kit of reagents is provided for carrying out the methods of this invention. For example, a kit of this invention can comprise reagents (e.g., specific primers/probes) for measuring levels of mRNA transcripts of the genes of this invention, reagents for determining DNA methylation status of the genes of this invention, reagents for determining the levels of LINEs of this invention and reagents (e.g., antibodies) for determining the level of the protein encoded by LINE1 of this invention.

Definitions

The terms "a," "an" and "the" are used herein to refer to one or to more than one (i.e., at least one) of the grammatical object of the article. By way of example, "an element" means at least one element and can include more than one element (e.g., a multiplicity or plurality of elements).

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, "one or more" can mean one, two, three, four, five, six, seven, eight, nine, ten or more, up to any number.

Unless otherwise defined, all technical terms used herein have the same meaning as commonly understood by one of ordinary skill in the art to which this disclosure belongs.

As used herein, the term "subject" and "patient" are used interchangeably herein and refer to both human and nonhuman animals. A subject of this invention can be any subject that is susceptible to oral complications associated with radiation therapy and/or chemotherapy, and in particular embodiments, the subject of this invention is a human subject.

A "subject in need thereof" or "a subject in need of" is a subject known to have, or is suspected of having or developing oral complications associated with radiation therapy and/or chemotherapy. In particular embodiments, the subject is in need of, is scheduled for and/or is planning to undergo radiation and/or chemotherapy and/or other cancer treatment.

The term "administering" or "administered" as used herein is meant to include topical, parenteral and/or oral administration, all of which are described herein. Parenteral administration includes, without limitation, intravenous, subcutaneous and/or intramuscular administration (e.g., skeletal muscle or cardiac muscle administration). It will be appreciated that the actual method and order of administration will vary according to, inter alia, the particular preparation of compound(s) being utilized, and the particular formulation(s) of the one or more other compounds being utilized. The optimal method and order of administration of the compounds of the invention for a given set of conditions can be ascertained by those skilled in the art using conventional techniques and in view of the information set out herein.

The term "administering" or "administered" also refers, without limitation, to oral, sublingual, buccal, transnasal, transdermal, rectal, intramuscular, intravenous, intraarterial (intracoronary), intraventricular, intrathecal, and subcutaneous routes. In accordance with good clinical practice, the instant compounds can be administered at a dose that will produce effective beneficial effects without causing undue harmful or untoward side effects, i.e., the benefits associated with administration outweigh the detrimental effects.

Also as used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, and/or change in clinical parameters of the condition, disorder, disease or illness, etc., as would be well known in the art.

In some embodiments, treatments of SS are designed to reduce symptoms and not to reverse the course of the disease. In some embodiments, a gene specific re-methylation treatment strategy of the LEF1 and Ets1 gene promoters or promoters of their target genes can be employed. In another embodiment, treatment can include the use of sequence-specific DNA intercalants that could be delivered to the salivary glands within the salivary ducts of the oral cavity (e.g., via nanoparticle). For example, if the LEF1 promoter becomes demethylated due to the disease process (thereby causing its overexpression and hence destructive MMP9 overexpression), LEF1 would not be overexpressed in the presence of a sequence-specific intercalant as it would block LEF1's own transcriptional activator.

Additionally as used herein, the terms "prevent," "preventing" or "prevention" refer to any type of action that results in the absence, avoidance and/or delay of the onset and/or progression of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

An "effective amount" or "therapeutically effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, *The Science and Practice of Pharmacy* (latest edition)).

As used herein, the term "ameliorate" refers to the ability to make better, or more tolerable, a condition such as an oral complication associated with radiation therapy and/or chemotherapy. In some embodiments, the term "prevent" refers to the ability to keep a condition such as an oral complication associated with radiation therapy and/or chemotherapy from happening or existing as well as to diminish or delay onset. In some embodiments, the term "treating" refers to the caring for, or dealing with, a condition such as an oral complication associated with radiation therapy and/or chemotherapy.

Pharmaceutical compositions may be prepared as medicaments to be administered in any method suitable for the subject's condition, for example, orally, parenterally (including subcutaneous, intramuscular, and intravenous), rectally, transdermally, buccally, or nasally, or may be delivered directly to the heart by injection and/or catheter, or may be delivered to the eye as a liquid solution.

"Pharmaceutically acceptable," as used herein, means a material that is not biologically or otherwise undesirable, i.e., the material may be administered to a subject along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science*; latest edition). Exemplary pharmaceutically acceptable carriers for the compositions of this invention include, but are not limited to, sterile pyrogen-free water and sterile pyrogen-free physiological saline solution, as well as other carriers suitable for injection into and/or delivery to a subject of this invention, particularly a human subject, as would be well known in the art.

Suitable forms for oral administration include, but are not limited to, tablets, powders, compressed or coated pills, dragees, sachets, hard or gelatin capsules, sub-lingual tablets, syrups, and suspensions. Suitable forms of parenteral administration include, but are not limited to, an aqueous or non-aqueous solution or emulsion. Suitable forms for rectal administration, include, but are not limited to, suppositories with hydrophilic or hydrophobic vehicles. For topical administration, suitable forms include, but are not limited to, suitable transdermal delivery systems known in the art, such as patches, and for nasal delivery, suitable forms include, but are not limited to, aerosol and nebulized delivery systems known in the art.

A composition of the present invention (e.g., a pharmaceutical composition) may contain one or more excipients or adjuvants. Selection of excipients and/or adjuvants and the amounts to use may be readily determined by the formulation scientist upon experience and consideration of standard procedures and reference works in the field.

By "parenteral" is meant intravenous, subcutaneous or intramuscular administration. In the methods of the present invention, the composition or compound may be administered alone, simultaneously with one or more other compounds, or the composition and/or compounds may be administered sequentially, in either order. It will be appreciated that the actual method and order of administration will vary according to, inter alia, the particular preparation of compound(s) being utilized, the particular formulation(s) of the one or more other compounds being utilized, and the conditions to be treated. The optimal method and order of administration of the compounds of the disclosure for a given set of conditions can be ascertained by those skilled in the art using conventional techniques and in view of the information set out herein.

In prophylactic applications, pharmaceutical compositions or medicaments are administered to a subject susceptible to, or otherwise at risk of, occlusion or narrowing of an artery and/or its branches and/or a disease, disturbance and/or pathological condition of an artery and/or its branches in an amount sufficient to eliminate or reduce the risk, lessen the severity, or delay the onset, including biochemical, histologic and/or physiologic symptoms. In therapeutic applications, compositions or medicants are administered to a subject suspected of, or already having, occlusion or narrowing of an artery and/or its branches and/or has had or is having a disease, disturbance and/or pathological condition of an artery and/or its branches in an amount sufficient to treat, or at least partially reduce or arrest, the symptoms (biochemical, histologic and/or physiological). An amount adequate to accomplish therapeutic or prophylactic treatment is defined as an effective amount or a therapeutically or prophylactically effective dose. In either prophylactic or therapeutic regimens, compounds and/or compositions of the present invention can be administered in several doses until a desired effect has been achieved.

An effective dose or effective doses of the compositions of the present invention, for the treatment of the conditions described herein can vary depending upon many different factors, including means of administration, target site, physiological state of the subject, whether the subject is human or an animal, other medications administered, and/or whether treatment is prophylactic or therapeutic. In some embodiments, the subject is a human but nonhuman mammals including transgenic mammals can also be treated. Treatment dosages can be titrated to optimize safety and efficacy. Generally, an effective amount of the compositions of this invention will be determined by the age, weight and condition or severity of disease or disorder of the subject.

Generally, dosing (e.g., an administration) can be one or more times daily, or less frequently, such as once a day, once a week, once a month, once a year, to once in a decade, etc. and may be in conjunction with other compositions as described herein.

The dosage and frequency of administration can vary depending on whether the treatment is prophylactic or therapeutic. In prophylactic applications, a relatively low dosage can be administered at relatively infrequent intervals over a long period of time. In therapeutic applications, a relatively high dosage at relatively short intervals is sometimes appropriate until severity of the injury is reduced or terminated, and typically until the subject shows partial or complete amelioration of symptoms of injury. Thereafter, the subject can be administered a prophylactic regimen.

The terms "increased risk" and "decreased risk" as used herein define the level of risk that a subject has of having or developing oral complications as described herein, as compared to a control subject.

A sample of this invention can be cells, tissue and/or fluid from the oral cavity of a subject, as well as any other biological material from the subject that can be used to identify the oral microbiome signature of the subject.

As will be understood by one skilled in the art, there are several embodiments and elements for each aspect of the claimed invention, and all combinations of different elements are hereby anticipated, so the specific combinations exemplified herein are not to be construed as limitations in the scope of the invention as claimed. If specific elements are removed or added to the group of elements available in a combination, then the group of elements is to be construed as having incorporated such a change.

The present invention is more particularly described in the following examples that are intended as illustrative only since numerous modifications and variations therein will be apparent to those skilled in the art.

EXAMPLES

Example 1

The general purpose of this invention is to use gene expression of a panel of candidate genes and X-linked epigenetic signatures affecting this panel of genes as biomarkers for the prediction of risk, progression, and/or response to treatment for exocrine and systemic complications of Sjögren's syndrome (SS). A panel of genes has been recently identified by computational systems biology approach in our lab.

The mRNA and/or (modified) protein expression pattern of these genes in saliva, salivary gland biopsies or labial/buccal brush biopsies obtained at the vicinity of minor salivary glands, in combination with X-linked epigenetic read-outs (X-linked expression of retro-elements and candidate genes), is potentially predictive of risk, progression and severity of exocrine complications associated with autoimmune responses in SS. History of infection with viruses exhibiting high tropism with salivary glands (Herpes virus, EBV, HCV) may be considered as intrinsic risk factor in relation to transient epigenetic activation of retro-elements that affect X-linked and non-X-linked candidate genes.

The diagnosis of SS requires the determination of foci of lymphocyte (B-cell) infiltration in the salivary glands undergoing destruction and in some cases the presence or autoantibodies against Sjögren's syndrome antigen A (SSA). Surgical biopsy of about 10 minor salivary glands of potential SS patients presenting for unexplained xerostomia (dry mouth) is required for definite diagnosis. The use of gene expression for the proposed panel of genes in combination with epigenetic X-linked retroelement expression in saliva and/or epithelial cells obtained by mucosal brush biopsies (yielding epithelial cells from the 3 layers) has never been tested.

The currently invasive surgical method for pathological examination and foci scoring cannot predict how fast and how severe Sjögren's syndrome will progress. Our proposed method would be minimally invasive and more likely help determining/monitoring how the disease progresses. Indeed, salivary gland biopsies cannot be repeated on regular basis, while brush biopsies may be repeated in a different area of the oral cavity (labial or buccal) after complete healing of the area used for previous brush biopsy.

We will develop an ELISA to detect the protein expression of a panel of candidate biomarkers that relate to the destruction of salivary glands in saliva and epithelial cells collected by brush biopsy at the vicinity of minor salivary glands. We will develop a qRT-PCR assay to measure mRNA transcripts of candidate genes in epithelial cells collected at the vicinity of the minor salivary glands. For the panel of candidate genes, we will also develop locus-specific DNA methylation assays to determine X-linked epigenetic changes that affect these genes in salivary gland biopsies. Because levels of sex hormones in saliva directly affect gene expression of salivary glands subject to inflammation, these will be measured in saliva using existing clinical diagnosis kits. The diagnostic information provided by these tests will be used to better manage SS patients in tailored personalized manner.

We have recently used computational systems biology tools to identify a unique panel of candidate genes relevant of Sjögren's syndrome X-linked epigenetic etiology and progression. We used a novel combinatorial computational approach which combined text mining (i.e., biosemantics concept mining) and gene expression meta-analysis of available microarray datasets from peripheral blood mononuclear cells [PBMCs] (1 dataset) and salivary glands (3 independent datasets minor and parotid glands) of female patients only. For all three salivary glands datasets, five genes (ETS1, LEF1, TIMP1, CHEK1 and CXCL10) associated with SS per concept mining were found differentially expressed in salivary glands of SS female patients. These genes can directly upregulate the expression or increase the effective activity of the metalloprotease MMP9 responsible for destruction of the extracellular matrix (ECM) normally maintaining the integrity of the salivary gland. ETS1, LEF1, CHEK1 and CXCL10 were found upregulated in the salivary glands, likely explaining upregulation of MMP9 observed in all three datasets. In contrast, TIMP1 expressed by X-chromosome was found downregulated. TIMP1 represents the only known post-translational inhibitor of MMP9 function (i.e. limiting factor), therefore suggesting increased MMP9 activity. In addition, we also found TLR7 (able to upregulate CXCL10) overexpressed in all three salivary glands datasets, while studies focusing on the adaptive autoimmune response have reported that TLR7 was not differentially expressed in PBMCs. Innate immune TLR7 gene is encoded by X-chromosome and was shown to regulate Alu retroelements expression in PBMCs of patients with systemic lupus erythematosus (SLE), an autoimmune disease related to SS.

SS is more prevalent in women (9:1) than men and to a larger extent than SLE (7:1) and an X-chromosome dosage effect was established for both SS and SLE. Therefore, we believe that epigenetic changes associated with abnormal X-chromosome inactivation and abnormal expression of the non-LTR retrotransposons LINEs (long interspersed elements) could affect the basal and inducible expression of TLR7 and TIMP1 in the salivary glands. LINEs, the only constitutively active retroelements in human genome, controls the expression of Alu retroelements. Both LINEs and Alu retroelement play a role in X-linked chromosomal inactivation. In addition, Alu retroelements were recently shown to be abnormally expressed in PBMCs of SLE patients. As pointed in our recent publication (Brennan and Mougeot, 2016), investigation of this regulation in PBMCs and salivary glands of SS patients has not yet been conducted to provide clues on SS etiology.

Based on this knowledge, however, for the purpose of this invention, we believe that in the presence of underlying X-linked epigenetic deficiency, upon stimulation such as transient viral infection, continuous B-cell infiltration and MMP9 upregulation leads to the development and progression of SS. As a corollary, our panel of genes affected by epigenetic changes, may play an essential role in priming of autoimmune disease by transient viral infection and in the ongoing destruction of the extracellular matrix of salivary (hence lachrymal) glands.

We are currently investigating gene expression of all above mentioned genes constituting our candidate panel biomarkers in saliva and/or minor salivary gland biopsies (prior to implementing brush biopsies for repeated measures). The expression of retrotransposon LINE may be measured by specific protein (LINE1 ORF1) directly reflective of LINE mRNA expression. Locus-specific X chromosome DNA methylation will be determined using commercially available custom designed kit.

The clinical strategy will be to monitor changes over time for our panel of genes in saliva at the time of initial diagnosis of salivary gland biopsies, and subsequently at multiple time points using brush biopsies and/or saliva. The diagnostic evaluation will also include a determination of locus-specific X-linked epigenetic changes at the time of initial diagnosis of salivary gland biopsies. Results from these tests will help predict severity and progression of Sjögren's syndrome and guide physicians for better management of SS patients.

Nobody has yet established or claimed the simultaneous deregulation of five genes targeting MMP9 in salivary glands in a single report. Within our panel of genes, ETS1 and LEF1 were never described as related to SS pathobiology in human samples. In addition, LINE1 (i.e., LINE retroelement), involved in HGF/ETS1 signaling pathway, has been recently shown to exhibit defective expression in SS and SLE. However, no connection with ETS1 differential expression has yet been made. The reason for us to identify ETS1 as a novel candidate, is that no one has conducted the type of metadata gene expression analysis guided by concept mining we performed. Also, most investigators in the field focus on the immunological component of SS even when analyzing salivary glands, with the assumption that autoimmune deficiency comes first, while we believe the initial deficiency comes from the salivary gland. Indeed, there exists a congenital disease resulting from skewed X-chromosome inactivation known as X-linked hypohidrotic ectodermal dysplasia that affects sweat glands specifically. In addition, our meta-analysis excluded male patients or male controls, while the analyses presented for microarray data in SS and SLE across the literature did not consistently make this distinction probably due to sample size considerations.

In addition, to explain how an abnormal X-chromosome inactivation by DNA methylation (involving LINE and Alu retroelements) could lead to an X-chromosome dosage effect in SS and SLE, we believe that the process results in over inactivation of TIMP1 and under-inactivation of TLR7, which is located on the same chromosomal arm as TIMP1. It is however, unclear why the subset of five genes of our panel (ETS1, LEF1, TIMP1, CHEK1 and CXCL10) are simultaneously differentially expressed per our analysis, thereby likely to upregulate the expression of MMP9 to levels that disrupt the integrity of salivary glands, further exacerbating destruction by infiltrating B-cells that secrete pro-inflammatory cytokines and are attracted by continuous viral-like stimulation of TLR7-CXCL10 pathway.

Example 2. Analysis of Pathway Signatures Associated with Sjögren's Syndrome, Systemic Lupus Erythematosus and Rheumatoid Arthritis: A Knowledge-Based Data Mining Approach Abstract Background:

Sjögren's syndrome (SS), systemic lupus erythematosus (SLE), and rheumatoid arthritis (RA) are autoimmune disorders with overlapping pathologies and symptoms. Despite extensive research, the etiologies of these diseases are not fully understood. In this study, a comprehensive knowledge-based data mining approach was used to identify pathway signatures common to SS, SLE and RA.

Methods:

Using the knowledge-based concept text mining tool Anni 2.1, genes associated with SS, SLE and RA were identified. Lists of common genes were established using a stepwise stringency approach. The cut-off of 2500 genes associated with each disease was selected, resulting in 1849 genes common between SS-SLE and 1674 between SS-RA. These genes were compared to the genes of SS, SLE and RA PMBC micro-array data sets with fold changes ≥1.5 or ≤1.5. Genes differentially expressed (DE) common with the CPA analyzed genes were studied for their expression in salivary glands, synovial biopsies, and synovial fibroblasts of SS, SLE and RA, respectively. Common genes with DE were selected for gene ontology determination and disease pathway analysis using GeneCodis.

These lists were used for pathway analysis and gene ontology determination using GeneMANIA and GeneCodis programs. Corresponding molecular networks for each list were manually enriched in order to associate molecular functions to upstream genetic regulations. Expression profiles of regulatory genes and their downstream targets for each disease were determined based on NCBI GEO2R gene expression datasets obtained from patients' and control subjects' biological samples (significance level p<0.05). The gene ontology and pathway analysis programs, GeneMANIA and Reactome, were used to further characterize altered molecular pathways.

Results:

Common pathways mostly relevant to SS, SLE and RA pathophysiology were identified. Among these pathways, subsets of genes including upstream regulatory and downstream target genes were found to be differentially expressed. The pathways identified were representative of biological processes such as intestinal immune network for IgA production, cytokine-cytokine receptor signaling, T-cell receptor signaling, regulation of leukocyte activation, chemotaxis and T-cell co-stimulation. For all levels of stringency tested, significantly more genes were found in common between SS and SLE than SS and RA.

Conclusions:

Using knowledge-based concept mining, we identified altered gene interactions and regulations common to SS, SLE and RA. Combining CPA and meta-analysis of gene expression of related disease is useful in finding common gene interactions between SS, SLE and RA. These gene interactions and regulations can be potentially used to better characterize disease processes.

Significance:

Previous studies have identified genes commonly deregulated in SS, SLE and RA. In this study, we show that a knowledge-based data mining approach may help elucidate complex relationships between genes and their association with disease pathways.

Introduction

Sjögren's syndrome (SS) is a systemic auto-immune disease with an unknown etiology. SS mainly occurs in females and is characterized by severe dry mouth and dry eyes. SS clinically and pathologically shares similarity with SLE and RA. Concept profile analysis (CPA) could help finding the hidden associations between common genes of related diseases. Combining CPA and meta-analysis of related diseases is useful in finding common gene interactions between SS, SLE and RA.

Objective

Combined concept profile analysis (CPA) with gene expression meta-analysis to identify specific genes and pathways involved in the etiology and pathogenesis of Sjögren's syndrome Methods Identification of common genes between SS, SLE and RA using CPA. Genes found by CPA with PBMC datasets of SS, SLE and RA patients were used for Meta-comparison. Selected common genes between CPA and DE PBMC dataset were analyzed for their gene expression in salivary glands, synovial biopsies and synovial fibroblasts of SS, SLE and RA datasets, respectively. Selected genes from our previous analysis were grouped based on the GO and KEGG disease pathway analysis.

Results

Results are shown in FIGS. 3, 6, 7 and 8.

Conclusions

Combining CPA and meta-analysis of gene expression of related diseases are useful in finding common gene interactions between SS, SLE and RA. These gene interactions and regulations can be potentially used to better characterize disease processes.

Example 3. Biosemantics Guided Gene Expression Profiling of Sjögren's Syndrome: A Comparative Analysis with Systemic Lupus Erythematosus and Rheumatoid Arthritis Background.

Sjögren's syndrome (SS) shares many pathological and clinical similarities with systemic lupus erythematosus (SLE) and rheumatoid arthritis (RA). These three rheumatic diseases overwhelmingly affect females over males. However, the disease etiology for these devastating auto-immune diseases are not yet known.

Objective.

In this study, combinatorial concept profile analysis and gene expression meta-analysis was used to identify specific genes may be involved with the SS etiology and pathogenesis.

Methods.

Using knowledge-based concept mining tool ANNI 2.1, genes associated with concepts SS, SLE and RA were identified and compared to find overlapping genes. Genes common between SS and SLE were compared with the differentially expressed (DE) genes of SS and SLE PBMC data sets of female patients. Similarly, genes common between SS and RA were compared with DE genes belong to the RA PBMC dataset of female patients. All DE genes in SS, SLE and RA PBMC datasets common with SS-SLE or SS-RA overlapping CPA genes were searched for their expression in the primary disease sites for each disease SS, SLE and RA, salivary glands synovial biopsies and synovial fibroblast respectively. Genes which are DE in at least two out of three SS salivary gland micro array datasets were used for gene enrichment analysis.

Results.

Our analysis identified a total of 21 different genes showing DE in salivary gland datasets of SS patients but never shown to be associated with SS pathogenesis before. Among them, higher levels of ETS1, LEF1 and lower levels of TIMP1 observed in our analysis correlated with the higher levels of MMP9, which is implicated to affect the salivary gland structure and facilitate hypo-salivation in SS patients and its expression was higher in SS salivary gland datasets. We also found that CXCL10 chemokine levels are higher in the salivary glands of SS patients. CXCL10 have been shown to be important in SS pathogenesis and have ability to increase the MMP9 expression.

Conclusion.

ETS1, LEF1, TIMP1 and CXCL10 might contribute greatly in SS pathogenesis and ETS1, LEF1, and TIMP1 could be useful as novel biomarkers of the disease.

Sjögren's syndrome (SS) is a chronic autoimmune disease affecting about 0.5-3% of the given population. SS is primarily characterized by dysfunctional exocrine glands due to lymphocytic infiltration resulting in excessive dry mouth (xerostomia) and dry eyes (keroconjunctivitis Sicca). Autoimmune diseases often share common clinical and pathological features with each other such active innate immune response, chronic inflammation, development of specific autoantibodies, systemic dysfunction of multiple organs etc. SS is most closely associated with the two autoimmune disorders, systemic lupus erythematosus (SLE) and rheumatoid arthritis (RA). Auto-immune diseases are usually more common in females than males. In particular, SS and SLE overwhelmingly affect females to males, with 9:1 ratio. RA also affects more females than males but less drastically (2-3:1).

Despite overlapping pathophysiological markers shared among SS, SLE and RA patients, the exact mechanism responsible for the onset and progression of these diseases is not fully understood. In recent years, in the search for biomarkers unique to SS or common to SS, SLE and RA several meta-analyses studies have attempted to compare multiple SS gene expression datasets with each other or in conjunction with SLE and RA. In these studies, expression analyses were conducted using peripheral blood mononuclear cells (PBMCs) or biopsies of tissues affected in each disease, i.e., salivary glands in SS, and synovial biopsies in SLE and RA.

These meta-analyses studies mostly focused on the identification of genes demonstrating largest fold changes in mRNA expression in SS patient samples compared to controls. However, large fold changes in transcriptional expression of certain genes observed in these studies could be irrelevant to disease etiology as these may be characteristic of the symptomatology in advanced stages of the disease, rather than disease-onset or pre-symptomatic stages. For example, high levels of type I interferon related genes (e.g., IFN-alpha) are expressed in PBMCs and salivary gland biopsies in SS. However, in salivary glands, increased type I IFN expression could be largely attributed to the frequently observed lymphocytic infiltration and not directly related to etiological mechanisms that would initiate in the salivary glands. Indeed, recently identified potential disease susceptibility genes and infection by viruses with high tropism for exocrine glands are suspected to play an important role in the etiology of SS ahead of the development of systemic autoimmune responses.

Moreover, while SS predominantly occurs in females and an X-chromosome dosage effect was recently identified, previous meta-analysis studies comparing SS, SLE, and RA mostly used gene expression data containing both male and female patients. There is mounting body of evidence suggesting that higher susceptibility to SS in females could be associated with the aberrant expression of specific genes located on the X chromosome in conjunction with X chromosome linked epigenetic events possibly involving the activation of endogenous retroviruses.

In addition, the use of concept profile analysis (CPA) has emerged as a promising approach for biomedical discoveries especially when the amount of data is limited, inadequate or limited categories of controls are used, or there is a lack of general understanding in disease mechanisms. Similar to gene ontology analysis approaches, in CPA each biological entity (e.g., genes, diseases, symptoms, pathways, chemicals, drugs, tissues, toxins . . . etc.) can represent a concept of a concept list (or profile) of another concept and be ranked in order of relevance within the list defining a hierarchy, based on literature mining.

In this study, we used CPA to establish lists of genes relevant to SS, SLE and RA with the goal of identifying novel candidate markers of SS etiology or markers critical to the development of SS. Genes common to SS, SLE and RA and genes unique to either disease were identified. Publically available gene expression datasets were used to determine the differential expression of candidate genes in female population only.

Concept Profile Analysis Using ANNI 2.1 Program.

Anni 2.1 program, an online concept-mining tool, was used to perform concept profile analysis (CPA). Anni 2.1 systematically retrieves literature that contains two concepts such as gene and disease in an abstract and ranks the genes with the highest occurrence in literature in decreasing order Anni 2.1 uses a vector space model to generate association scores and then ranks them accordingly. A higher score is associated with a greater occurrence of a particular gene and queried disease, thereby reflecting a degree of association. Scoring by Anni 2.1 is also based on the identification of pairs of concepts never found together in an abstract but associated with a third concept occurring in an abstract with either concept of a pair (co-occurrence).

Anni 2.1 was first used to compare concept profiles related to SS, SLE and RA and retrieve previously published literature (PubMed abstract mining). Further, using a query to match *Homo sapiens* genes (Anni 2.1 embedded human genome database) with each of the concepts ("Sjögren's syndrome", "systemic lupus erythematosus", "rheumatoid arthritis"), genes were ranked based on their degree of associations with each disease through published literature.

After processing of duplicates and errors in the three Anni 2.1 output listings, arbitrary cut-offs in gene ranking (i.e., 250, 500, 1000, 2500, 5000) were tested to determine appropriate stringency limiting non-specific over representation and at the same time reducing the need for pathway-related gene enrichment procedures in downstream in silico functional genomics analyses. Thus, appropriate stringency was obtained with a cut-off of 2500 genes retrieved for each disease SS, SLE and RA. The three lists of 2500 genes were analyzed using a Venn diagram generator (bioinformatics.lu/venn.php) to determine subsets of genes common to all three or pairs of diseases, or those unique to each disease. Subset of genes were used to determine differential expression of each gene using publically available gene expression databases and to investigate their SS-related biological functions using gene ontology and molecular network analysis programs.

Because Anni 2.1 PubMed database latest update was performed in 2010, manual PubMed searches (2010 to 2016) were conducted using keywords corresponding to concepts with greatest association with each disease per Anni 2.1 to ensure that more recently discovered genes were included in the three listings of 2500 genes.

Gene Expression Analysis of PBMCs and Primary Disease Site in Females.

Gene expression datasets obtained from PBMCs or tissue biopsies from SS, SLE, and RA patients and controls were retrieved by searching NCBI GEO (Gene Expression Omnibus; ncbi.nlm.nih.gov/geo/) database using the terms, "Sjögren's syndrome", "systemic lupus erythematosus" and "rheumatoid arthritis" f through May 2016 (Table 1).

To select gene expression datasets used in our study, following criteria had to be met: (1) The gene expression dataset was generated from biological samples obtained from patients and controls that were age-matched overall, (2) Due to the higher incidence of SS, SLE and RA in females, either the dataset contained female subjects only or the male subjects were removed for further analysis, and (3) Expression datasets from animal studies were excluded.

Out of 16 for SS, 21 for SLE and 27 for RA gene-expression datasets, only three microarray datasets of PBMCs, i.e., one per each disease met all the criteria (GSE48378-SS, GSE10325-SLE, GSE15573-RA). As one dataset (GSE48378) did not contain gene symbols in the output, RefSeq IDs were converted to gene symbols using gene ID conversion tool (g:Profiler).

For disease site-specific analyses, five datasets out of were retrieved from GEO database, including three for SS patients (salivary glands: GSE23117, GSE40611, GSE40568), one for SLE (synovial biopsies: GSE36700) and one for RA (synovial fibroblasts: GSE7669).

For all selected datasets, differentially expressed genes in SS, SLE or RA female population were identified using online web application GEO2R (ncbi.nlm.nih.gov/geo/geo2r/) and. For individual probes of candidate genes identified by Anni 2.1 and PubMed searches, fold changes in expression were determined using the formula $2^{\wedge}(\log FC)$. To ensure the gene expression data analysis was unaffected by genes represented by multiple probes values, the same probe was used per each gene across all datasets Gene Enrichment and Functional Network Analysis.

Differentially expressed (DE) genes were selected for enrichment analysis if they exhibited at least 1.5 fold change in at least two out of the three SS disease site (i.e., salivary glands) related datasets (GSE23117, GSE40611, GSE40568) Selected DE genes were enriched using Gene Ontology (GO) biological processes and Kyoto Encyclopedia of Genes and Genomes (KEGG; genome.jp/keggf) pathways functional analysis module in GeneCodis (genecodis.cnb.csic.es). To identify functional associations between the enriched subsets for each disease (i.e., SS, SLE, and RA), the "Search Tool for the Retrieval of Interacting Genes/Proteins" (STRING-db; string-db.org/) server was utilized. To expand upon on our functional network and provide complementary connections within and between gene clusters, we included the major genes identified to contain SNPs associated with disease susceptibility in SS patients by two independent genome wide association studies.

The overall strategy used to identify genes associated with SS, SLE, and RA consisted of four phases (summarized in FIG. 1). The first phase (Phase 1) consisted of concept profile analyses and matching to human genome by prioritizing the comparison SS with SLE and SS with RA. Phase 2 consisted of the analysis of differential mRNA gene expression in PBMCs of female patients using NCBI GEO datasets (Table 1) to determine genes common to the three diseases and those uniquely common to SS and SLE or SS and RA. Phase 3 extended the gene expression analysis to disease sites (e.g., NCBI GEO datasets obtained from salivary glands for SS, synovial biopsies for SLE, and synovial fibroblasts for RA; Table 1) for those genes determined in Phase 2 to be differentially expressed in PBMCs of SS, SLE and RA female patients. Phase 4 corresponded to gene enrichment and functional analyses using computational systems biology tools. The results from this approach are summarized below.

Phase 1: Knowledge-Based Correlation Analysis of Genes Associated with SS, SLE and RA.

Using Anni 2.1 online program, concept profiles were obtained for the three diseases SS, SLE, and RA.

Our query matching the three concepts: "Sjögren's syndrome", "systemic lupus erythematosus", and "rheumatoid arthritis" with the list of human genes embedded in Anni 2.1 as "*Homo Sapiens* genes" concept, retrieved all known human genes associated with each disease to a variable extent based on abstract occurrence in PubMed. From the ranked gene output generated by Anni 2.1, we selected the top 2500 genes providing appropriate stringency for downstream gene ontology and molecular network analysis (see Methods section). A Venn diagram was generated to highlight all common and unique genes for SS, SLE and RA found by our concept profile analysis (CPA) (FIG. 2).

Figure 2:
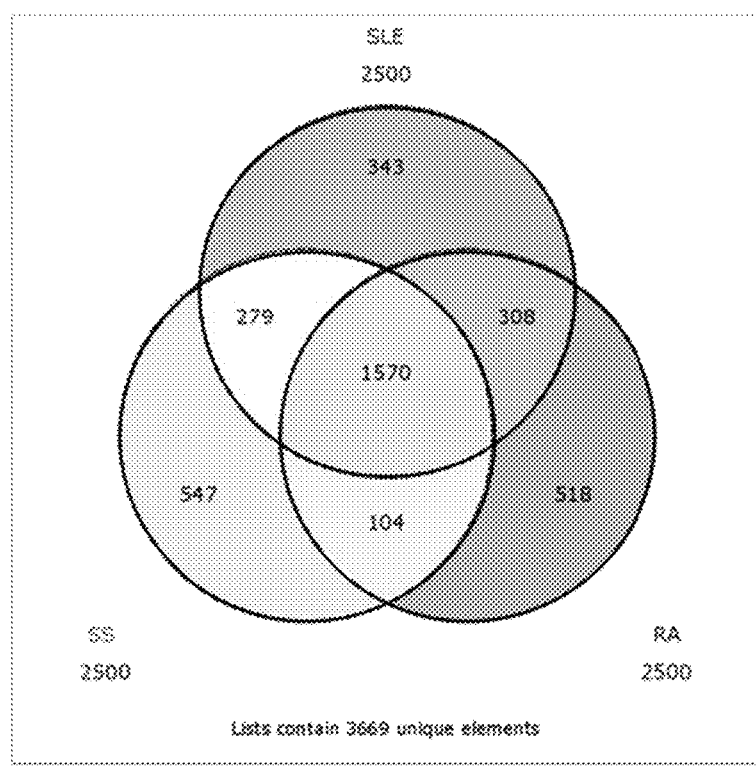
FIG. 2. Meta-comparison of all text mined genes (up to 2500 per disease) for SS, SLE and RA. The lists of 2500 genes per disease: Sjögren's syndrome (SS), systemic lupus erythematosus (SLE), and rheumatoid arthritis (RA), found by text mining tool, Anni 2.1, were compiled and compared to generate a Venn diagram. Total 1570 genes (62.8%) were common among the three diseases. 279 genes were found in common between SS and SLE only, while 104 genes common between SS and RA only.

As shown in FIG. 2, a total of 1570 genes (62.8%) were common between the three related auto-immune diseases. Moreover, 279 genes were found to be uniquely common between SS and SLE compared to RA. Similarly, 104 genes were found to be uniquely common between SS and RA compared to SLE (FIG. 2). These results suggest that SS and SLE share greater similarity than SS and RA in terms of common gene representation.

Phase 2: Comparative Gene Expression Analysis of PBMCs in SS, SLE and RA Female Patients.

Figure 3:
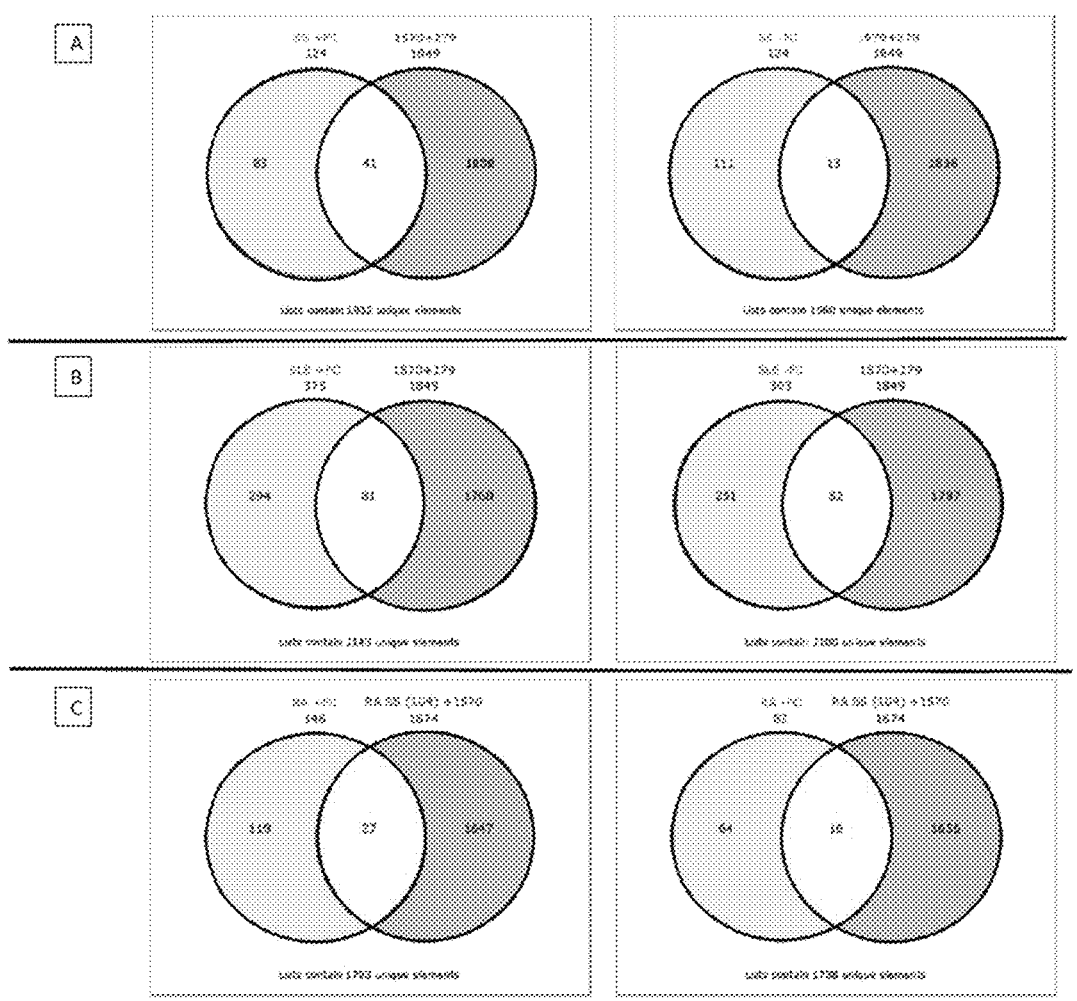
FIG. 3. The meta-comparison of genes with +/−Fold change sorted and curated microarray data sets of PBMCs of female SS, SLE and RA patients with selected CPA genes of phase 1. After acquiring PBMC microarrays for all three diseases (SS SLE, RA) from NCBI GEO, the genes were sorted and separated based on their gene expression variation with the cutoff of +1.5 for +FC and −1.5 for the −FC for each diseases SS, SLE and RA (SS +FC, SS −FC, SLE +FC, SLE −FC, RA +FC and RA −FC). (Panel A) Selected genes from PBMC data sets of SS (SS +FC and SS −FC) were compared with the common genes between SS, SLE and RA (1570) and between SS and SLE (279). (Panel B) Selected genes from PBMC data sets of SLE (SLE +FC and SLE −FC) were compared with the common genes between SS, SLE and RA (1570) and between SS and SLE (279). (Panel C) Selected genes from PBMC data sets of RA (RA +FC and RA −FC) were compared with the common genes between SS, SLE and RA (1570) and between SS and RA (104).

PBMC gene expression analysis using datasets for each disease (Table 1) was performed using NCBI GEO2R online R-based expression analysis tool to identify differentially expressed (DE) genes (fold changes (FC) ≥1.5 in either up or down direction) in the female population. A total of 248 DE genes (124 up, 124 down) in SS, 678 DE genes (375 up, 303 down) in SLE and 228 DE genes (146 up, 82 down) in RA were identified (FIG. 3).

As shown in FIG. 2, a total of 1849 genes (1570+279) were found in common between SS and SLE and 1674 (1570+104) between SS and RA per CPA. Genes differentially expressed in PBMCs of patients compared to controls, i.e., 248 genes in SS and 678 genes in SLE, were compared to the 1849 SS & SLE common genes determined by CPA. A total of 41 and 81 (upregulated) and 13 and 52 (downregulated) genes in PBMCs of SS and SLE patients respectively, were found in common with the 1849 SS & SLE CPA determined genes. (Tables 5-8, FIGS. 2, 3A and 3B). (In addition, the 228 DE genes in PBMCs of female RA patients were compared to the 1674 genes in common between SS and RA per CPA analysis. A total of 27 upregulated and 18 downregulated genes were found in common (Tables 9-10, FIGS. 2, 3C).

Phase 3: Expression Analysis of Candidate Genes Associated with SS in Salivary Glands of Female Patients.

After the comparative gene expression analysis of SS, SLE and RA PBMCs, we proceeded to investigate the fundamental role played by DE genes individually and coherently in each disease or patients with SS. The primary pathological manifestation that defines SS occurs in the major and minor salivary glands in the oral cavity. SS is characterized by periductal lymphocytic infiltration of the glands and destruction of acinar cells. In addition, although SLE and RA are autoimmune disorders similar to SS, they affect different tissues as the primary pathological manifestation, such as swelling and inflammation of skeletal joints of both SLE and RA.

Thus, for SS, three types of microarray datasets were selected: those generated from parotid glands (a major salivary gland), labial salivary glands (subset of minor salivary glands), and minor salivary glands (broader location distribution in oral cavity) (Table 1.). For SLE and RA, microarray expression datasets were obtained, respectively, from the synovial biopsies and synovial fibroblasts, which surround many of the major skeletal joints. All DE genes of PBMCs from SS, SLE and RA datasets that are common with the CPA analysis (41+13 (SS), 81+52 (SLE) and 27+18 (RA)) were used to search for their expression at the primary disease site of SS (salivary glands).

Our analysis identified 76 DE genes in at least two out of three salivary gland microarray datasets obtained from SS patients (Table 2). Out of these 76 genes, we found 27 genes (marked by grey color) never shown to be associated with the pathogenesis of SS (Table 2). To understand the potential role of these genes in the pathogenesis of SS, all 76 genes were used for functional classification and molecular network-related pathway analysis.

Phase 4: Functional Classification and Molecular Network Pathway Analysis of Candidate Genes.

For the 76 DE genes differentially expressed in at least two types of salivary glands in SS female patients, we used Genecodis web service tool for functional classification. An analysis of gene ontology (GO) biological process revealed several major functional categories in which the genes were grouped. In particular, the functional categories included cytokine mediated signaling, type-1 IFN response, response to virus (Table 3). These GO functional categories have been previously shown in literature to be associated with SS and other autoimmune diseases. Next, to determine the functional association between these genes, we created a gene interaction map (molecular network) using STRING-db web service. STRING-db formulates gene maps with connections/interactions derived from both empirical evidence (including literature sourced through text-mining) and functionally predicted interactions based on characteristics such as protein structure.

Figure 4:
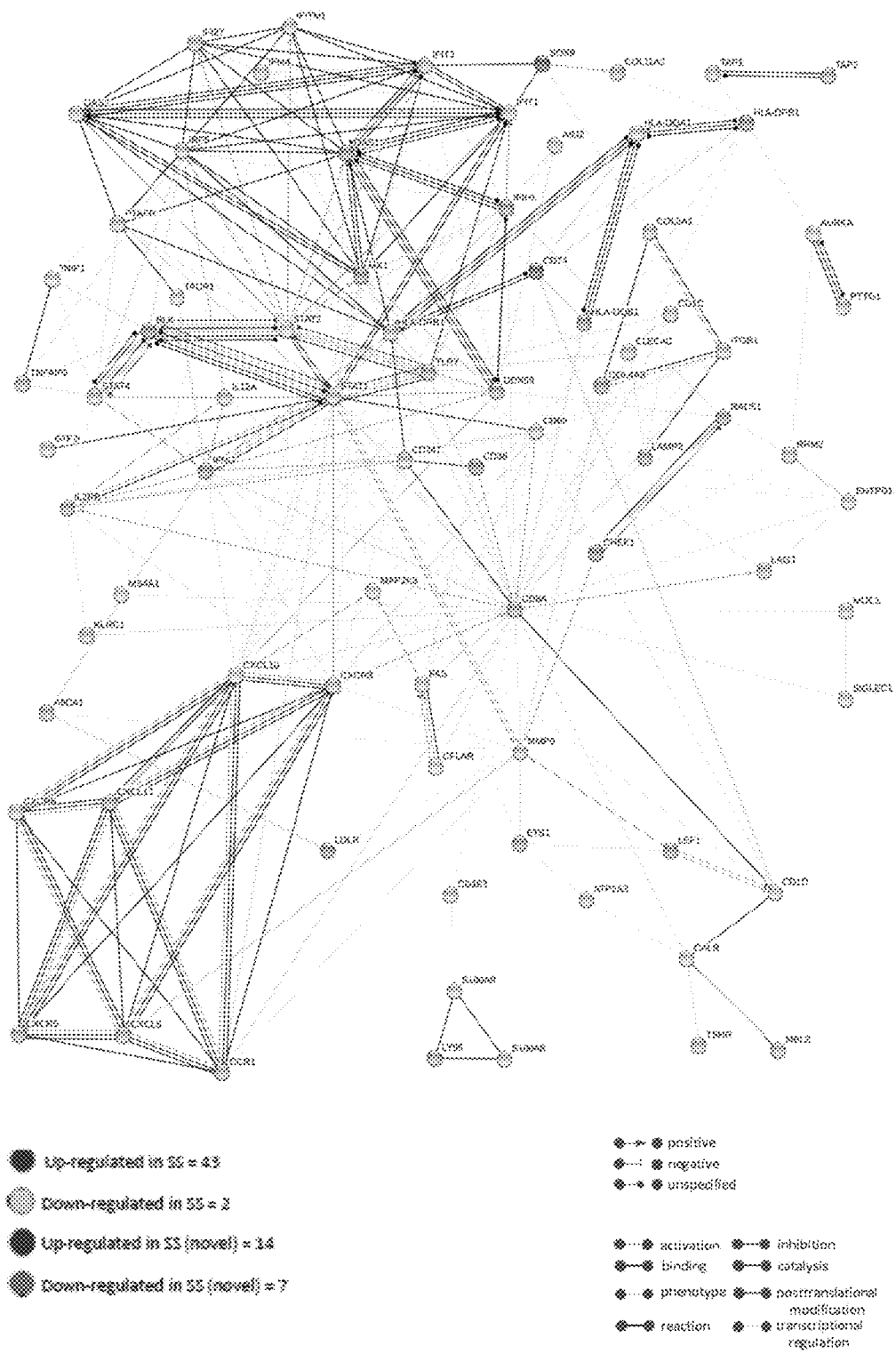
FIG. 4. Network Pathway analysis of 76 selected significantly dis-regulated genes with emphasis on three sub-networks. Employing the online program STRING, we generated a broad interaction network from our selected 76 genes. Within the network, we assigned particular colors to each node (gene) to represent the expression of that particular gene in SS patients. The nodes colored yellow are originally derived from previous GWAS of SS patients and are added for the validation and strengthening of our independently derived network. The nodes with colors red and light green represent genes up-regulated and down-regulated in SS respectively. Similarly, nodes with maroon and dark green colors represent genes exhibiting up-regulation and down-regulation in SS respectively but never been shown to be associated with SS patho-physiology before. The lines connecting nodes, known as edges, represent interactions between two nodes and can be derived from evidence or inferred from previously known data: magenta-experimentally derived, blue-predicted interaction through gene co-occurrence, grey-predicted functional interaction derived from either homologous protein interactions in other species/associations in curated databases/co-mentioned in Pubmed abstracts, Yellow-transcriptional regulation (experimentally derived), black-reaction (experimentally derived), Purple-catalysis (experimentally derived). Edges ending in a green arrow, red bar, or black circle represent an action between the two nodes that can range from positive, negative, or unspecified respectively.

To further substantiate the relevance of our methodology and findings, we incorporated multiple genes previously found to have a likely impact on SS based on multiple Genome Wide Association Studies (GWAS) to our molecular network. By including major genes found by these GWAS (TNIP1, TNFAIP3, GTF2, STAT4, BLK, IL12A, HLA-DRB1, HLA-DQB1, PTTG1, HLA-DPB1, HLA-DQA1, COL11A2, TAP2) (in our network analysis, we identified several key interactions that intertwined seamlessly with our molecular network model, thus further supporting our findings (FIG. 4). As shown in FIG. 4, all genes with red nodes (43) are upregulated and those with light green nodes are downregulated (2). All yellow nodes (14) represent genes found by independent GWAS on SS.

Our analysis also indicates that the 27 out of 80 genes make two sub-networks, each comprising a major biological pathway as marked by dotted black border (FIG. 4). The first pathway, type-I IFN pathway/immune response pathway (in dotted black circle) can primarily be attributed to the significant upregulation of interferon-stimulated genes (ISGs). The second major pathway (dotted black circle) is the chemotaxis initiation pathway. This pathway is the result of chemokine-related gene stimulation, which initiates dendritic cell recruitment to salivary gland areas.

Finally, we identified a total of 14 up-regulated genes (maroon nodes) and 7 down-regulated genes (dark green nodes), directly or indirectly associated with both type-I-IFN and chemotaxis pathways, but never been shown to be associated with SS in previous research (Table 2 (all genes with shaded grey background)).

The pathophysiology of autoimmune disorders such as SS, SLE and RA is complex, yet all share some clinical features such as active innate immune response, T-cell signaling and differentiation, chronic inflammation etc. The etiology for these diseases is poorly understood. However, for SS and SLE, there is a growing body of evidence that X-chromosome dosage, viral infection, and retro-element activation might play an important role in the onset of these diseases. Several gene expression studies have been published for SS and SLE in the past decade, although without specific focus on genes related to X-chromosome expression or retro-element activation.

The majority of previous approaches focused primarily on inter-disease gene expression between SS, SLE and RA at the expense of intra-disease gene expression. In previously performed meta-analysis studies on SS, SLE and RA, gene expression profiles of only PBMCs were reported. Other meta-analyses studies focused on a single disease (SS, SLE, or RA) using samples from the disease site (i.e., salivary glands for SS, synovial fluid for SLE, or synovial fibroblasts or RA. However, the primary disease manifestation sites of SS are major/minor salivary glands and lachrymal glands. A major caveat of these meta-analyses approaches is the lack of comparison between gene expression data of PBMCs and the primary site of disease pathology. As a consequence, mechanistic changes in PBMCs may correlate with changes in the primarily affected tissue of the particular disease or how these changes govern tissue-specific autoimmunity, remain largely unexplored.

To our knowledge, this is the first study combining concept mining analysis (CPA) and gene expression analysis at the site of disease and PBMCs concurrently in SS, SLE and RA using females only. Here, we analyzed independent PBMC datasets each for SS, SLE and RA and compared them with three data sets of salivary glands of SS, synovial biopsy samples of SLE, and synovial fibroblasts samples of RA patients.

In our study, we uncovered the potential impact of PBMC DE genes on tissue specific gene expression profiles related to SS. This fundamental comparison could provide a deeper understanding of the etiology of SS or like diseases. Our CPA results were juxtaposed to gene expression datasets of PBMCs across all three diseases (SS, SLE, RA) and further compared with disease specific tissue expression data. Using this method, we created a unique functional network map providing further insight into the complex etiology of SS. Minute curation of datasets and the use of CPA revealed 20

DE genes in female SS patients that have never been associated with SS pathophysiology.

Our analysis confirmed that matrix metalloproteinase 9 gene (MMP9) is upregulated in salivary glands of SS patients and has a role in salivary gland dysfunction. We identified four genes (ETS1, LEF1, TIMP1, and CXCL10) differentially regulated in SS patients, which can directly regulate the expression of MMP9. Higher levels of MMP9 have been detected in the salivary glands of SS patients by multiple studies. We hypothesize that MMP9 upregulation by concomitant dysregulation of a set of genes (ETS1, LEF1, TIMP1, and CXCL10) could be responsible for the initiation and pathogenesis of Sjögren's syndrome and should be considered for further evaluation as potentially novel etiological biomarkers of the disease. Further, TIMP1 is an X-linked gene that has been investigated for the effects of its polymorphisms in X-chromosome inactivation. We postulate that TIMP1 represents a key player in the understanding of the higher incidence rate of SS in females to males. Overall, we have demonstrated that combining knowledge-based concept mining (CPA) with properly curated gene expression datasets can be useful in identifying candidate biomarkers of complex diseases or targeted drug discovery.

Figure 5:
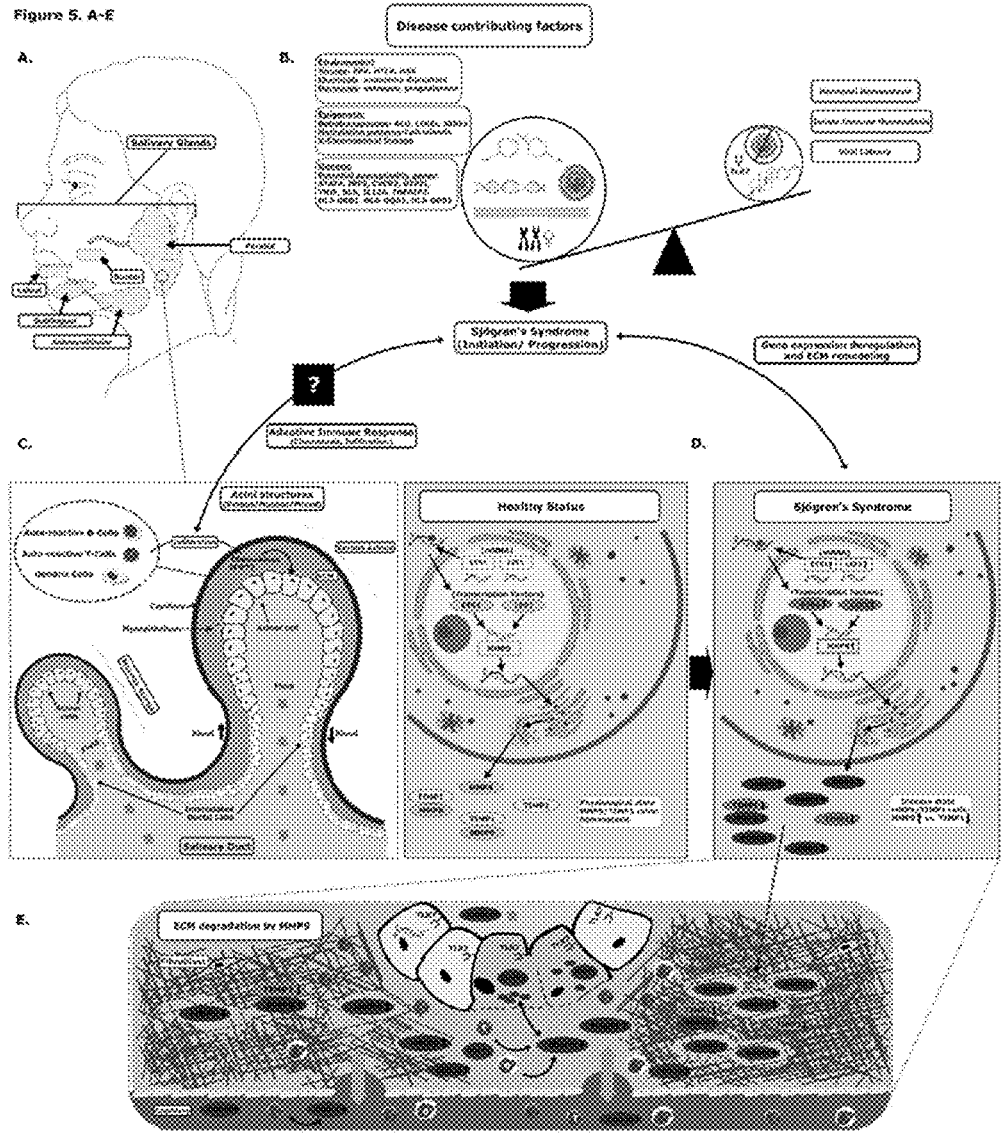
FIG. 5. Proposed model explaining the human salivary gland structure and Sjögren's syndrome pathogenesis based on the computational, gene expression and network analysis. Panel A. Major and minor salivary glands of the oral cavity. Sjogren's syndrome (SS) drastically depletes exocrine gland function on a system wide level. Salivary glands, a subset of exocrine glands, are all affected in the oral cavity and can lead to a host of problems. Panel B. Potential combinatorial factors may lead to SS. The pathology of SS is not fully understood at this point in time. The current model involves multiple factors that combined play a role the development of the disease. The primary factor is genetics which is acted upon by various environmental and retro-elements to eventually create an internal imbalance. It is still unknown whether this imbalance could impact the salivary glands first or affects the immune system first. Panel C. Salivary unit portion showing individual acinus. The salivary unit is made up of several components. Each gland has multiple acinus (bulb like structure at the ends of salivary units) predominantly comprised of acinar cells that secrete water, salts and/or protein (major components of saliva) into the oral cavity. In SS, capillaries surrounding salivary tissue mediate the immune response by passing various interferons and chemokines produced by acinar cells into the bloodstream which initiate the dendritic cell movement to the area. Panel D. Transcription factors ETS1 and LEF1 directly up-regulate MMP9 expression. MMP9, also known as gelatinase B, is a zinc-metalloproteinase that is involved in extracellular matrix degradation. Two transcription factors, ETS1 and LEF1, are both upregulated in PBMCs and two out of three salivary glands of SS patients. MMP9 potentiates glandular destruction by destroying the extracellular matrix (ECM) surrounding cells leaving the endothelial layers vulnerable to immune system destruction. The mechanism in which ETS1 upregulates MMP9 through binding to the MMP9 promoter region stimulating transcription. Panel E. MMP9 and CXCL10 feedback potentiate ECM destruction. CXCL10, a chemokine, stimulates dendritic cell recruitment to a specific area while at the same time has been shown to increase MMP9 expression in a positive feedback-like mechanism. When CXCL10 expression increases, MMP9 expression increases subsequently and may be due to the role of MMP9 in the degradation of CXCL10 (REF). TIMP1, also known as tissue inhibitor of metalloproteinases, binds directly to metalloproteinases, inhibiting their enzymatic activity. While MMP9 and TIMP1 are regulated in a ratio specific manner, in patients with SS MMP9 is severely upregulated while TIMP1 is downregulated, which may play a role in the progression of glandular destruction brought on by the disease.
Figure 6:
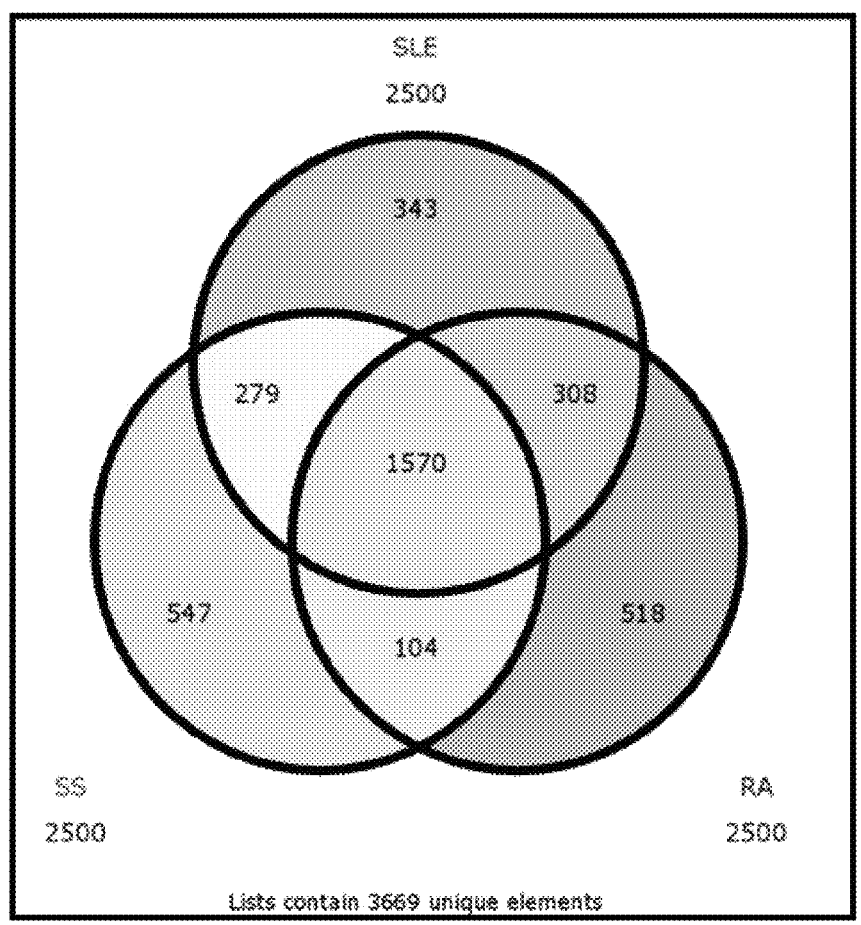
FIG. 6. Meta-comparison of all text mined genes (up to 2500 per disease) for SS, systemic lupus erythematosus (SLE) and rheumatoid arthritis (RA).

We summarized our finding with a proposed model for the pathogenesis of SS (FIG. 5). As described above, SS primarily affects the salivary gland and inhibits the salivary flow resulting in xerostomia (FIG. 5A). The major structural component required for salivary gland function is the bulb-like acinus structure predominantly comprised of acinar cells (FIG. 5C). Destruction of these acinar cells is vital in the pathogenesis of SS. Once damaged, these acinar cells could trigger inflammatory infiltration of the gland by secretion of various interferons and cytokines into surrounding capillaries. (FIG. 5C). While the etiology of SS is not completely understood, it is widely believed that multiple factors including genetics, retro-elements and environmental factors play role in SS development (FIG. 5B). Our network analysis revealed that among the 21 discovered candidate genes, upregulation of ETS1 and LEF1 mechanistically could increase the expression of MMP9, one of the major regulatory components of the extra cellular matrix (ECM) (FIG. 5D). Furthermore, both ETS1 and LEF1 have been shown to directly bind the promoter of MMP9 to increase its transcription. Most importantly, these two genes are not directly related to the immune response pathway. In turn, their high expression cannot be directly attributed to the infiltration of PBMCs as their expression levels remain unchanged in the PBMCs of SS patients.

MMP9 came under our scrutiny, as its expression is considerably higher in all of the salivary gland related microarray gene expression datasets, while its expression remained unchanged in the PBMCs of SS patients. We also found one of the most significantly upregulated chemokines, CXCL10 (in all SS patients' datasets) could stimulate the expression of MMP9. It is, however, important to note that CXCL10 expression is higher in PBMCs of SS patients compared to controls. Thus, infiltration of PBMCs could trigger the expression of MMP9 in salivary glands. In addition, CXCL10 is a chemo-attractant and known to trigger recruitment and chemotaxis of monocytes, which can further damage the ECM and salivary gland cells to potentially affect the saliva secretion (FIG. 5E). We also analyzed the expression of TIMP1, a major inhibitor of MMP9 in all salivary gland datasets of SS patients. As anticipated, its expression was lower in the salivary gland datasets of SS patients compared to controls. TIMP1 is located on the X chromosome and has been shown to be inactivated in polymorphic X-chromosomes.

Overall, our meta-analysis combining CPA and gene expression analysis supports the hypothesis that increased levels of MMP9 resulting from dysregulation of ETS1, LEF1, TIMP1 and CXCL10 might greatly contribute to the pathogenesis of SS.

Example 4. Novel Candidate Biomarkers of Sjögren's Syndrome Pathogenesis

Background.

Sjögren Syndrome (SS) is a chronic rheumatic autoimmune disease primarily affecting women. SS affects salivary glands (SGs) and lacrimal glands leading to dry mouth and eyes, systemic complications, and a 40 times greater risk of developing non-Hodgkin lymphoma.

SS pathogenesis involves overexpression of matrix metalloproteinase 9 (MMP9) and underexpression of tissue inhibitor of metalloproteinases 1 (TIMP1) in SGs. This imbalance contributes to the destruction of SGs and loss of salivary function.

In a recent meta-analysis of SG mRNA expression, using datasets of SS patients, our laboratory identified two upregulated transcription factors as candidate biomarkers: ETS proto-oncogene 1 (ETS1) and lymphoid enhancer binding factor 1 (LEF1). Also, vascular endothelial growth factor (VEGF) and gastrin releasing peptide (GRP) are known to play a role in post-translational activation of ETS1. The interplay between these factors in SS pathogenesis has not been investigated.

Objective.

Our objectives were to determine the effects of ETS1 and/or LEF1 overexpression on MMP9 and TIMP1 expression in: 1) SG cell lines; and 2) SG cell lines treated with VEGF or GRP.

Methods.

SG cell lines A253 and HSG were transfected with ETS1 and/or LEF1 plasmids for transient expression with and without GRP or VEGF treatment. Total RNA and total protein were extracted to quantify ETS1, LEF1, MMP9 and TIMP1 mRNA and protein levels by qRT-PCR and Western blot analysis, respectively.

Results.

Following the overexpression of ETS1 and/or LEF1, MMP9 expression increased and TIMP1 expression decreased in both cell lines at the mRNA and protein levels. In addition, VEGF and GRP treatment exacerbated the expression of MMP9.

Conclusions.

We showed, for the first time, that an MMP9/TIMP1 imbalance can be induced by LEF1/ETS1 in SG cells lines treated or untreated with VEGF and GRP. Indeed, overexpression of VEGF has been demonstrated in SGs of SS patients, and up to 45% of SS patients experience gastroparesis involving GRP regulation. These results support our hypothesis of ETS1 and LEF1 as candidate SS biomarkers. These findings can be translated to clinical research in managing primary SS patients, as well as patients with rheumatoid arthritis or systemic lupus erythematosus who develop secondary SS.

Example 5. Immunofluorescence Staining Showing Differential Expression

Figure 9:
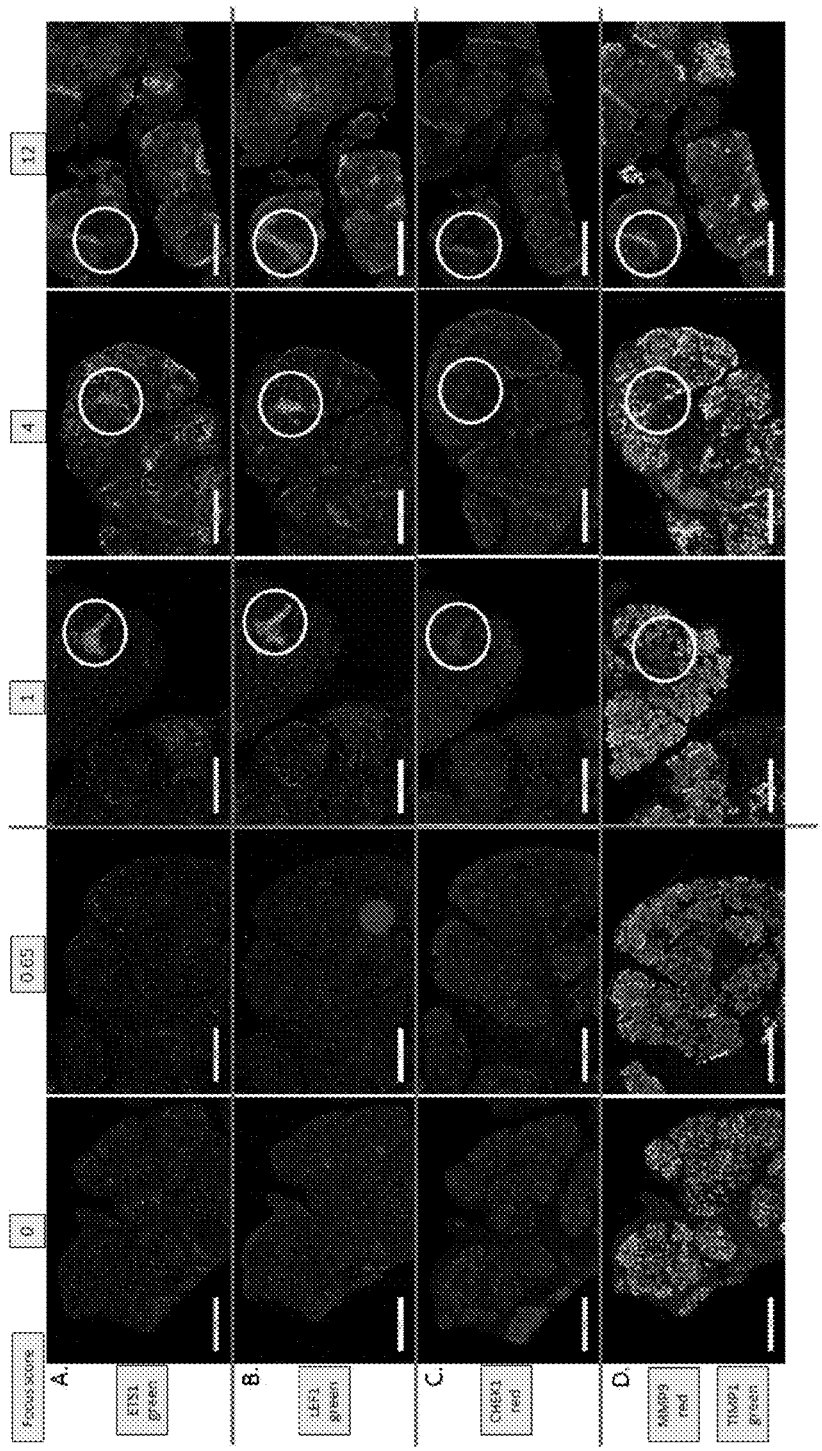
FIG. 9. Immunofluorescence staining showing differential expression of ETS1 (Panel A), LEF1 (Panel B), MMP9 (Panel C) and TIMP1 (Panel D) in labial salivary gland (LSG) tissues of Non-Sjögren controls (columns 1 and 2) and Sjögren syndrome (SS) patients (columns 3, 4, and 5).

FIG. 9 shows results of immunofluorescence staining that shows differential expression of ETS1 (Panel A), LEF1

(Panel B), MMP9 (Panel C) and TIMP1 (Panel D) in labial salivary gland (LSG) tissues of Non-Sjögren controls (columns 1 and 2) and Sjögren's syndrome (SS) patients (columns 3, 4, and 5). Increased expression of ETS1, LEF1 and MMP9 is shown in SS patients compared to the non-Sjögren controls. Co-localization of ETS1, LEF1 and MMP9 in LSG tissues of SS patients is shown (circled areas). Lower expression of TIMP1 in the exact same areas of LSG tissues in SS patients is shown (circled areas).

Example 6

Each year, about 5 in 100,000 people are affected by eye and/or mouth dryness (sicca), including 40-50% who have Sjögren's syndrome (SS), an autoimmune disease affecting exocrine glands, notably the salivary and lacrimal glands. The etiology of SS is poorly understood and while there are treatments to reduce symptoms or improve quality of life, there is no cure.

Classification of SS requires testing for the presence of autoantibodies and a biopsy to determine if there is histological evidence of characteristic lymphocytic infiltration of salivary glands. The health care cost associated with SS disease approximates $20,000 annually per patient and roughly 5% of SS patients ultimately develop lymphoma. Nine out of ten SS patients are women, most of whom are diagnosed near menopausal age. In addition to potential susceptibility genes, as have been determined by genome-wide association studies, an X-chromosome dosage effect resulting in genetic predisposition has been identified for SS as well as for the related autoimmune disease, systemic lupus erythematosus (SLE).

The epigenomic methylation profiles of SS patient salivary glands, as well as infiltrated B lymphocytes, are altered compared to those of sicca patients. The DNA methylation alterations can have an impact on maintenance of X-chromosome inactivation, i.e., can cause an X-chromosome dosage effect. Partial alleviation of X-chromosome inactivation can occur because of global hypomethylation events which result in the upregulation of X Inactive Specific Transcript (XIST) and higher expression of retroelement Long Interspersed Nuclear Element 1 (LINE-1), both of which are involved in the X-chromosome inactivation.

Classification of SS is established based on American College of Rheumatology-European League Against Rheumatism Classification (ACR-EULAR) criteria. In this classification, labial salivary gland (LSG) biopsies are collected for histological determination of lymphocytic infiltration forming foci. LSGs are generally not collected longitudinally. Therefore, longitudinal studies of SS to investigate genetic events governing the onset and progression of autoimmunity would be greatly facilitated if "saliva DNA" (i.e., DNA isolated from saliva samples) could serve as a surrogate for salivary gland tissue samples.

The long-term goal of our research is to establish methods to facilitate early diagnosis and monitoring of SS progression that will lead to improved treatment and quality of life for SS patients.

Our central hypothesis is that the genomic methylation patterns of specific genes of saliva DNA will differ in SS patients compared to sicca patients, and these changes in saliva DNA are representative of methylation changes occurring in the salivary glands.

Our primary objective is to determine whether the saliva DNA can be used as a surrogate for salivary gland DNA to distinguish SS from sicca patients at the methylation level for genes relevant to SS.

Specific Aim 1: Determine genome-wide CpG methylation status of genes in saliva DNA from sicca and primary Sjögren's syndrome (pSS) patients.

Approach: We will analyze saliva DNA from 60 pSS and 60 sicca age-matched female patients, obtained at the time of initial classification based on ACR-EULAR criteria.

Reduced representation bisulfate sequencing (RRBS) will be used to determine the methylation status of CpG sites at the global level and of CpG dinucleotide sites located in the promoter region of genes: 1) involved in X-chromosome inactivation, 2) Matrix Metalloproteinase 9 (MMP9) pathogenesis pathway, 3) targeted by Epstein-Barr virus (EBV), 4) regulated by sex hormones, and 5) regulating the type I interferon response.

Statistical and computational meta-analysis methods will be used to determine the differentially methylated genes in saliva DNA, that can distinguish sicca from pSS patients per initial classification established with ACR-EULAR criteria, and are differentially expressed in salivary glands per existing publicly available metadata.

Specific Aim 2: Determine the extent to which differential methylation of gene subsets in saliva DNA can best distinguish pSS from sicca patients, taking into account the extent to which pSS patients show evidence of autoimmunity.

Approach: We will 1) establish Receiver Operating Characteristic (ROC) curves at the global level and for gene subsets and 2) determine whether more genes relevant to SS pathogenesis are affected in pSS patients with more prominent SS-related autoimmune laboratory findings.

Sjögren's syndrome (SS) is a chronic systemic autoimmune disease, mostly affecting women of menopausal age, leading to destruction of exocrine glands that can be exacerbated by infiltrating lymphocytes. Current classification for primary SS (pSS) follows the American College of Rheumatology-European League Against Rheumatism Classification Criteria (ACR-EULAR). These criteria are widely accepted including by the Sjögren's Syndrome Foundation and have been implemented by the Carolinas Center for Oral Health (CCOH) at Carolinas HealthCare System (CHS).

The classification of pSS relies on an ACR-EULAR consensus for the weighted determination of objective and subjective criteria conferring about 95% sensitivity and specificity. Objective criteria are based on pathology measurements including ocular staining tests [ocular staining score, van Bijsterveld test], the determination of tear production [Schirmer test], lymphocytic infiltration of labial salivary gland (LSG), presence of serum anti-SSA autoantibodies, and unstimulated salivary flow rate. Subjective criteria are based on the description of ocular and oral symptoms. Histopathological determination of lymphocytic infiltration yields a focus score (FS) that ranges from 0-12, with 12 corresponding to confluence of foci per 4 $mm^2$ surface area of a salivary gland section. The FS has been found to represent the most important classification variable, with the determination of anti-SSA autoantibodies ranked second in importance. Depending on the extent to which other ACR-EULAR criteria are met, a patient may be defined as a sicca patient if the FS is less than 1, while an FS equal or above 1 may correspond to a patient with SS.

Unfortunately, there are currently no biomarkers to determine with certainty that a person with a focus score of 0.9 is indeed a patient with SS while a patient with an FS of 1.1 is a sicca patient. Indeed, results from a longitudinal study conducted over two decades ago suggested that conversion of sicca patients to SS was associated with older age, higher serum IgG and beta-2-macroglobulin concentrations at baseline, and more frequent presence of anti-nuclear autoantibodies (ANA) at baseline. The question as to how conversion from sicca to SS might occur or whether direct disease-onset to SS occurs initially with discreet symptomatic and pathophysiological changes, remains unanswered.

Additionally, an X-chromosome dosage effect has been characterized for women with 47,XXX genotype (with two active X-chromosomes) compared to women with 46,XX genotype (one active X-chromosome). The study showed an approximate 2.9-fold and 2.5-fold higher prevalence in SS and SLE for the 47,XXX genotype, respectively. By analogy, a similar dosage effect could explain differences between SS and sicca female patients with 46,XX genotype. Indeed, LINE-1 retroelement and XIST are known to play a critical role in the maintenance of X-chromosome inactivation. XIST is a non-protein encoding gene exclusively expressed in 46,XX females from the inactivated X-chromosome, and its promoter contains one CpG dinucleotide island subject to differential methylation. The RNA expression of LINE-1 and XIST can both be induced by hypo-methylation. Both LINE-1 (able to induce type I interferon) and XIST are expressed at higher levels in salivary glands of pSS compared to sicca in female patients with 46,XX genotype. This difference potentially reflects an X-chromosome dosage effect due to partial alleviation of X-chromosome inactivation, relaxing normally silenced gene expression.

A few genome wide DNA methylation studies have been conducted on salivary glands of SS patients and white blood cells of SS and SLE patients. However, the potential impact of X-chromosome dosage effects due to partial alleviation of X-chromosome inactivation in relation to the development of autoimmunity has not yet been investigated. The proposed study will determine whether certain epigenomic methylation changes (global or gene specific) in saliva DNA, that are related to partial alleviation of X-chromosome inactivation (increased hypo-methylation) and/or skewed methylation of autosomes, can be used as a surrogate for changes in salivary gland tissue DNA in pSS patients.

We hypothesize that genes of saliva DNA will be differentially methylated in pSS compared to sicca patients. We further hypothesize that saliva DNA is impacted by epigenomic methylation changes similar to those occurring in salivary gland tissue DNA which can give rise to differential expression of genes involved in SS pathogenesis. We will address these hypotheses by conducting genome-wide RRBS of genes from saliva DNA and determining by meta-analysis of publicly available metadata the correspondence with the genes from salivary gland DNA regarding differential expression.

We also hypothesize that the extent of differential methylation of saliva DNA and the number of genes affected will increase for pSS patients with more prominent SS-related autoimmune findings (i.e., ANA, rheumatoid factor [RF], anti-SSA antibodies, and extent of lymphocytic infiltration). We will address this hypothesis by conducting ROC analyses for global methylation differences and subsets of genes in saliva DNA that are differentially methylated between sicca and pSS groups.

The preliminary data shown below suggest that lymphoid enhancer binding factor 1 (LEF1) encoding a transcription factor that can upregulate Matrix Metalloproteinase 9 (MMP9), is hypo-methylated in both DNA from salivary glands and saliva of pSS patients. Moreover, a study pertaining to psychiatric disorders tested whether saliva DNA could be used as a surrogate for brain DNA of various brain tissues. This study found that methylation patterns in saliva DNA were more similar to patterns in brain DNA than with those in blood DNA. In addition, increased levels of 8-OHdG, a marker of oxidative DNA damage, were found in the saliva of SS patients, but not in that of patients with other salivary gland dysfunction or of healthy individuals. This can reflect methylation changes in the oral cavity of SS patients.

Establishing a diagnosis closer to the onset of disease based on early biomarkers could lead to improved quality of life and provide a foundation for earlier monitoring or therapeutic intervention. There is no effective way of predicting SS risk, progression, or severity, thus making it impossible to develop strategies or new drugs to address hormone deficiencies or fluctuations that would be detrimental in pre-menopausal women before the disease develops. Longitudinal studies are needed to establish risk for autoimmunity in sicca patients and for lymphoma in SS patients, designed in the context of history of viral infection, i.e., infection of salivary glands and resident epithelial cells and B-cells in oral cavity by herpes viruses such as Epstein-Barr virus (EBV) or other viruses. Viral infection could influence gene expression or epigenomic changes contributing to autoimmunity.

This proposal is clinically relevant and specifically addresses the characterization of epigenomic sex-based regulation of autoimmune mechanisms which can potentially lead to immune reactivity and inflammation of the salivary and lacrimal glands in pSS compared to sicca female patients.

This research is innovative because we will, for the first time, 1) establish global and gene-specific methylation profiles of saliva DNA from age-matched female sicca and pSS patients, using genome-wide RRBS, and 2) determine by meta-analysis the correspondence with genes differentially expressed at the mRNA level and possibly differentially methylated in salivary glands of SS compared to sicca female patients. We will thus identify genes that are differentially methylated in saliva DNA, determined experimentally in this study, and those differentially expressed in salivary glands, determined by meta-analysis of existing datasets.

The goal will be to determine genes differentially methylated in saliva DNA that would also potentially be differentially expressed in salivary glands of pSS vs. sicca female patients. These genes would be differentially expressed in the direction expected for hyper- or hypo-methylation (potentially leading to under- or over-expression respectively). In future targeted studies, the panel of saliva DNA differentially methylated candidate genes identified here will be examined experimentally for methylation state and differential expression in LSG tissue and saliva of the same patients.

Knowledge which is lacking in the field of SS pathogenesis would greatly expand if our research shows that saliva DNA can be used as a surrogate for salivary gland DNA in longitudinal studies. Such longitudinal studies could then be designed based on an initial time point for salivary gland and saliva DNA analyses followed by time series analysis of saliva DNA alone. These studies could include the determination of hormonal effects and effects by EBV infection. In addition, saliva DNA methylation biomarkers might be identified that can determine which sicca patient is more likely to become a SS patient. Such conversion might occur after years if skewed methylation reaches a certain threshold affecting critical genes. These include genes subject to partial alleviation of X-chromosome inactivation, which can result in an X-chromosome dosage effect. Ultimately, identifying these changes would allow preventative measures improving quality of life that could be taken at an earlier stage of disease progression.

Overall, the proposed work will characterize the epigenomic methylation changes (global and gene-specific) in SS that might result from an intrinsic vulnerability of the salivary glands. Such vulnerability in combination with a history of viral infection, perhaps decades before SS symptoms become apparent, would lay the ground for autoimmunity and inflammation to develop and target salivary glands, particularly when pre-menopausal hormonal imbalance occurs.

We are in a strong position 1) to identify and delineate molecular pathways and cellular networks pertaining to sex-bias in SS, which mostly affects women, and 2) to determine how these pathways and networks influence disease onset, progression, persistence, and responses to treatment, based on proposed and downstream studies.

Specific Aim 1: Determine genome-wide CpG methylation status of genes in saliva DNA of sicca and primary Sjögren's syndrome (pSS) patients.

I.a. Introduction.

This specific aim will determine global and gene-specific methylation status of saliva DNA of female sicca patients (n=60) and age-matched female patients with primary Sjögren Syndrome (pSS; n=60), using saliva obtained at the time of initial ACR-EULAR classification. Genome-wide CpG methylation status will be obtained using RRBS method (Illumina). To establish the correspondence between DNA from saliva and DNA from salivary glands, we will also determine whether affected genes are differentially expressed in salivary glands of pSS compared to sicca patients, using publicly available expression data and published articles. Genes for which we find correspondence by meta-analysis may be confirmed for their methylation status or differential expression experimentally in LSGs in a future study, i.e., with hypo-methylation/hyper-methylation corresponding respectively to over-expression/under-expression in pSS vs. sicca patients.

Our primary objective is to determine whether prominent differences exist in global methylation patterns of DNA from saliva in sicca vs. pSS patients, and if so, whether these correspond to differences in methylation patterns of genes potentially relevant to SS pathogenesis, including the female-specific XIST gene, genes regulated by sex hormones, genes involved in MMP-9 pathway, and genes regulating the type I interferon response.

The primary objective will address the following sub-hypotheses: 1) more extensively aberrant methylation patterns in SS vs. sicca patients will correlate with overall higher XIST hypo-methylation, as well as with more genes being affected by these changes, whether these genes are encoded by the X-chromosome or by autosomes, and 2) there is increased alleviation of X-chromosome inactivation associated with global hypo-methylation in SS compared to sicca, therefore reflecting an X-chromosome dosage effect.

Our secondary objectives will be to: 1) determine the gene ontology (GO) at the level of biological processes, molecular pathways, and disease pathways for differentially methylated genes, (ii) identify the genes that can be regulated by sex hormones and/or are involved in autoimmunity and an inflammatory response.

The secondary objective will address the following sub-hypothesis: 1) we will identify differentially methylated genes specific to pSS vs. sicca and the associated molecular pathways that are potentially regulated by sex hormones, targeted by EBV, and/or involved in autoimmune processes.

I.b. Access to Biorepository.

Our laboratory has established a biorepository of saliva, LSG biopsies, serum, and PBMCs from sicca and pSS patients. We will be able to access saliva from sicca and pSS female patients to reach the sample size needed to implement this study.

I.c. Inclusion and Exclusion Criteria.

In this case-control study, case patients (pSS) and control patients (sicca) will fulfill the ACR-EULAR criteria. We will obtain stimulated saliva from age-matched women with sicca or pSS, who have a negative history of RA or SLE or other autoimmune diseases.

I.d. Experimental Design.

The design of this "case"-"control" study will be cross-sectional to investigate differences in methylation profiles (global and gene-specific) in saliva DNA of female pSS patients (n=60) compared to age-matched female sicca patients (n=60). The study involves experimental determination of saliva DNA methylation status at the genome level using RRBS method targeting CpG methylation sites.

I.e. Experimental Methods.

Saliva DNA extraction: Oragene™ Discover kit (DNA Genotek, Ottawa, Ontario, CAN) will be used following manufacturer's instructions. We routinely harvest good quality DNA in the range of 5 to 25 µg DNA/mL saliva.

Genome-wide CpG-specific RRBS: Using saliva DNA isolated with the Oragen™ Discover kit, we have successfully conducted methylation-specific qPCR (MS-qPCR) assays for lymphoid enhancer binding factor 1 (LEF1) (see FIG. 10). Saliva DNA, preserved and extracted using the Oragene™ Discover kit/PrepIt-L2P method, was purified by ethanol precipitation, bisulfite-converted, and used as a template for MS-qPCR with target MS-primers for LEF1. The same workflow will produce high quality DNA to be used for RRBS. RRBS involves sequential digestion of the genomic DNA by the restriction enzymes MspI and Taq$^{\alpha}$I, end-repair, adapter ligation, bisulfite conversion and PCR amplification, followed by next-generation sequencing to generate paired-end 36 base pairs (bp) sequencing reads (Illumina), thereby capturing the majority of the promoter regions. RRBS will be performed as described.

I.f. Proof of Concept Preliminary Data.

Figure 10:
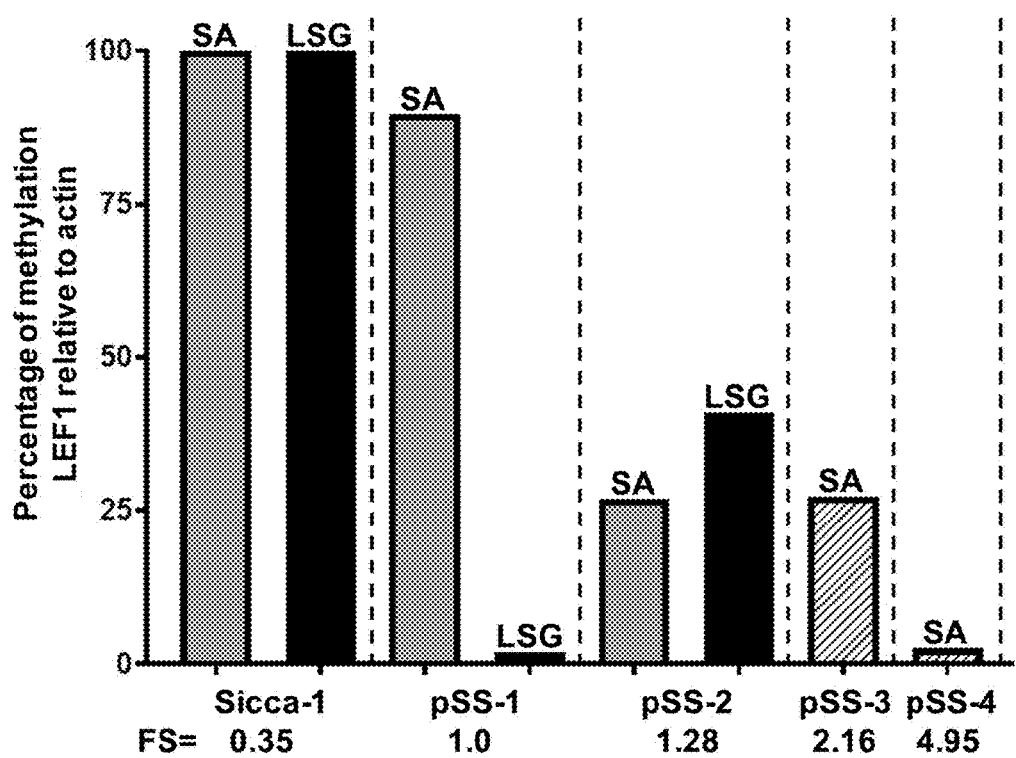
FIG. 10. LEF1 MS-qPCR assay of saliva and/or LSG of sicca (n=1) and pSS patients (n=4). DNA extracted from approximately 5 mg LSGs (RNeasy Midi kit, Qiagen, Valencia, Calif.) or 1 mL saliva (Oragen™ Discover kit, DNA Genotek, Ottawa, Ontario, CAN) was bisulfite modified with BisulFlash DNA Modification Kit (Epigentek, Farmingdale, N.Y., USA). Methylation-specific primer sequences for LEF1 genes were designed using Methprimer online program. MS-qPCR was performed using the Methylamp MS-qPCR Fast Kit (Epigentek, Farmingdale, N.Y., USA) per manufacturer's instructions. The specificity of MS-qPCR was confirmed by melt curve analysis and agarose gel electrophoresis. Saliva and LSG samples were analyzed for one sicca and two pSS female patients (Sicca-1, pSS-1, and pSS-2). Saliva alone was analyzed for pSS-3 and pSS-4 female pSS patients. SA: saliva; LSG: labial salivary gland; FS: focus score.

We have identified the LEF1 gene located on chromosome-4 with a promoter region rich in CpG islands, which encodes a transcription factor able to upregulate MMP9. In our meta-analysis, we found LEF1 mRNA differentially expressed, i.e., upregulated in salivary glands of pSS vs. sicca female patients, while not differentially expressed in PBMCs of same patient groups. We have successfully conducted MS-qPCR for LEF1 of saliva and/or salivary gland DNA of one sicca (Sicca-1, age 66) and four pSS female patients (pSS-1 to pSS-4, ages 35, 52, 58, 65, respectively) (FIG. 10).

The results show hypomethylation of LEF1 in saliva and LSGs of two pSS patients (pSS-1, pSS-2) and saliva of two pSS patients (pSS-3, pSS-4; no LSGs available), compared to the single control sicca patient (Sicca-1). Such hypomethylation could explain the increased LEF1 mRNA expression in LSGs of pSS patients identified by our meta-analysis. If confirmed with more samples, hypomethylation status of affected genes will suggest a systemic effect of unknown origin, since saliva DNA comes from various cellular sources. The differential methylation correspondence of saliva DNA vs. LSG DNA is not linear (FIG. 10) as various factors, including age, could impact saliva and each individual LSG to a variable extent. However, only a small sequence of 182 bp was interrogated by MS-qPCR with a single set of primers. RRBS, on the other hand, will provide DNA methylation status of all 7 CpG islands of LEF1 promoter. The 7 CpG islands encompass about 2530 bp total of the 4200 bp extended promoter region, where activators, repressors, or methyl-CpG-binding domain proteins (MBDs) can bind or not, depending on the methylation status.

Therefore, our approach will increase the likelihood of finding genome-wide correspondence and of identifying biomarkers with sufficient discriminatory power. With the larger sample size and broader technology proposed for this study, we might be able to identify candidate biomarkers potentially useful for diagnosis or predicting the rate of progression, by recursive partitioning. In addition, we have identified 51 genes upregulated in both LSGs and parotid salivary glands of pSS vs. sicca female patients, located on the X-chromosome and containing CpG island(s) in the promoter/distal promoter sequence. These identified genes have the potential to be differentially methylated and/or upregulated by a transcription factor over-expressed due to hypo-methylation and represent gene ontology descriptions such as "positive regulation of interferon-alpha and gamma biosynthetic processes" and "toll-like receptor 7 signaling pathway." These genes include XIST, which contains one CpG island in its promoter region and found to be over-expressed by at least 4-fold in LSGs and parotid glands of pSS vs. sicca female patients per our meta-analysis. Importantly, we have also built an interactive database to identify additional biomarkers based on the integration of novel datasets. Moreover, 13 of the 51 X-chromosome encoded genes can potentially be upregulated by LEF1, based on our own assessment of LEF1 binding sites in the promoter region of the genes identified in our meta-analysis.

Specific Aim 2: Determine the extent to which differential methylation of gene subsets in saliva DNA can best distinguish pSS from sicca patients, taking into account the extent to which pSS patients show evidence of autoimmunity.

II.a. Introduction.

This specific aim corresponds to an extensive statistical analysis that will determine whether there are subsets of differentially methylated genes, which differentiate sicca from pSS patients, depending on initial overall ACR-EULAR classification or the presence or levels of markers of autoimmunity found by laboratory tests (i.e., ANA, RF, anti-SSA antibodies, and lymphocytic infiltration).

Our primary objective is to identify a subset of genes that are the most discriminatory when comparing sicca to pSS, based on the initial classification following the ACR-EULAR criteria.

The primary objective will address the following sub-hypothesis: there will be a subset of differentially methylated genes, which in combination clearly segregate sicca from pSS patients with a sensitivity and specificity ≥80%.

Our secondary objective is to identify genes that would be more discriminatory if markers of autoimmunity are more prominent in pSS patients.

The secondary objective will address the following sub-hypothesis: there are differentially methylated genes that are associated with higher ANA, RF, or anti-SSA antibodies levels, or higher focus score.

III. Sample Size Determination and Statistical Analysis for Specific Aims 1-2.

IIIa. Sample Size Determination.

In exemplary studies, we will perform the statistical analyses on methylation data of saliva DNA from about 60 female sicca patients with focus scores ≤1 and about 60 female pSS patients with focus scores ≥1. We will attempt to identify single gene and a global gene methylation signatures that can accurately discriminate sicca subjects from those with SS. Based on a two-sided alpha=0.05 significance level, the proposed sample size will provide more than 90% power to statistically exclude an area under the receiver operating characteristic (ROC) curve of 0.70 (null hypothesis), assuming the true area under the curve (AUC) is 0.85 (alternative hypothesis).

IIIb. Bioinformatics and Statistical Analyses.

BS-Seeker2 software will be used to align RRBS sequence reads from each sample to the human reference genome. Global cytosine methylation level, chromosome-wide cytosine methylation level, genomic elements (such as promoter, gene body, exon, intron and intergenic non-coding region) cytosine methylation level, as well as individual cytosine methylation level from each sample will be calculated using MethGo software. Logistic regression will be used to compare cytosine methylation levels at different scales in SS vs. sicca patients while controlling for the influence of covariates. Significantly differentially methylated sites/regions with Benjamini-Hochberg corrected p-values less than 0.01 will be included in a subsequent multi-variate regression with backward selection to construct a parsimonious model.

Subsequently, ROC curves will be used to test the predictive properties of the developed parsimonious regression model as well as for the individual genes exhibiting differences in methylation levels. This will be accomplished by calculating the AUC of the ROC curve based on the trapezoidal approximation method. In addition, when sicca and pSS patients are compared, genes having significant differences in methylation levels will be subjected to molecular network analysis using Ingenuity Pathway Analysis software (Qiagen) to search for most over-represented biological terms and canonical pathways.

Correlation between saliva DNA methylation data generated in this study and mRNA expression metadata of salivary glands, PBMCs or B-cells from pSS-related studies will be determined by concept profile analysis (CPA)-assisted genetic meta-analysis. To perform CPA text mining, the web-based service 'pubmed2ensembl' will be used. Since saliva DNA can originate from oral mucosa epithelial cells, fibroblasts and white blood cells, metadata from PBMCs or B-cell subset of sicca and pSS patients will be used to identify differentially expressed genes possibly differentially methylated and likely to be more relevant to pSS salivary glands tissue (acinar or ductal cells) rather than lymphocytic infiltrates.

Genes that are differentially methylated in saliva DNA (determined experimentally in this study) and differentially expressed in salivary gland (determined by meta-analysis in this study) will be subjected to molecular network analysis. These genes may be differentially expressed in at least two gene expression datasets of salivary glands of sicca vs. pSS datasets of female patients (≥1.5-fold change) available in the web application NCBI-GEO2R (i.e., cross-sectional studies GSE23117, GSE40611, GSE40568). We may also use additional datasets that may be released on public database, including pSS methylation datasets obtained by collaboration or by request to authors. Secondarily, differentially-methylated genes that might not be differentially expressed at the mRNA level due to possible temporal feed-back regulations will also be subject to molecular network analysis. Gene ontology and molecular network analyses will be performed using Ingenuity Pathway Analysis (Qiagen) and Gene Ontology (GO) biological processes and the Kyoto Encyclopedia of Genes and Genomes (KEGG; pathways functional analysis module in Gene-Codis). To identify functional associations within the enriched subset of genes, the "Search Tool for the Retrieval of Interacting Genes/Proteins-database" (STRING-db) server will be utilized. To expand on our functional network and to provide complementary connections within and between gene clusters, we will include the major SNP-containing candidate genes associated with SS disease susceptibility identified in two independent genome-wide association studies.

V. Enrollment Timeline, Data Collection and Data Management.

Data management for the proposed SS epigenomic study will be conducted by the Sjögren's Study Team (SST) at CHS-CCOH. The SST responsibilities include: (1) secure, web-based data collection for pSS ("cases") and sicca ("controls") patients, (2) secure repository of epigenomic data, and (3) transfer of de-identified data to biostatisticians for statistical analyses addressing Specific Aims 1 and 2. The SST will use the sicca case report forms (CRFs) to structure a web-based data entry system for "cases" and "controls" using Research Electronic Data Capture (REDCap) data management system. REDCap is a secure, 21CFR11 compliant, web-based application designed with the flexibility to support data capture for a variety of research studies. Clinical data will be directly entered or entered from CRFs into REDCap. De-identified clinical data will be merged with epigenomic data by the CHS biostatisticians.

In further studies, we will validate our candidate genes by confirming that genes that are differentially methylated in saliva DNA and likely differentially expressed in salivary glands are indeed differentially expressed and methylated in salivary glands. To this end, we will use LSG biopsies available in our biorepository. We will then determine whether the candidate genes consistently distinguish sicca from pSS patients based on saliva DNA methylation patterns using a larger cohort. Further, we will be able to design a longitudinal study to determine if from the time of initial classification, DNA methylation abnormalities of saliva DNA amplify (i.e., affect more corresponding genes that may be differentially expressed) with the development of more severe or rapid pSS progression or, alternatively, with the conversion from sicca to pSS.

The foregoing is illustrative of the present invention, and is not to be construed as limiting thereof. The invention is defined by the following claims, with equivalents of the claims to be included therein.

All publications, patent applications, patents and other references cited herein are incorporated by reference in their entireties for the teachings relevant to the sentence and/or paragraph in which the reference is presented.

TABLE 1

Gene sets used in meta-analysis
Gene sets with their corresponding disease are listed by GEO accession numbers. For all gene sets, total number of patients, both diseased and control and their tissue types are listed.

| Disease | GEO accession | Female patients | Female controls | Tissue type |
| --- | --- | --- | --- | --- |
| SS | GSE48378 | 11 | 16 | PBMC |
| SLE | GSE10325 | 14 | 11 | PBMCs ($CD4^+$ T-cells/$CD19^+$ B-cells) |
| RA | GSE15573 | 14 | 10 | PBMC |
| SS | GSE23117 | 10 | 5 | minor SG |
| SS | GSE40611 | 17 | 12 | Parotid |
| SS | GSE40568 | 5 | 3 | LSG |
| SLE | GSE36700 | 4 | 2 | Synovial biopsy |
| RA | GSE7669 | 5 | 4 | Synovial fibroblast |

TABLE 2

Summary of DE genes in at least 2 out of 3 SS salivary gland microarray datasets displayed alphabetically with any previously known associations in SS (listed as a PMID). The genes with shaded grey color are never shown to be associated with SS pathogenesis before. Yellow background represents DE of that gene in a particular dataset (FC ≤ −1.5 or FC ≥ +1.5).

| Entrez Gene ID | Gene symbol | Gene Name | Chromosome Location | minor | parotid | LSG | Avg. | up/down | effect in SS | PMID |
|---|---|---|---|---|---|---|---|---|---|---|
| 19 | ABCA1 | ATP binding cassette subfamily A member 1 | 9q31 | 2.689927 | 2.337204 | 1.750783 | 2.259305 | ↑ | + | 11355874 |
| 199 | AIF1 | allograft inflammatory factor 1 | 6p21.3 | 2.866642 | 5.018468 | 1 | 2.961703 | ↑ | + | 23116360 |
| 9447 | AIM2 | absent in melanoma 2 | 1q22 | 7.172801 | 2.783889 | 1.30586 | 3.754183 | ↑ | + | 24367371 |
| 6790 | AURKA | aurora kinase A | 17p13.3 | 2.078927 | 2.197617 | 1 | 1.758848 | ↑ | ? | NA |
| 489 | ATP2A3 | ATPase, Ca++ transporting, ubiquitous | 20q13 | −3.20324 | −1.5659 | 1.308578 | −1.15352 | | ? | NA |
| 762 | CA4 | carbonic anhydrase IV | 17q23.1 | −4.47136 | −1.86331 | −1 | −2.44489 | | ? | 15647194 |
| 811 | CALR | calreticulin | 19p13.13 | −6.11361 | −1.63341 | 1.0329 | −2.23804 | | − | 12974767 |
| 1230 | CCR1 | chemokine (C-C motif) receptor 1 | 3p21 | 3.652078 | 2.565868 | 2.188587 | 2.802178 | ↑ | + (cell line) | 22157716 |
| 9332 | CD163 | CD163 molecule | 12p13 | 1.841051 | 5.084738 | 2.188587 | 3.038126 | ↑ | ? | NA |
| 911 | CD1C | CD1c molecule | 1q23.1 | 2.422864 | 3.764724 | 0.751581 | 2.313056 | ↑ | + | 24909310 |
| 912 | CD1D | CD1d molecule | 1q23.1 | 6.868012 | 5.833722 | 1.007514 | 4.569749 | ↑ | + | 24909310 |
| 919 | CD247 | CD247 molecule | 1q24.2 | 6.862843 | 2.081525 | 1.183451 | 3.37594 | ↑ | ? | 12100036 |
| 952 | CD38 | CD38 molecule | 4p15.32 | 1.56004 | 4.195971 | 2.42839 | 2.728134 | ↑ | ? | 16802367 |
| 969 | CD69 | CD69 molecule | 12p13 | 9.411246 | 5.707685 | 1.376496 | 5.498476 | ↑ | + | 15880807 |
| 972 | CD74 | CD74 molecule, major histocompatibility complex, class II invariant chain | 5q32 | 3.909211 | 2.287277 | 1 | 2.398829 | ↑ | ? | NA |
| 925 | CD8A | CD8a molecule | 2p12 | 3.248257 | 3.173308 | 1.793776 | 2.738447 | ↑ | ? | 24022789 |
| 1066 | CES1 | carboxylesterase 1 | 16q22.2 | −6.55566 | −2.48669 | −3.70635 | −4.24957 | | ? | NA |
| 8837 | CFLAR | CASP8 and FADD like apoptosis regulator | 2q33-q34 | 6.860175 | −1.68777 | 1.85961 | 2.344005 | ↑ | + | 26686423 |
| 1111 | CHEK1 | checkpoint kinase 1 | 11q24.2 | 2.457989 | 2.452342 | 1 | 1.97011 | ↑ | ? | NA |
| 170482 | CLEC4C | C-type lectin domain family 4 member C | 12p13.2-p12.3 | 3.138769 | 1.975827 | 1 | 2.038199 | ↑ | ? | NA |
| 1285 | COL4A3 | collagen, type IV, alpha 3 (Goodpasture antigen) | 2q36-q37 | 4.951697 | 2.407615 | 1.465101 | 2.941471 | ↑ | ? | NA |
| 1289 | COL5A1 | collagen, type V, alpha 1 | 9q34.2-q34.3 | −1.55876 | −1.65454 | 1.097332 | −0.70532 | | ? | NA |
| 3627 | CXCL10 | chemokine (C—X—C motif) ligand 10 | 4q21 | 15.53766 | 4.662412 | 4.958831 | 8.386301 | ↑ | + | 22703193 |
| 10563 | CXCL13 | chemokine (C—X—C motif) ligand 13 | 4q21 | 44.71058 | 60.97522 | 2.378414 | 36.02141 | ↑ | + | 15880807 |
| 6374 | CXCL5 | chemokine (C—X—C motif) ligand 5 | 4q13.3 | −2.22093 | −2.08968 | −1.49278 | −1.93446 | | ? | NA |
| 2833 | CXCR3 | chemokine (C—X—C motif) receptor 3 | Xq13 | 3.059138 | 1.986979 | 1 | 2.015372 | ↑ | + | 16456020 |
| 643 | CXCR5 | chemokine (C—X—C motif) receptor 5 | 11q23.3 | 1.941557 | 2.158527 | 1 | 1.700028 | ↑ | + | 11967114 |
| 10663 | CXCR6 | chemokine (C—X—C motif) receptor 6 | 3p21 | 4.240655 | 2.479398 | 1 | 2.573351 | ↑ | ? | NA |
| 23586 | DDX58 | DEAD (Asp-Glu-Ala-Asp) box polypeptide 58 | 9p12 | 1.859255 | 1.827011 | 2.114036 | 1.933434 | ↑ | + | 26137972 |
| 953 | ENTPD1 | ectonucleoside triphosphate diphosphohydrolase 1 | 10q24.1 | 3.264319 | 2.26383 | 1.063338 | 2.197162 | ↑ | + | 23116360 |
| 2113 | ETS1 | v-ets avian erythroblastosis virus E26 oncogene homolog 1 | 11q23.3 | 3.355655 | 3.453734 | 2.042024 | 2.950471 | ↑ | (+/?) | NA |
| 355 | FAS | Fas cell surface death receptor | 10q24.1 | 4.672032 | 3.301341 | 1.692317 | 3.221897 | ↑ | + | 14672901 |
| 2217 | FCGRT | Fcfragment of IgG, receptor, transporter, alpha | 17q25 | −2.24004 | −1.57099 | 1 | −1.60368 | | + | 22117835 |
| 2952 | GSTT1 | Glutathion S-Transferase Theta 1 | 19q13.3 | −4.79501 | −2.35219 | −1 | −2.71573 | | − | 10616008 |
| 3126 | HLA-DRB4 | Major Histocompatibility Complex, Class II, DR Beta 4 | 22q11.23 | 2.17863 | 3.135402 | 1.382232 | 2.232088 | ↑ | + | 8173843 |
| 3429 | IFI27 | Interferon, alpha-Inducible protein 27 | 6p21.3 | 2.210521 | 2.306114 | 8.456144 | 4.32426 | ↑ | + | 21078725 |
| 10561 | IFI44 | interferon induced protein 44 | 14q32.12 | 2.264457 | 3.824521 | 9.253505 | 5.114161 | ↑ | + | 21078725 |
| 64135 | IFIH1 | interferon induced, with helicase C domain 1 | 1p31.1 | 2.15125 | 2.18539 | 3.810552 | 2.715731 | ↑ | + | 26137972 |
| 3434 | IFIT1 | Interferon induced protein with tetratricopeptide repeats 1 | 2q24.2 | 1.422265 | 6.117067 | 7.012846 | 4.859102 | ↑ | + | 23116360 |
| 3437 | IFIT3 | interferon induced protein with tetratricopeptide repeats 3 | 10q23.31 | 2.573189 | 1.843917 | 7.160201 | 3.859102 | ↑ | + | 18581327 |
| 8519 | IFITM1 | interferon induced transmembrane protein 1 | 11p15.5 | 1.768001 | 2.893433 | 2.313376 | 2.324973 | ↑ | + | 22703193 |
| 3458 | IFNG | interferon, gamma | 12q14 | 6.977488 | 2.80953 | 1.108801 | 3.63194 | ↑ | + | 15584966 |
| 3560 | IL2RB | interleukin 2 receptor subunit beta | 22q13 | 4.636068 | 3.379194 | 1.812524 | 3.275929 | ↑ | ? | NA |
| 3688 | ITGB1 | integrin subunit beta 1 | 22q13 | 3.422982 | 3.216434 | 3.09513 | 3.244849 | ↑ | ? | NA |

TABLE 2-continued

Summary of DE genes in at least 2 out of 3 SS salivary gland microarray datasets displayed alphabetically with any previously known associations in SS (listed as a PMID). The genes with shaded grey color are never shown to be associated with SS pathogenesis before. Yellow background represents DE of that gene in a particular dataset (FC ≤ −1.5 or FC ≥ +1.5).

| Entrez Gene ID | Gene symbol | Gene Name | Chromosome Location | minor | parotid | LSG | Avg. | up/down | effect in SS | PMID |
|---|---|---|---|---|---|---|---|---|---|---|
| 3821 | KLRC1 | killer cell lectin-like receptor subfamily C, member 1 | 10p11.2 | 2.16112 | 2.817828 | 1 | 1.992983 | ↑ | ? | 15880807 |
| 3902 | LAG3 | lymphocyte-activation gene 3 | 12p13 | 2.822296 | 2.740417 | 0.998213 | 2.186975 | ↑ | + | 27180164 |
| 27074 | LAMP3 | lysosomal-associated membrane protein 3 | 12p13.3 | 4.210236 | 3.332297 | 4 | 3.847511 | ↑ | + | N/A |
| 3949 | LDLR | low density lipoprotein receptor | 3q26.3-q27 | −2.581 | −2.71773 | 1.754427 | −1.18143 | | ? | NA |
| 51176 | LEF1 | lymphoid enhancer-binding factor 1 | 19p13.2 | 3.763471 | 2.280225 | 1.105731 | 2.383142 | ↑ | (+/?) | NA |
| 23643 | LY96 | lymphocyte antigen 96 | 4q25 | 4.281584 | 1.513034 | 1.28076 | 2.358459 | ↑ | + | 24286337 |
| 5606 | MAP2K3 | mitogen-activated protein kinase kinase 3 | 8q13.3 | −2.47152 | −2.0275 | 1.231144 | −1.08929 | | ? | NA |
| 4288 | MKI67 | marker of proliferation KI-67 | 17q11.2 | 2.102941 | 3.151341 | 1 | 2.084761 | ↑ | ? | NA |
| 4318 | MMP9 | matrix metallopeptidase 9 | 10q26.2 | 11.12764 | 4.761428 | 1.48144 | 5.790168 | ↑ | + | 16142742 |
| 931 | MS4A1 | membrane-spanning 4-domains, subfamily A, member 1 | 20q13.12 | 55.68562 | 41.68337 | 1.327765 | 32.89892 | ↑ | + | 2551310 |
| 4582 | MUC1 | mucin 1, cell surface associated | 11q12.2 | −3.01684 | −2.77978 | 1.729074 | −1.35585 | | + | 9634933 |
| 4599 | MX1 | MX dynamin-like GTPase 1 | 11q12-q13 | 1.236122 | 4.969572 | 6.588728 | 4.264807 | ↑ | + | 21078725 |
| 4938 | OAS1 | 2′-5′-oligoadenylate synthetase 1 | 1q22 | 2.595891 | 2.780575 | 3.530812 | 2.969092 | ↑ | + | 21078725 |
| 4939 | OAS2 | 2′-5′-oligoadenylate synthetase 2 | 21q22.3 | 1.861661 | 2.234033 | 2.928171 | 2.341288 | ↑ | + | 22703193 |
| 5087 | PBX1 | pre-B-cell leukemia homeobox 1 | 12q24.2 | −3.24645 | −1.61241 | 1.633538 | −1.07511 | | ? | NA |
| 5724 | PTAFR | platelet-activating factor receptor | 1q24.2 | 1.661967 | 2.111542 | 1 | 1.59117 | ↑ | + | 22117835 |
| 5740 | PTGIS | prostaglandin I2 (prostacyclin) synthase | 20q23.3 | −1.82817 | −2.24376 | −1 | −1.69064 | | ? | NA |
| 5888 | RAD51 | RAD51 recombinase | 15p35-p34.3 | 3.549316 | 2.113271 | 1 | 2.220862 | ↑ | ? | NA |
| 6241 | RRM2 | ribonucleotide reductase M2 | 20q13 | 4.121913 | 6.043606 | 1.465101 | 3.876873 | ↑ | + | 23129761 |
| 6279 | S100A8 | S100 calcium binding protein A8 | 15q15.1 | 2.098479 | 2.670309 | 1 | 1.922929 | ↑ | + | 22117835 |
| 6280 | S100A9 | S100 calcium binding protein A9 | 2p25-p24 | 2.469122 | 1.551355 | 0.833931 | 1.618136 | ↑ | + | 22117835 |
| 6614 | SIGLEC1 | sialic acid binding Ig-like lectin 1, sialoadhesin | 1q12-q22 | 2.781066 | 3.056143 | 1.052193 | 2.296468 | ↑ | + | 23831963 |
| 6571 | SLC18A2 | solute carrier family 18 (vesicular monoamine transporter), member 2 | 1q21 | 1.882473 | 1.579413 | 1 | 1.487295 | ↑ | ? | NA |
| 6662 | SOX9 | SRY-box 9 | 20p13 | −1.74609 | −1.58715 | 1.638073 | −0.56506 | | ? | NA |
| 6772 | STAT1 | signal transducer and activator of transcription 1 | 10q25 | 7.261337 | 4.040552 | 9.646463 | 6.982784 | ↑ | + | 23116360 |
| 6773 | STAT2 | signal transducer and activator of transcription 2 | 17q24.3 | 2.363338 | 1.866609 | 2.514027 | 2.247991 | ↑ | ? | NA |
| 6869 | TACR1 | tachykinin receptor 1 | 2q32.2-q32.3 | −3.13003 | −2.12407 | −1 | −2.0847 | | ? | NA |
| 6890 | TAP1 | transporter 1, ATP-binding cassette, sub-family B (MDR/TAP) | 12q13.2 | 3.710115 | 2.712941 | 2.828427 | 3.083828 | ↑ | + | 9324024 |
| 51284 | TLR7 | toll-like receptor 7 | 2p13.1-p12 | 4.696262 | 3.739536 | 1.614402 | 3.350067 | ↑ | + | 23116360 |
| 7148 | TNXB | tenascin XB | 6p21.3 | −2.6391 | −1.79952 | −1 | −1.81287 | | ? | NA |
| 7253 | TSHR | thyroid stimulating hormone receptor | 22q12.2 | 5.917943 | 1.624959 | 1 | 2.847634 | ↑ | ? | NA |
| 7351 | UCP2 | uncoupling protein 2 (mitochondrial, proton carrier) | Xp22.3 | 2.099967 | 2.385967 | 1.162314 | 1.882749 | ↑ | ? | 11947921 |

TABLE 3

Gene enrichment pathway analysis using GeneCodis: 76 DE genes from table 2 were grouped based on gene ontology.

| Genes | NGR | TNGR | NG | TNG | Hyp | Hyp* | Annotations |
|---|---|---|---|---|---|---|---|
| 15 genes | 181 | 34208 | 15 | 76 | 8.47587e−20 | 5.95006e−17 | GO: 0019221: cytokine-mediated signaling pathway (BP) |
| 14 genes | 382 | 34208 | 14 | 76 | 1.35832e−13 | 4.76772e−11 | GO: 0006955: immune response (BP) |
| 8 genes | 75 | 34208 | 8 | 76 | 6.08085e−12 | 1.42292e−09 | GO: 0060337: type I interferon-mediated signaling pathway (BP) |
| 11 genes | 259 | 34208 | 11 | 76 | 1.40564e−11 | 2.46689e−09 | GO: 0006954: inflammatory response (BP) |
| 9 genes | 171 | 34208 | 9 | 76 | 1.68561e−10 | 2.36659e−08 | GO: 0007166: cell surface receptor signaling pathway (BP) |
| 8 genes | 126 | 34208 | 8 | 76 | 4.13608e−10 | 4.83921e−08 | GO: 0006935: chemotaxis (BP) |
| 8 genes | 136 | 34208 | 8 | 76 | 7.61429e−10 | 7.63604e−08 | GO: 0032496: response to lipopolysaccharide (BP) |
| 5 genes | 51 | 34208 | 5 | 76 | 1.02701e−07 | 9.01203e−06 | GO: 0071260: cellular response to mechanical stimulus (BP) |
| 9 genes | 361 | 34208 | 9 | 76 | 1.12401e−07 | 8.76728e−06 | GO: 0008284: positive regulation of cell proliferation (BP) |
| 5 genes | 54 | 34208 | 5 | 76 | 1.3755e−07 | 9.656e−06 | GO: 0019882: antigen processing and presentation (BP) |
| 3 genes | 7 | 34208 | 3 | 76 | 3.66477e−07 | 2.33879e−05 | GO: 0002544: chronic inflammatory response (BP) |
| 8 genes | 309 | 34208 | 8 | 76 | 4.48142e−07 | 2.62163e−05 | GO: 0045087: innate immune response (BP) |
| 6 genes | 144 | 34208 | 6 | 76 | 8.59636e−07 | 4.64203e−05 | GO: 0009615: response to virus (BP) |
| 5 genes | 82 | 34208 | 5 | 76 | 1.13067e−06 | 5.66952e−05 | GO: 0060333: interferon-gamma-mediated signaling pathway (BP) |
| 5 genes | 89 | 34208 | 5 | 76 | 1.69935e−06 | 7.95296e−05 | GO: 0032355: response to estradiol stimulus (BP) |
| 13 genes | 1176 | 34208 | 13 | 76 | 1.79419e−06 | 7.872e−05 | GO: 0007165: signal transduction (BP) |

TABLE 4

KEGG pathways associated with diseases using GeneCodis: List of diseases associated with the 76 genes listed in table 2 from KEGG analysis showing their association with individual disease.

| Id | Items | Disease | Support | List size | Hyp | Hyp_c | Genes |
|---|---|---|---|---|---|---|---|
| 28 | Kegg: 05162 | Measles | 12 | 76 | 1.36E−16 | 1.25E−14 | STAT1, STAT2, OAS2, MX1, FAS, IFNG, DDX58, IL2RB, OAS1, IFIH1, TACR1, TLR7 |
| 1 | Kegg: 05160 | Hepatitis C | 7 | 76 | 2.00E−08 | 4.61E−07 | STAT1, STAT2, OAS2, IFIT1, DDX58, OAS1, LDLR |
| 20 | Kegg: 05145 | Toxoplasmosis | 6 | 76 | 3.40E−07 | 5.21E−06 | STAT1, MAP2K3, IFNG, LY96, ITGB1, LDLR |
| 74 | Kegg: 05142 | Chagas disease (American trypanosomiasis) | 5 | 76 | 3.33E−06 | 3.41E−05 | FAS, IFNG, CALR, CD247, CFLAR |
| 38 | Kegg: 05152 | Tuberculosis | 3 | 76 | 0.00671216 | 0.0205839 | STAT1, CD74, IFNG |
| 70 | Kegg: 05140 | Leishmaniasis | 3 | 76 | 0.000436047 | 0.0026744 | STAT1, IFNG, ITGB1 |
| 84 | Kegg: 05146 | Amoebiasis | 3 | 76 | 0.00154506 | 0.0071073 | IFNG, CD1D, COL5A1 |
| 89 | Kegg: 05332 | Graft-versus-host disease | 3 | 76 | 4.10E−05 | 0.0003427 | KLRC1, FAS, IFNG |
| 39 | Kegg: 05320 | Autoimmune thyroid disease | 2 | 76 | 0.0045332 | 0.0148948 | FAS, TSHR |
| 41 | Kegg: 05143 | African trypanosomiasis | 2 | 76 | 0.0024597 | 0.0098388 | FAS, IFNG |
| 45 | Kegg: 05412 | Arrhythmogenic right ventricular cardiomyopathy (ARVC) | 2 | 76 | 0.0115612 | 0.0322313 | LEF1, ITGB1 |
| 51 | Kegg: 05130 | Pathogenic Escherichia coli infection | 2 | 76 | 0.0064686 | 0.0205211 | LY96, ITGB1 |
| 62 | Kegg: 04940 | Type I diabetes mellitus | 2 | 76 | 0.00260968 | 0.0100038 | FAS, IFNG |
| 67 | Kegg: 05323 | Rheumatoid arthritis | 2 | 76 | 0.0150972 | 0.0408512 | CXCL5, IFNG |
| 76 | Kegg: 05212 | Pancreatic cancer | 2 | 76 | 0.0106698 | 0.0306756 | STAT1, RAD51 |

TABLE 5

Table showing SS PBMC genes (≥+1.5 FC) in common with both SS and SLE genes (1849) identified by CPA analysis and their respective FC values in three independent SS salivary gland and one SLE synovial biopsy data sets.

| upregulated in PBMCs of SS female patients common in | minor SG | | | paroid gland | | | LSG | | | Sy SLE | | | PBMC (SS) | | |
|---|---|---|---|---|---|---|---|---|---|---|---|---|---|---|---|
| SS and SLE (ANNI) | logFC | FC | FC(−) | logFC | FC | FC(−) | logFC | FC | FC(−) | logFC | FC | FC(−) | logFC | FC | FC(−) |
| AHR | 1.293472 | 2.451172 | −0.40797 | 0.350933 | 1.275385 | −0.78408 | 8.84E−01 | 1.845485 | −0.54186 | 0.369697 | 1.292081 | −0.77395 | 0.596923 | 1.512487 | −0.66116 |
| B3GAT1 | 1.155199 | 2.22715 | −0.449 | 0.088307 | 1.063122 | −0.94063 | −2.33E−09 | 1 | −1 | −2.20393 | 0.217045 | −4.60733 | 0.808526 | 1.751421 | −0.57097 |
| CCL2 | 0.105594 | 1.075937 | −0.92942 | −0.10069 | 0.466294 | −2.14457 | 3.61E−01 | 1.284316 | −0.77862 | 0.348428 | 1.273173 | −0.78544 | 0.742407 | 1.672965 | −0.59774 |
| CCL8 | 1.370762 | 2.586071 | −0.38669 | 0.564491 | 1.478865 | −0.67619 | 4.59E−01 | 1.374589 | −0.72729 | 1.353824 | 2.555886 | −0.39125 | 0.831137 | 1.779087 | −0.56209 |
| CD163 | 0.88053 | 1.841051 | −0.54317 | 2.346174 | 5.084738 | −0.19667 | 1.13 | 2.188587 | −0.45692 | 1.797375 | 3.475871 | −0.2877 | 0.796936 | 1.737407 | −0.57557 |
| CD38 | 0.641583 | 1.56004 | −0.64101 | 2.069005 | 4.195971 | −0.23832 | 1.28 | 2.42839 | −0.4118 | 2.363262 | 5.145323 | −0.19435 | 0.598243 | 1.513872 | −0.66056 |
| CD69 | 3.234386 | 9.411246 | −0.10626 | 2.512906 | 5.707685 | −0.1752 | 4.61E−01 | 1.376496 | −0.72648 | 1.095798 | 2.137313 | −0.46788 | 0.608239 | 1.524397 | −0.656 |
| CES1 | −2.71274 | 0.15254 | −6.55566 | −1.31423 | 0.402141 | −2.48669 | −1.89 | 0.269807 | −3.70635 | 1.124406 | 2.180118 | −0.45869 | 0.70906 | 1.634739 | −0.61172 |
| CTSG | −0.85747 | 0.551919 | −1.81186 | −0.30351 | 0.810277 | −1.23415 | −3.96E−01 | 0.759962 | −1.31585 | 0.019608 | 1.013684 | −0.9865 | 0.669303 | 1.590305 | −0.62881 |
| CXCL10 | 3.957697 | 15.53766 | −0.06436 | 2.221076 | 4.662412 | −0.21448 | 2.31 | 4.958831 | −0.20166 | 3.543853 | 11.66289 | −0.08574 | 1.442095 | 2.711152 | −0.36803 |
| DDX58 | 0.894724 | 1.859255 | −0.53785 | 0.869485 | 1.827011 | −0.54734 | 1.08 | 2.114036 | −0.47303 | 1.337194 | 2.526594 | −0.39579 | 0.6832 | 1.605697 | −0.62278 |
| EIF2AK2 | 0.425221 | 1.342778 | −0.74472 | −0.15573 | 0.89768 | −1.11398 | 2.09 | 4.257481 | −0.23488 | 1.251078 | 2.380192 | −0.42013 | 0.684943 | 1.607639 | −0.62203 |
| FCGR1A | −0.86712 | 0.54824 | −1.82402 | 0.488746 | 1.403224 | −0.71264 | −8.00E−10 | 1 | −1 | 1.313758 | 2.485882 | −0.40227 | 0.604452 | 1.520401 | −0.65772 |
| HESX1 | 0.946529 | 1.92723 | −0.51888 | −0.01665 | 0.988524 | −1.01161 | −2.67E−10 | 1 | −1 | 0.869998 | 1.82766 | −0.54715 | 0.713215 | 1.639454 | −0.60996 |
| IFI27 | 1.144387 | 2.210521 | −0.45238 | 1.205464 | 2.306114 | −0.43363 | 3.08 | 8.456144 | −0.11826 | 1.659594 | 3.159275 | −0.31653 | 2.587592 | 6.010947 | −0.16636 |
| IFI44 | 1.179165 | 2.264457 | −0.44161 | 1.935279 | 3.824521 | −0.26147 | 3.21 | 9.253505 | −0.10807 | 0.673944 | 1.595429 | −0.62679 | 1.5706 | 2.970282 | −0.33667 |
| IFIH1 | 1.105175 | 2.15125 | −0.46485 | 1.127891 | 2.18539 | −0.45758 | 1.93 | 3.810552 | −0.26243 | 1.881265 | 3.683978 | −0.27145 | 0.758192 | 1.691389 | −0.59124 |
| IFIT1 | 0.50819 | 1.422265 | −0.7031 | 2.61284 | 6.117067 | −0.16348 | 2.81 | 7.012846 | −0.1426 | 1.193586 | 2.287206 | −0.43721 | 1.323509 | 2.502741 | −0.39956 |
| IFIT3 | 1.363558 | 2.573189 | −0.38862 | 0.882774 | 1.843917 | −0.54232 | 2.84 | 7.160201 | −0.13966 | 1.903223 | 3.740479 | −0.26735 | 1.072046 | 2.102413 | −0.47564 |
| IFNG | 2.802708 | 6.977488 | −0.14332 | 1.490329 | 2.80953 | −0.35593 | 1.49E−01 | 1.108801 | −0.90188 | 1.551388 | 2.930989 | −0.34118 | 0.692993 | 1.616634 | −0.61857 |
| IRF7 | 0.205875 | 1.153385 | −0.86701 | −0.15771 | 0.896445 | −1.11552 | 2.57E−01 | 1.194991 | −0.83683 | 0.246577 | 1.186389 | −0.84289 | 0.611687 | 1.528045 | −0.65443 |
| LAMP3 | 2.073901 | 4.210236 | −0.23752 | 1.736517 | 3.332297 | −0.30009 | 2 | 4 | −0.25 | 3.318566 | 9.976724 | −0.10023 | 1.457649 | 2.746604 | −0.36409 |
| LTF | 0.266449 | 1.202844 | −0.83136 | 0.800846 | 1.742123 | −0.57401 | −4.57E−01 | 0.7285 | −1.37268 | 0.42707 | 1.344501 | −0.74377 | 0.754031 | 1.686498 | −0.59294 |
| LY6E | −0.49094 | 0.711562 | −1.40536 | −0.19806 | 0.871721 | −1.14716 | 6.00E−10 | 1 | −1 | 1.69983 | 3.248627 | −0.30782 | 1.283252 | 2.433869 | −0.41037 |
| MERTK | 1.059574 | 2.084316 | −0.47977 | 0.740241 | 1.670455 | −0.59864 | 2.80E−09 | 1 | −1 | 1.680601 | 3.205615 | −0.31195 | 0.684434 | 1.607071 | −0.62225 |
| MS4A1 | 5.799233 | 55.68562 | −0.01796 | 5.3814 | 41.68337 | −0.02399 | 4.09E−01 | 1.327765 | −0.75315 | 1.361375 | 2.5693 | −0.38921 | 0.608129 | 1.524282 | −0.65605 |
| MT1E | −0.69526 | 0.617598 | −1.61918 | −0.82796 | 0.563324 | −1.77518 | −6.83E−01 | 0.622869 | −1.60547 | −0.24174 | 0.845724 | −1.18242 | 0.746512 | 1.677731 | −0.59604 |
| MX1 | 0.305822 | 1.236122 | −0.80898 | 2.313122 | 4.969572 | −0.20122 | 2.72 | 6.588728 | −0.15177 | 1.806287 | 3.497411 | −0.28593 | 1.061633 | 2.087293 | −0.47909 |
| OAS1 | 1.37623 | 2.595891 | −0.38522 | 1.475383 | 2.780575 | −0.35964 | 1.82 | 3.530812 | −0.28322 | 2.11593 | 4.33359 | −0.23076 | 1.286187 | 2.438825 | −0.41003 |
| OAS2 | 0.89659 | 1.861661 | −0.53715 | 1.15965 | 2.234033 | −0.44762 | 1.55 | 2.928171 | −0.34151 | 1.51621 | 2.860385 | −0.3496 | 0.970194 | 1.959104 | −0.51044 |
| PRTN3 | −0.19316 | 0.874688 | −1.14327 | 0.162426 | 1.119168 | −0.89352 | −2.00E−10 | 1 | −1 | 0.882185 | 1.843165 | −0.54254 | 0.64201 | 1.560502 | −0.64082 |
| RETN | −1.57076 | 0.336632 | −2.9706 | 0.245322 | 1.185357 | −0.84363 | −1.00E−09 | 1 | −1 | 1.62785 | 3.090521 | −0.32357 | 0.697149 | 1.621298 | −0.61679 |
| RNASE2 | 1.011167 | 2.01554 | −0.49614 | −0.13262 | 0.912172 | −1.09628 | 3.33E−10 | 1 | −1 | 1.97723 | 3.937362 | −0.25398 | 0.651278 | 1.570559 | −0.63672 |
| RNASE3 | −0.62414 | 0.648804 | −1.5413 | −0.51832 | 0.698182 | −1.43229 | 0 | 1 | −1 | 0.082042 | 1.058516 | −0.94472 | 0.609055 | 1.52526 | −0.65563 |
| SERPINB2 | 0.933084 | 1.90803 | −0.5241 | −0.46312 | 0.725414 | −1.37852 | −6.00E−10 | 1 | −1 | −0.45596 | 0.729027 | −1.37169 | 0.594594 | 1.510047 | −0.66223 |
| SERPING1 | −0.47939 | 0.717279 | −1.39416 | 0.074527 | 1.053016 | −0.94965 | 6.29E−01 | 1.546493 | −0.64662 | −0.31172 | 0.805681 | −1.24119 | 1.20902 | 2.311806 | −0.43256 |
| SIGLEC1 | 1.475638 | 2.781066 | −0.35957 | 1.611712 | 3.056143 | −0.32721 | 7.34E−02 | 1.052193 | −0.9504 | 0.743846 | 1.674635 | −0.59715 | 0.767565 | 1.702395 | −0.58741 |
| SLC1A3 | 2.315717 | 4.97852 | −0.20086 | 0.509184 | 1.423245 | −0.70262 | 1.13E−09 | 1 | −1 | 1.904716 | 3.744351 | −0.26707 | 0.764957 | 1.69932 | −0.58847 |
| SOCS1 | −0.96614 | 0.511872 | −1.95361 | −0.92433 | 0.526925 | −1.8978 | −6.67E−11 | 1 | −1 | 1.084708 | 2.120946 | −0.47149 | 0.830098 | 1.777806 | −0.56249 |

TABLE 5-continued

Table showing SS PBMC genes (≥+1.5 FC) in common with both SS and SLE genes (1849) identified by CPA analysis and their respective FC values in three independent SS salivary gland and one SLE synovial biopsy data sets.

| upregulated in PBMCs of SS female patients common in SS and SLE (ANNI) | minor SG | | | parotid gland | | | LSG | | | Sy SLE | | | PBMC (SS) | | |
|---|---|---|---|---|---|---|---|---|---|---|---|---|---|---|---|
| | logFC | FC | FC(−) | logFC | FC | FC(−) | logFC | FC | FC(−) | logFC | FC | FC(−) | logFC | FC | FC(−) |
| STAT2 | 1.240826 | 2.363338 | −0.42313 | 0.900419 | 1.866609 | −0.53573 | 1.33 | 2.514027 | −0.39777 | 0.781148 | 1.718498 | −0.5819 | 0.592008 | 1.507343 | −0.66342 |
| TRIM5 | 0.212043 | 1.158327 | −0.86331 | 0.087776 | 1.062731 | −0.94097 | 9.54E-01 | 1.937236 | −0.5162 | −0.13453 | 0.910964 | −1.09774 | 0.607184 | 1.523283 | −0.65648 |

TABLE 6

Table showing SS PBMC genes (≤−1.5 FC) in common with both SS and SLE genes (1849) identified by CPA analysis and their respective FC values in three independent SS salivary gland and one SLE synovial biopsy data sets.

| downregulated in PBMCs of SS female patients common in SS and SLE (ANNI) | minor SG | | | parotid gland | | | LSG | | |
|---|---|---|---|---|---|---|---|---|---|
| | logFC | FC | FC(−) | logFC | FC | FC(−) | logFC | FC | FC(−) |
| CLEC4C | 1.650199 | 3.138769 | −0.3186 | 0.982457 | 1.975827 | −0.50612 | −2E−10 | 1 | −1 |
| CXCL5 | −1.15116 | 0.450263 | −2.22093 | −1.06328 | 0.478542 | −2.08968 | −5.78E−01 | 0.669892 | −1.49278 |
| CXCR6 | 2.084287 | 4.240655 | −0.23581 | 1.30999 | 2.479398 | −0.40332 | 8.67E−10 | 1 | −1 |
| FCER1A | −0.41483 | 0.750109 | −1.33314 | 0.658308 | 1.578231 | −0.63362 | | 1 | −1 |
| GSTT1 | −2.26153 | 0.20855 | −4.79501 | −1.234 | 0.425136 | −2.35219 | −1.10E−06 | 0.999999 | −1 |
| ITGB3 | −1.1177 | 0.460826 | −2.17001 | 0.513587 | 1.427596 | −0.70048 | 5.33E−10 | 1 | −1 |
| MAGOH | −0.45806 | 0.727963 | −1.3737 | 0.410844 | 1.329463 | −0.75218 | −1.00E−09 | −1 | −1 |
| MAP2K3 | −1.3054 | 0.40461 | −2.47152 | −1.0197 | 0.493218 | −2.0275 | 3.00E−01 | 1.231144 | −0.81225 |
| PPBP | 1.474171 | 2.778239 | −0.35994 | −0.76493 | 0.588481 | −1.69929 | −2.60E−09 | 1 | −1 |
| SERPINE2 | 1.034284 | 2.048097 | −0.48826 | 0.391471 | 1.31173 | −0.76235 | −3.37E−05 | 0.999977 | −1.00002 |
| SPP1 | −2.05997 | 0.239821 | −4.16978 | −0.48431 | 0.714839 | −1.39892 | 0.017 | 1.011853 | −0.98829 |
| TNFRSF13B | −0.23706 | 0.848473 | −1.17859 | 0.759328 | 1.692701 | −0.59077 | −1.80E−07 | 1 | −1 |
| TNFRSF21 | −0.96422 | 0.512554 | −1.95101 | 0.564248 | 1.478616 | −0.67631 | 6.79E−01 | 1.60103 | −0.6246 |

| downregulated in PBMCs of SS female patients common in SS and SLE (ANNI) | Sy SLE | | | PBMC (SS) | | |
|---|---|---|---|---|---|---|
| | logFC | FC | FC(−) | logFC | FC | FC(−) |
| CLEC4C | 1.45073 | 2.733462 | −0.36584 | −0.58902 | 0.664793 | −1.50423 |
| CXCL5 | −4.39745 | 0.04745 | −21.0748 | −0.71063 | 0.611053 | −1.63652 |
| CXCR6 | 1.935581 | 3.825321 | −0.26142 | −0.8902 | 0.53954 | −1.85343 |
| FCER1A | −1.29861 | 0.406517 | −2.45992 | −0.80957 | 0.570553 | −1.75268 |
| GSTT1 | 0.142464 | 1.103788 | −0.90597 | −0.63709 | 0.64301 | −1.55519 |
| ITGB3 | 0.324839 | 1.252524 | −0.79839 | −0.63598 | 0.643504 | −1.55399 |
| MAGOH | 0.189156 | 1.140097 | −0.87712 | −0.62356 | 0.649066 | −1.54067 |
| MAP2K3 | −0.83789 | 0.55946 | −1.78744 | −0.58349 | 0.667348 | −1.49847 |
| PPBP | −3.05933 | 0.119964 | −8.33585 | −0.7109 | 0.610941 | −1.63682 |
| SERPINE2 | 0.436079 | 1.352922 | −0.73914 | −1.08129 | 0.472605 | −2.11593 |
| SPP1 | 3.963109 | 15.59605 | −0.06412 | −0.62321 | 0.649225 | −1.5403 |
| TNFRSF13B | 1.528942 | 2.88574 | −0.34653 | −0.58061 | 0.668682 | −1.49548 |
| TNFRSF21 | 1.816924 | 3.523291 | −0.28383 | −2.71224 | 0.152593 | −6.55339 |

TABLE 7

Table showing SLE PBMC genes (≥+1.5 FC) in common with both SS and SLE genes (1849) identified by CPA analysis and their respective FC values in three independent SS salivary gland and one SLE synovial biopsy data sets.

| upregulated in PBMCs of SLE female patients common in SS and SLE (ANNI) | minor SG | | | parotid gland | | | | LSG | | | Sy SLE | | | PBMC (SLE) | | |
|---|---|---|---|---|---|---|---|---|---|---|---|---|---|---|---|---|
| | logFC | FC | FC(−) | logFC | FC | FC(−) | logFC | FC | FC(−) | logFC | FC | FC(−) | logFC | FC | FC(−) |
| AIM2 | 2.842537 | 7.172801 | −0.13942 | 1.477101 | 2.783889 | −0.35921 | 3.85E−01 | 1.30586 | −0.76578 | 0.649092 | 1.568181 | −0.63768 | 0.603676 | 1.519584 | −0.65807 |
| ATXN1 | 1.132973 | 2.193103 | −0.45598 | −0.27422 | 0.826895 | −1.20934 | 4.59E−01 | 1.374589 | −0.72749 | 1.421217 | 2.678113 | −0.3734 | 0.705527 | 1.63074 | −0.61322 |
| AURKA | 1.055839 | 2.078927 | −0.48102 | 1.13594 | 2.197617 | −0.45504 | −8.67E−10 | 1 | −1 | 1.453243 | 2.738229 | −0.3652 | 0.637249 | 1.55536 | −0.64294 |
| BCL2L1 | −2.2359 | 0.212289 | −4.71056 | −0.57288 | 0.672275 | −1.48749 | 8.67E−10 | 1 | −1 | 1.111235 | 2.160305 | −0.4629 | 0.595814 | 1.511325 | −0.66167 |
| BCL2L11 | 0.695361 | 1.619289 | −0.61755 | −0.46917 | 0.722379 | −1.38432 | 9.73E−09 | 1 | −1 | 1.247204 | 2.373808 | −0.42126 | 0.928749 | 1.903625 | −0.52531 |
| BRCA1 | 0.599376 | 1.515061 | −0.66004 | 0.454201 | 1.370023 | −0.72991 | 2.00E−10 | 1 | −1 | 0.938657 | 1.916743 | −0.52172 | 0.723227 | 1.650871 | −0.60574 |
| CALR | −2.61202 | 0.16357 | −6.11361 | −0.70789 | 0.612215 | −1.63341 | 4.67E−02 | 1.0329 | −0.96815 | 1.418685 | 2.673417 | −0.37405 | 0.668024 | 1.588895 | −0.62937 |
| CASP7 | 0.136469 | 1.099211 | −0.90974 | −0.05882 | 0.960052 | −1.04161 | 6.05E−01 | 1.520979 | −0.65747 | 0.037397 | 1.02626 | −0.97441 | 0.581396 | 1.496296 | −0.66832 |
| CCL2 | 0.105594 | 1.075937 | −0.92942 | −1.10069 | 0.466294 | −2.14457 | 3.61E−01 | 1.284316 | −0.77862 | 0.348428 | 1.273173 | −0.78544 | 1.011832 | 2.01647 | −0.49592 |
| CCL3 | 2.116048 | 4.335048 | −0.23068 | −0.044345 | 0.735374 | −1.35985 | 1.67E−09 | 1 | −1 | 2.312261 | 4.966608 | −0.20134 | 0.815328 | 1.759698 | −0.56828 |
| CCL7 | 0.396496 | 1.316307 | −0.7597 | −0.2991 | 0.812759 | −1.23038 | −6.00E−10 | 1 | −1 | 2.162843 | 4.477964 | −0.22332 | 0.59362 | 1.509028 | −0.66268 |
| CCND2 | −0.46115 | 0.726407 | −1.37664 | 0.492337 | 1.406722 | −0.71087 | 7.06E−01 | 1.631275 | −0.61302 | 1.325035 | 2.50539 | −0.39914 | 1.033326 | 2.046673 | −0.48858 |
| CCR1 | 1.868718 | 3.652078 | −0.27382 | 1.359447 | 2.565868 | −0.38973 | 1.13 | 2.188587 | −0.45692 | 1.110847 | 2.159725 | −0.46302 | 0.727712 | 1.65601 | −0.60386 |
| CD164 | −0.28084 | 0.823113 | −1.2149 | 0.754023 | 1.68649 | −0.59295 | 7.85E−01 | 1.723092 | −0.58035 | 0.449291 | 1.365369 | −0.7324 | 0.755859 | 1.688637 | −0.59219 |
| CD38 | 0.641583 | 1.56004 | −0.64101 | 2.069005 | 4.195971 | −0.23832 | 1.28 | 2.42839 | −0.4118 | 2.363262 | 5.145323 | −0.19435 | 0.928774 | 1.903658 | −0.5253 |
| CD69 | 3.234386 | 9.411246 | −0.10626 | 2.512906 | 5.707685 | −0.1752 | 4.61E−01 | 1.376496 | −0.72648 | 1.095798 | 2.137313 | −0.46788 | 0.633482 | 1.551305 | −0.64462 |
| CDC25A | 1.516391 | 2.860744 | −0.34956 | −1.23989 | 0.423405 | −2.36181 | 0 | 1 | −1 | 1.703223 | 3.256277 | −0.3071 | 0.8276 | 1.774731 | −0.56347 |
| CDKN1A | 0.4212 | 1.33904 | −0.7468 | −1.12471 | 0.458595 | −2.18057 | 7.94E−02 | 1.056575 | −0.94645 | −1.36115 | 0.389271 | −2.56891 | 0.897936 | 1.863398 | −0.53665 |
| CDKN2C | −0.14292 | 0.905685 | −1.10414 | −1.27765 | 0.412467 | −2.42444 | 6.00E−10 | 1 | −1 | 0.401738 | 1.321098 | −0.75695 | 0.629957 | 1.547519 | −0.6462 |
| CENPA | 1.719617 | 3.293489 | −0.30363 | 0.363258 | 1.286327 | −0.77741 | −1.73E−09 | 1 | −1 | 1.457876 | 2.747036 | −0.36403 | 0.639132 | 1.557392 | −0.6421 |
| CFLAR | 2.778245 | 6.860175 | −0.14577 | −0.75512 | 0.592498 | −1.68777 | 8.95E−01 | 1.85961 | −0.53775 | 2.690065 | 6.453424 | −0.15496 | 0.761736 | 1.695529 | −0.58979 |
| CHEK1 | 1.297478 | 2.457989 | −0.40684 | 1.29416 | 2.452342 | −0.40777 | 9.33E−10 | 1 | −1 | −1.86695 | 0.274152 | −3.64761 | 0.665728 | 1.586369 | −0.63037 |
| CXCL10 | 3.957697 | 15.53766 | −0.06436 | 2.221076 | 4.662412 | −0.21448 | 2.31 | 4.958831 | −0.20166 | 3.543853 | 11.66289 | −0.08574 | 0.611952 | 1.528326 | −0.65431 |
| CXCL13 | 5.482544 | 44.71058 | −0.02237 | 5.930151 | 60.97522 | −0.0164 | 1.25 | 2.378414 | −0.42045 | 2.404489 | 5.29448 | −0.18888 | 1.064321 | 2.091186 | −0.4782 |
| CXCL2 | 1.989195 | 3.970153 | −0.25188 | −0.86411 | 0.549386 | −1.82021 | −3.33E−10 | 1 | −1 | 1.153453 | 2.224456 | −0.44955 | 0.651386 | 1.570675 | −0.63667 |
| DUSP4 | −0.74831 | 0.5953 | −1.62982 | −0.22903 | 0.853207 | −1.17205 | 5.29E−01 | 1.442929 | −0.69303 | 0.819693 | 1.76503 | −0.56656 | 0.971447 | 1.960806 | −0.50999 |
| ECT2 | −1.48467 | 0.357331 | −2.79853 | 0.5136 | 1.427608 | −0.70047 | 8.23E−01 | 1.769081 | −0.56527 | 0.659788 | 1.57985 | −0.63297 | 0.76636 | 1.700973 | −0.5879 |
| EDNRB | −1.15366 | 0.449485 | −2.22477 | −0.41509 | 0.749972 | −1.33338 | 9.67E−01 | 1.954772 | −0.51157 | 1.297996 | 2.45887 | −0.40669 | 0.717863 | 1.644744 | −0.608 |
| EIF2AK2 | 0.425221 | 1.342778 | −0.74472 | −0.15573 | 0.89768 | −1.11398 | 2.09 | 4.257481 | −0.23488 | 1.251078 | 2.380192 | −0.42013 | 0.873754 | 1.832425 | −0.54572 |
| ENPP1 | −0.71403 | 0.609614 | −1.64038 | −0.54199 | 0.686823 | −1.45598 | 8.87E−09 | 1 | −1 | −2.07477 | 0.237373 | −4.21277 | 0.632217 | 1.549945 | −0.64518 |
| ENTPD1 | 1.706782 | 3.264319 | −0.30634 | 1.178766 | 2.26383 | −0.44173 | 8.86E−02 | 1.063338 | −0.94043 | −0.86197 | 0.550201 | −1.81752 | 0.596487 | 1.51203 | −0.66136 |
| FAS | 2.22405 | 4.672032 | −0.21404 | 1.723052 | 3.301341 | −0.30291 | 7.59E−01 | 1.692317 | −0.59091 | 0.664618 | 1.585148 | −0.63086 | 0.686 | 1.608817 | −0.62157 |
| HESX1 | 0.946529 | 1.92723 | −0.51888 | −0.016625 | 0.988524 | −1.01161 | −2.67E−01 | 1 | −1 | 0.869998 | 1.82766 | −0.54715 | 0.750176 | 1.681998 | −0.59453 |
| HNRNPUL1 | −0.89319 | 0.538424 | −1.85727 | 0.363258 | 1.286327 | −0.77741 | 9.33E−10 | 1 | −1 | 0.406023 | 1.325028 | −0.7547 | 0.62936 | 1.546879 | −0.64646 |
| HSP90B1 | 0.548729 | 1.462796 | −0.68362 | 0.270184 | 1.205961 | −0.82921 | 8.63E−01 | 1.818817 | −0.54981 | 0.462834 | 1.378246 | −0.72556 | 0.588712 | 1.503904 | −0.66494 |
| IFI27 | 1.144387 | 2.210521 | −0.45238 | 1.205464 | 2.306114 | −0.43363 | 3.08 | 8.456144 | −0.11826 | 1.659594 | 3.159275 | −0.31653 | 2.6999 | 6.497567 | −0.1539 |
| IFI44 | 1.179165 | 2.264457 | −0.44161 | 1.935279 | 3.824521 | −0.26147 | 3.21 | 9.253505 | −0.10807 | 0.673944 | 1.595429 | −0.62679 | 1.786939 | 3.45082 | −0.28979 |
| IFIH1 | 1.105175 | 2.15125 | −0.46485 | 1.127891 | 2.18539 | −0.45758 | 1.93 | 3.810552 | −0.26243 | 1.881265 | 3.683978 | −0.27145 | 1.21656 | 2.323919 | −0.43031 |
| IFIT1 | 0.50819 | 1.422265 | −0.7031 | 2.61284 | 6.117067 | −0.16348 | 2.81 | 7.012846 | −0.1426 | 1.193586 | 2.287206 | −0.43721 | 1.732708 | 3.323511 | −0.30089 |
| IFIT3 | 1.363558 | 2.573189 | −0.38862 | 2.458242 | 5.495465 | −0.18197 | 2.84 | 7.160201 | −0.13966 | 1.903223 | 3.740479 | −0.26735 | 1.525815 | 2.879493 | −0.34728 |
| IFITM1 | 0.822119 | 1.768001 | −0.56561 | 1.532782 | 2.893433 | −0.34561 | 1.21 | 2.313376 | −0.43227 | 0.348808 | 1.273508 | −0.78523 | 1.037633 | 2.052856 | −0.48713 |

TABLE 7-continued

Table showing SLE PBMC genes (≥+1.5 FC) in common with both SS and SLE genes (1849) identified by CPA analysis and their respective FC values in three independent SS salivary gland and one SLE synovial biopsy data sets.

| upregulated in PBMCs of SLE female patients common in SS and SLE (ANNI) | minor SG | | | parotid gland | | | | LSG | | | Sy SLE | | | PBMC (SLE) | | |
|---|---|---|---|---|---|---|---|---|---|---|---|---|---|---|---|---|
| | logFC | FC | FC(−) | logFC | FC | FC(−) | logFC | FC | FC(−) | logFC | FC | FC(−) | logFC | FC | FC(−) |
| IGF1 | −0.53365 | 0.681292 | −1.4678 | 0.921285 | 1.893801 | −0.52804 | 8.66E-01 | 1.822603 | −0.54867 | 1.381988 | 2.606273 | −0.38369 | 0.601414 | 1.517203 | −0.65911 |
| IGJ | −0.07818 | 0.947254 | −1.05568 | 0.64563 | 1.564423 | −0.63921 | 8.43E-02 | 1.060173 | −0.94324 | 3.109689 | 8.631967 | −0.11585 | 1.1221121 | 2.176667 | −0.45942 |
| IL1A | 0.693884 | 1.617632 | −0.61819 | −0.23223 | 0.851317 | −1.17465 | 1.27E-09 | 1 | −1 | 0.344795 | 1.26997 | −0.78742 | 0.643326 | 1.561926 | −0.64024 |
| IRF7 | 0.205875 | 1.153385 | −0.86701 | −0.15771 | 0.896445 | −1.11552 | 2.57E-01 | 1.194991 | −0.8368 | 0.246577 | 1.186389 | −0.84289 | 1.02727 | 2.038163 | −0.49064 |
| ISG20 | 0.486659 | 1.401196 | −0.71368 | 2.927264 | 7.606665 | −0.13146 | 5.89E-01 | 1.504204 | −0.6648 | 4.531894 | 23.13322 | −0.04323 | 1.450945 | 2.733871 | −0.36578 |
| ITGA6 | −0.89629 | 0.537266 | −1.86127 | 0.339518 | 1.265333 | −0.79031 | 1.58 | 2.989698 | −0.33448 | 0.607008 | 1.523097 | −0.65656 | 0.625079 | 1.542295 | −0.64838 |
| ITGB3 | −1.1177 | 0.460826 | −2.17001 | −0.85621 | 0.552401 | −1.81028 | 5.33E-10 | 1 | −1 | 1.691282 | 3.229436 | −0.30965 | 0.77434 | 1.710408 | −0.58466 |
| JUN | −1.05907 | 0.479941 | −2.08359 | −0.70919 | 0.611662 | −1.63489 | −1.64E-08 | 1 | −1 | −0.60047 | 0.659537 | −1.51621 | 0.643368 | 1.561971 | −0.64022 |
| KLRC1 | 1.111779 | 2.16112 | −0.46272 | 1.494584 | 2.817828 | −0.35488 | 2.82E-07 | 1 | −1 | −0.33009 | 0.795488 | −1.25709 | 0.70523 | 1.630405 | −0.61334 |
| LAG3 | 1.496869 | 2.822296 | −0.35432 | 1.454395 | 2.740417 | −0.36491 | −2.58E-03 | 0.998213 | −1.00179 | 0.996072 | 1.994562 | −0.50136 | 0.724576 | 1.652415 | −0.60517 |
| LAMP3 | 2.073901 | 4.210236 | −0.23752 | 1.736517 | 3.332297 | −0.30009 | 2 | 4 | −0.25 | 3.318566 | 9.976724 | −0.10023 | 2.084854 | 4.242323 | −0.23572 |
| LDLR | −1.36793 | 0.387447 | −2.581 | −1.4424 | 0.367954 | −2.71773 | 8.11E-01 | 1.754427 | −0.56999 | −2.7471 | 0.14895 | −6.71368 | 0.689407 | 1.61262 | −0.62011 |
| LY6E | −0.49094 | 0.711562 | −1.40536 | −0.19806 | 0.871721 | −1.14715 | 6.00E-10 | 1 | −1 | 1.69983 | 3.248627 | −0.30782 | 1.044968 | 2.06332 | −0.48466 |
| MKI67 | 1.072409 | 2.102941 | −0.47552 | 1.655966 | 3.151341 | −0.31733 | 2.27E-09 | 1 | −1 | 3.210673 | 9.257871 | −0.10802 | 1.445644 | 2.723843 | −0.36713 |
| MT1E | −0.69526 | 0.617598 | −1.61918 | −0.82796 | 0.563324 | −1.77518 | −6.83E-01 | 0.622869 | −1.60547 | −0.24174 | 0.845724 | −1.18242 | 0.662449 | 1.582767 | −0.6318 |
| MUC1 | −1.59304 | 0.331472 | −3.01684 | −1.47497 | 0.359741 | −2.77978 | 7.90E-01 | 1.729074 | −0.57834 | 0.396889 | 1.316666 | −0.75949 | 0.899441 | 1.865344 | −0.53609 |
| MX1 | 0.305822 | 1.236122 | −0.80898 | 2.313122 | 4.969572 | −0.20122 | 2.72 | 6.588728 | −0.15177 | 1.806287 | 3.497411 | −0.28593 | 1.560615 | 2.949795 | −0.33901 |
| OAS1 | 1.37623 | 2.595891 | −0.38522 | 1.475383 | 2.780575 | −0.35964 | 1.82 | 3.530812 | −0.28322 | 2.115563 | 4.33359 | −0.23076 | 1.05956 | 2.084296 | −0.47978 |
| OAS2 | 0.89659 | 1.861661 | −0.53715 | 1.15965 | 2.234033 | −0.44762 | 1.55 | 2.928171 | −0.34151 | 1.51621 | 2.860385 | −0.3496 | 0.907938 | 1.876362 | −0.53295 |
| PDPN | −1.79941 | 0.287291 | −3.48079 | 0.123291 | 1.089216 | −0.91809 | 1.78E-15 | 1 | −1 | −0.68251 | 0.623079 | −1.60493 | 0.978213 | 1.970024 | −0.50761 |
| PLAT | −0.73834 | 0.59943 | −1.66825 | −0.06445 | 0.956311 | −1.04568 | 2.19E-01 | 1.163927 | −0.85916 | 0.27758 | 1.21216 | −0.82497 | 0.592323 | 1.507672 | −0.66327 |
| PML | −2.27052 | 0.207255 | −4.82496 | −1.39398 | 0.380513 | −2.52803 | 1.80E-01 | 1 | −1 | 0.872747 | 1.831146 | −0.54611 | 1.399262 | 2.637666 | −0.37912 |
| PNMA2 | 0.946994 | 1.927852 | −0.51871 | 0.509821 | 1.423873 | −0.70231 | −1.33E-10 | 1 | −1 | 1.34748 | 2.544673 | −0.39298 | 0.674944 | 1.596534 | −0.62636 |
| POLR2A | −0.83461 | 0.560736 | −1.78337 | −0.52907 | 0.693003 | −1.44299 | 5.80E-09 | 1 | −1 | 1.517451 | 2.862848 | −0.3493 | 0.673385 | 1.594811 | −0.62703 |
| POU2AF1 | 1.894038 | 3.71674 | −0.26905 | −1.3987 | 0.379271 | −2.63664 | 1.49 | 2.80889 | −0.35601 | 2.187189 | 4.554174 | −0.21958 | 0.786187 | 1.72451 | −0.57987 |
| PRF1 | 1.128922 | 2.186953 | −0.45726 | 0.655721 | 1.575403 | −0.63476 | 1.53E-09 | 1 | −1 | 0.822792 | 1.768825 | −0.56535 | 0.608801 | 1.524991 | −0.65574 |
| RAD51 | 1.827541 | 3.549316 | −0.28174 | 1.079478 | 2.113271 | −0.4732 | −4.00E-10 | 1 | −1 | 0.784158 | 1.722086 | −0.58069 | 0.832712 | 1.781031 | −0.56147 |
| RRAS2 | −0.72488 | 0.605048 | −1.65276 | −0.41881 | 0.748041 | −1.33682 | 1.47E-09 | 1 | −1 | −0.85788 | 0.551762 | −1.81238 | 0.698051 | 1.622311 | −0.6164 |
| RRM2 | 2.043314 | 4.121913 | −0.24261 | 2.59541 | 6.043606 | −0.16546 | 5.51E-01 | 1.465101 | −0.68255 | 2.296888 | 4.913966 | −0.2035 | 1.436556 | 2.706739 | −0.36945 |
| SERPING1 | −0.47939 | 0.717279 | −1.39416 | 0.074527 | 1.053016 | −0.94965 | 6.29E-01 | 1.546493 | −0.64662 | −0.31172 | 0.805681 | −1.24119 | 1.029886 | 2.041862 | −0.48975 |
| SIGLEC1 | 1.475638 | 2.781066 | −0.35957 | 1.611712 | 3.056143 | −0.32721 | 7.34E-02 | 1.052193 | −0.9504 | 0.743846 | 1.674635 | −0.59715 | 1.008976 | 2.012482 | −0.4969 |
| SLC6A2 | −1.27222 | 0.414022 | −2.41533 | −0.77531 | 0.584264 | −1.71156 | 3.55E-15 | 1 | −1 | 2.972634 | 7.849682 | −0.12739 | 0.625685 | 1.542943 | −0.64811 |
| SOD2 | 1.470841 | 2.771834 | −0.36077 | 0.792633 | 1.732232 | −0.57729 | 2.87E-09 | 1 | −1 | 1.852208 | 3.610524 | −0.27697 | 0.604931 | 1.520906 | −0.6575 |
| STAT1 | 2.860235 | 7.261337 | −0.13772 | 2.014552 | 4.040552 | −0.24749 | 3.27 | 9.646463 | −0.10366 | 2.119747 | 4.346177 | −0.23009 | 1.575784 | 2.980974 | −0.33546 |
| TAP1 | 1.891464 | 3.710115 | −0.26953 | 1.439858 | 4.06097 | −0.3686 | 1.5 | 2.828427 | −0.35355 | 1.154641 | 2.226289 | −0.44918 | 0.946934 | 1.927771 | −0.51873 |
| THBS1 | −1.15274 | 0.449769 | −2.22336 | −1.17052 | 0.44426 | −2.25093 | 7.71E-01 | 1.706452 | −0.58601 | −1.42951 | 0.371258 | −2.69355 | 0.79863 | 1.739449 | −0.57489 |
| TLR7 | 2.231513 | 4.696262 | −0.21294 | 1.902859 | 3.739536 | −0.26741 | 6.91E-01 | 1.614402 | −0.61942 | 1.47697 | 2.783636 | −0.35924 | 0.640626 | 1.559006 | −0.64143 |
| TNFRSF17 | 0.394556 | 1.314538 | −0.76072 | 1.299227 | 2.46097 | −0.40634 | −9.40E-03 | 0.993506 | −1.00654 | 3.657591 | 12.61957 | −0.07924 | 0.738862 | 1.668859 | −0.59921 |
| TSHR | 2.565096 | 5.917943 | −0.16898 | 0.700404 | 1.624959 | −0.6154 | 1 | 1 | −1 | 1.721548 | 3.297902 | −0.30322 | 0.654006 | 1.573531 | −0.63551 |
| TXN | −0.3731 | 0.772123 | −1.29513 | 0.404396 | 1.323534 | −0.75555 | −2.63E-01 | 0.833353 | −1.19997 | 0.234167 | 1.176227 | −0.85018 | 0.692447 | 1.616022 | −0.6188 |

TABLE 8

Table showing SLE PBMC genes (≤−1.5 FC) in common with both SS and SLE genes (1579) identified by CPA analysis and their respective FC values in three independent SS salivary gland and one SLE synovial biopsy data sets.

| downregulated in PBMCs of SLE female patients common in SS and SLE (ANNI) | minor SG | | | parotid gland | | | LSG | | | Sy SLE | | | PBMC (SLE) | | |
|---|---|---|---|---|---|---|---|---|---|---|---|---|---|---|---|
| | logFC | FC | FC(−) | logFC | FC | FC(−) | logFC | FC | FC(−) | logFC | FC | FC(−) | logFC | FC | FC(−) |
| ABCB1 | −0.47205 | 0.720941 | −1.38708 | 1.005412 | 2.007517 | −0.49813 | 9.23E-02 | 1.066068 | −0.93803 | −0.47205 | 0.720941 | −1.38708 | −0.83313 | 0.56131 | −1.78155 |
| ANGPT2 | −0.27076 | 0.828833 | −1.20644 | 0.986247 | 1.981025 | −0.50479 | −8.88E-16 | 1 | −1 | −1.60365 | 0.329043 | −3.03912 | −0.63205 | 0.645257 | −1.54977 |
| APOA1 | 0.946201 | 1.926792 | −0.519 | −0.82876 | 0.563015 | −1.77615 | −2.47E-09 | 1 | −1 | 1.272845 | 2.416376 | −0.41384 | −0.76786 | 0.587289 | −1.70274 |
| ATG16L1 | 1.061257 | 2.086749 | −0.47921 | −0.46673 | 0.723601 | −1.38198 | 4.67E-09 | 1 | −1 | 0.700431 | 0.704431 | −1.42769 | −0.87804 | 0.544108 | −1.83787 |
| ATP2A3 | −1.67953 | 0.312184 | −3.20324 | −0.64699 | 0.63861 | −1.5659 | 3.88E-01 | 1.308578 | −0.76419 | 2.813531 | 7.030032 | −0.14225 | −0.58777 | 0.665373 | −1.50292 |
| ATXN3 | 1.273594 | 2.41763 | −0.41363 | 0.628184 | 1.545618 | −0.64699 | 4.00E-09 | 1 | −1 | 0.507163 | 1.421253 | −0.7036 | −0.58457 | 0.666848 | −1.49959 |
| BACE1 | −0.78354 | 0.58094 | −1.72135 | −0.70045 | 0.615381 | −1.62501 | 3.40E-09 | 1 | −1 | −0.29279 | 0.816322 | −1.22501 | −0.58318 | 0.667489 | −1.49815 |
| BMP7 | 0.471256 | 1.386316 | −0.72134 | 0.750974 | 1.682929 | −0.5942 | −2.00E-10 | 1 | −1 | 0.660695 | 1.580844 | −0.63257 | −0.74623 | 0.596158 | −1.67741 |
| CCKAR | 1.063871 | 2.090533 | −0.47835 | −0.13827 | 0.908607 | −1.10059 | −3.33E-10 | 1 | −1 | 1.103016 | 2.148033 | −0.46554 | −0.60979 | 0.655292 | −1.52604 |
| CCL19 | 3.583547 | 11.98823 | −0.08342 | 2.826726 | 7.094624 | −0.14095 | 9.53E-01 | 1.935894 | −0.51656 | 1.666199 | 3.173773 | −0.31508 | −0.6324 | 0.645104 | −1.55014 |
| CD1C | 1.276714 | 2.422864 | −0.41273 | 1.912544 | 3.764724 | −0.26562 | −4.12E-01 | 0.751581 | −1.33053 | −1.61022 | 0.327549 | −3.05298 | −0.90674 | 0.53339 | −1.8748 |
| CD1D | 2.779893 | 6.868012 | −0.1456 | 2.544417 | 5.833722 | −0.17142 | 1.08E-02 | 1.007514 | −0.99254 | 2.031687 | 4.088828 | −0.2445 | −0.80218 | 0.573482 | −1.74373 |
| CD1E | −0.74546 | 0.596476 | −1.67651 | 2.222918 | 4.668381 | −0.21421 | 8.08E-02 | 1.057604 | −0.94553 | −1.31777 | 0.401155 | −2.4928 | −0.67701 | 0.625461 | −1.59882 |
| CFD | −0.96167 | 0.513462 | −1.94756 | −0.76806 | 0.587208 | −1.70297 | −1.21 | 0.432269 | −2.31338 | 0.498311 | 1.412559 | −0.70793 | −0.86247 | 0.55001 | −1.81815 |
| CLCN1 | 0.399774 | 1.319301 | −0.75798 | −0.89463 | 0.537884 | −1.85914 | −2.73E-09 | 1 | −1 | 0.340459 | 1.266159 | −0.78979 | −0.61086 | 0.654808 | −1.52717 |
| COL11A1 | −0.78734 | 0.579413 | −1.72589 | 0.850129 | 1.802663 | −0.55473 | 1.53E-09 | 1 | −1 | −3.50061 | 0.088351 | −11.3185 | −0.62923 | 0.646521 | −1.54674 |
| COL2A1 | 0.453265 | 1.369135 | −0.73039 | 0.331063 | 1.25794 | −0.79495 | −6.67E-10 | 1 | −1 | −2.10508 | 0.232438 | −4.30222 | −0.5895 | 0.664575 | −1.50472 |
| COL4A3 | 2.307923 | 4.951697 | −0.20195 | 1.267605 | 2.407615 | −0.41535 | 5.51E-01 | 1.465101 | −0.68255 | −0.57314 | 0.672154 | −1.48775 | −0.5806 | 0.668687 | −1.49547 |
| COL5A1 | −0.64039 | 0.641537 | −1.55876 | −0.72643 | 0.604398 | −1.65454 | 1.34E-01 | 1.097332 | −0.9113 | −1.68867 | 0.310213 | −3.22359 | −0.74764 | 0.595579 | −1.67904 |
| CXCR5 | 0.957214 | 1.941557 | −0.51505 | 2.158527 | 2.158527 | −0.46328 | −4.00E-10 | 1 | −1 | −0.88282 | 0.542307 | −1.84397 | −0.66091 | 0.632479 | −1.58108 |
| CYP27A1 | −0.15131 | 0.900432 | −1.11058 | 0.677249 | 1.599087 | −0.62536 | −2.60E-09 | 1 | −1 | 1.499058 | 2.826581 | −0.35378 | −0.72693 | 0.604189 | −1.65511 |
| ENG | −0.48808 | 0.712976 | −1.40257 | 0.647478 | 1.566428 | −0.6384 | −6.00E-10 | 1 | −1 | 0.57702 | 1.491765 | −0.67035 | −0.58022 | 0.668863 | −1.49507 |
| FCER1A | −0.41483 | 0.750109 | −1.33314 | 0.658308 | 1.578231 | −0.63362 | −1.07E-09 | 1 | −1 | −1.29861 | 0.406517 | −2.45992 | −1.13987 | 0.4538 | −2.20361 |
| FCGRT | −1.16353 | 0.44642 | −2.24004 | −0.65167 | 0.636541 | −1.57099 | −4.73E-09 | 1 | −1 | 0.689428 | 1.612643 | −0.6201 | −0.67455 | 0.626526 | −1.5961 |
| FOXO3 | −0.18942 | 0.876957 | −1.14067 | −1.18467 | 0.439925 | −2.27311 | 5.31E-01 | 1.44493 | −0.69207 | −1.05903 | 0.479956 | −2.08352 | −0.60443 | 0.657733 | −1.52037 |
| HLA-DQB1 | 2.864708 | 7.283885 | −0.13729 | 2.3332 | 5.039218 | −0.19844 | 5.97E-01 | 1.512568 | −0.66113 | 2.340585 | 5.065081 | −0.19743 | −2.33583 | 0.198082 | −5.04843 |
| HTR1A | −0.38348 | 0.766588 | −1.30448 | −0.12231 | 0.918714 | −1.08848 | −1.20E-09 | 1 | −1 | −1.67359 | 0.313473 | −3.19007 | −0.81971 | 0.566556 | −1.76505 |
| ITGB1 | 1.775254 | 3.422982 | −0.29214 | 1.685462 | 3.216434 | −0.3109 | 1.63 | 3.09513 | −0.32309 | −2.10384 | 0.232639 | −4.29851 | −0.72045 | 0.606906 | −1.6477 |
| JUND | −0.27637 | 0.825668 | −1.21114 | −1.07123 | 0.475913 | −2.10122 | −1.20E-09 | 1 | −1 | 1.343913 | 2.538389 | −0.39395 | −1.15633 | 0.448652 | −2.2289 |
| KCNH2 | 0.599018 | 1.514686 | −0.6602 | −1.04545 | 0.484493 | −2.06401 | −3.33E-10 | 1 | −1 | 0.350021 | 1.274579 | −0.78457 | −0.67923 | 0.624499 | −1.60128 |
| KIT | 0.009165 | 1.006373 | −0.99367 | 0.19799 | −1.147099 | −0.87176 | 5.20E-01 | 1.433955 | −0.69737 | 0.64301 | 1.561584 | −0.64038 | −0.8546 | 0.553013 | −1.80826 |
| LCAT | −0.72039 | 0.606935 | −1.64762 | 0.36674 | 1.289436 | −0.77553 | 1.78E-15 | 1 | −1 | −2.60354 | 0.164534 | −6.07776 | −0.87348 | 0.54583 | −1.83207 |
| MUC6 | −1.36706 | 0.38768 | −2.57945 | −0.36699 | 0.775398 | −1.28966 | −9.32E-08 | 1 | −1 | −0.6148 | 0.653019 | −1.53135 | −0.61824 | 0.651466 | −1.535 |
| NR4A1 | −1.41216 | 0.37575 | −2.66134 | −0.54377 | 0.685977 | −1.45777 | −3.47E-09 | 1 | −1 | −1.51649 | 0.349935 | −2.86095 | −0.62677 | 0.647624 | −1.54411 |
| PBX1 | −1.69886 | 0.308029 | −3.24645 | −0.68922 | 0.620191 | −1.61241 | 7.08E-01 | 1.633538 | −0.61217 | −1.82998 | 0.546455 | −1.82998 | −0.65332 | 0.635816 | −1.57278 |
| PDE4D | −0.45165 | 0.731208 | −1.3676 | 0.29698 | 1.22857 | −0.81395 | 4.33E-09 | 1 | −1 | 1.557114 | 2.942647 | −0.33983 | −0.60573 | 0.657137 | −1.52175 |
| PPARGC1A | −0.81381 | 0.568879 | −1.75784 | −0.75611 | 0.592091 | −1.68893 | 4.33E-09 | 1 | −1 | −1.15140 | 0.450018 | −2.22213 | −0.88977 | 0.539699 | −1.85289 |
| PTAFR | 0.732891 | 1.661967 | −0.6017 | 1.078297 | 2.111542 | −0.47359 | 2.66E-15 | 1 | −1 | 1.651022 | 3.14056 | −0.31841 | −0.86037 | 0.550813 | −1.8155 |
| PTGIS | −0.8704 | 0.545996 | −1.82817 | −1.16592 | 0.44568 | −2.24376 | 2.66E-15 | 1 | −1 | 2.181901 | 4.537511 | −0.22039 | −0.72827 | 0.603626 | −1.65666 |
| S100B | −0.49743 | 0.708366 | −1.4117 | −0.50881 | 0.7028 | −1.42288 | 2.20E-01 | 1.164734 | −0.85857 | 1.421826 | 2.679244 | −0.37324 | −0.68536 | 0.621852 | −1.6081 |
| SLC18A2 | 0.912629 | 1.882473 | −0.53122 | 0.659388 | 1.579413 | −0.63315 | 3.07E-09 | 1 | −1 | −0.2277 | 0.853996 | −1.17097 | −0.62338 | 0.64915 | −1.54048 |

TABLE 8-continued

Table showing SLE PBMC genes (≤−1.5 FC) in common with both SS and SLE genes (1579) identified by CPA analysis and their respective FC values in three independent SS salivary gland and one SLE synovial biopsy data sets.

| downregulated in PBMCs of SLE female patients common in SS and SLE (ANNI) | minor SG | | | parotid gland | | | LSG | | | Sy SLE | | | PBMC (SLE) | | |
|---|---|---|---|---|---|---|---|---|---|---|---|---|---|---|---|
| | logFC | FC | FC(−) | logFC | FC | FC(−) | logFC | FC | FC(−) | logFC | FC | FC(−) | logFC | FC | FC(−) |
| SOX9 | −0.80413 | 0.572708 | −1.74609 | −0.66644 | 0.630059 | −1.58715 | 7.12E−01 | 1.638073 | −0.61047 | −1.31592 | 0.40167 | −2.48961 | −0.584 | 0.66711 | −1.499 |
| TACR1 | −1.64618 | 0.319486 | −3.13003 | −1.08683 | 0.470795 | −2.12407 | 2.67E−10 | 1 | −1 | −1.53377 | 0.345374 | −2.89541 | −0.58244 | 0.667832 | −1.49738 |
| TCF3 | −1.03908 | 0.486637 | −2.05492 | 0.561003 | 1.475294 | −0.67783 | 5.47E−09 | 1 | −1 | −0.54642 | 0.684719 | −1.46045 | −0.6918 | 0.619079 | −1.6153 |
| TNFRSF11B | −0.51588 | 0.699366 | −1.42987 | 0.593916 | 1.509338 | −0.66254 | 6.95E−01 | 1.618884 | −0.61771 | −0.35178 | 0.783616 | −1.27614 | −1.46387 | 0.362518 | −2.75848 |
| TNXB | −1.40005 | 0.378917 | −2.6391 | −0.84761 | 0.555704 | −1.79952 | 8.88E−16 | 1 | −1 | −2.47474 | 0.179899 | −5.55868 | −0.69084 | 0.619492 | −1.61423 |
| TPO | −1.04462 | 0.484773 | −2.06282 | 0.120583 | 1.087174 | −0.91982 | −4.67E−10 | 1 | −1 | 1.435589 | 2.704925 | −0.3697 | −0.8586 | 0.551487 | −1.81328 |
| UCP2 | 1.070366 | 2.099967 | −0.4762 | 1.254574 | 2.385967 | −0.41912 | 2.17E−01 | 1.162314 | −0.86035 | 1.569155 | 2.967308 | −0.33701 | −0.58607 | 0.666153 | −1.50116 |
| YBX1 | −0.37995 | 0.763467 | −1.30129 | 0.490919 | 1.40534 | −0.71157 | −2.84E−01 | 0.821311 | −1.21757 | 0.705629 | 1.630855 | −0.61318 | −0.62894 | 0.646652 | −1.54643 |
| ZNF135 | −1.41 | 0.376312 | −2.65737 | −0.11852 | 0.921135 | −1.08562 | 3.33E−10 | 1 | −1 | −0.99405 | 0.502067 | −1.99176 | −0.992 | 0.502781 | −1.98894 |

TABLE 9

Table showing RA PBMC genes (≥+1.5 FC) in common with both SS and RA genes (1674) identified by CPA analysis and their respective FC values in three independent SS salivary gland and one RA synovial fluid data sets.

| Commonly upregulated in PBMCs of SS and RA female patients | minor SG | | | parotid gland | | | LSG | | |
|---|---|---|---|---|---|---|---|---|---|
| | logFC | FC | FC(−) | logFC | FC | FC(−) | logFC | FC | FC(−) |
| ABCA1 | 1.427567 | 2.689927 | −0.37176 | 1.224783 | 2.337204 | −0.42786 | 8.08E−01 | 1.750783 | −0.57117 |
| AIF1 | 1.519362 | 2.866642 | −0.34884 | 2.327247 | 5.018468 | −0.19926 | −8.00E−10 | 1 | −1 |
| AZU1 | −0.92172 | 0.527879 | −1.89437 | 0.15066 | 1.110078 | −0.90084 | −5.33E−10 | 1 | −1 |
| BPI | −0.70422 | 0.613774 | −1.62926 | −1.06167 | 0.479078 | −2.08734 | −7.33E−10 | 1 | −1 |
| CA4 | −2.16071 | 0.223646 | −4.47136 | −0.89787 | 0.536679 | −1.86331 | −1.33E−10 | 1 | −1 |
| CAMP | −0.22913 | 0.853147 | −1.17213 | −1.16484 | 0.446013 | −2.24209 | −2.62E−01 | 0.833931 | −1.19914 |
| CTSG | −0.85747 | 0.551919 | −1.81186 | −0.30351 | 0.810277 | −1.23415 | −3.96E−01 | 0.759962 | −1.31585 |
| DYNLT1 | 0.427692 | 1.34508 | −0.74345 | −0.23588 | 0.849165 | −1.17763 | −2.09E−01 | 0.865137 | −1.15589 |
| EIF2AK2 | −1.15366 | 0.449485 | −2.22477 | −0.41509 | 0.749972 | −1.33338 | 9.67E−01 | 1.954772 | −0.51157 |
| HMGB2 | 0.767887 | 1.702774 | −0.58728 | 1.24369 | 2.368035 | −0.42229 | 2.06E−01 | 1.153486 | −0.86694 |
| LCN2 | −1.14653 | 0.45171 | −2.21381 | 0.16916 | 1.124404 | −0.88936 | −1.53 | 0.346277 | −2.88786 |
| LY96 | 2.098145 | 4.281584 | −0.23356 | 0.597445 | 1.513034 | −0.66092 | 3.57E−01 | 1.28076 | −0.78079 |
| MMP9 | 3.476075 | 11.12764 | −0.08987 | 2.251394 | 4.761428 | −0.21002 | 5.67E−01 | 1.48144 | −0.67502 |
| NUP214 | 1.026982 | 2.037756 | −0.49074 | −0.98736 | 0.504399 | −1.98256 | 2.00E−10 | 1 | −1 |
| PADI4 | 1.104707 | 2.150552 | −0.465 | −1.29956 | 0.406249 | −2.46154 | −1.33E−10 | 1 | −1 |
| PPBP | 1.474171 | 2.778239 | −0.35994 | −0.76429 | 0.588481 | −1.69929 | −2.60E−09 | 1 | −1 |
| RETN | −1.57076 | 0.336632 | −2.9706 | 0.245322 | 1.185357 | −0.84363 | −1.00E−09 | 1 | −1 |
| RNASE2 | 1.011167 | 2.01554 | −0.49614 | −0.13262 | 0.912172 | −1.09628 | 3.33E−10 | 1 | −1 |
| RNASE3 | −0.62414 | 0.648804 | −1.5413 | −0.51832 | 0.698182 | −1.43229 | 0.00E+00 | 1 | −1 |
| S100A12 | −1.11481 | 0.461752 | −2.16566 | −0.57974 | 0.669083 | −1.49458 | −4.00E−10 | 1 | −1 |
| S100A8 | 1.069344 | 2.098479 | −0.47654 | 1.417006 | 2.670309 | −0.37449 | 1.17E−08 | 1 | −1 |
| S100A9 | 1.303998 | 2.469122 | −0.405 | 0.633529 | 1.551355 | −0.6446 | −2.62E−01 | 0.833931 | −1.19914 |
| SLC11A1 | 1.13079 | 2.189786 | −0.45667 | −0.691 | 0.619426 | −1.6144 | 6.67E−10 | 1 | −1 |
| SLPI | −0.12929 | 0.91428 | −1.09376 | −0.73346 | 0.601461 | −1.66262 | 9.79E−02 | 1.070215 | −0.93439 |
| THBS1 | 0.029551 | 1.020694 | −0.97973 | −1.17052 | 0.44426 | −2.25093 | 7.71E−01 | 1.706452 | −0.58601 |
| TLR5 | 0.067371 | 1.047806 | −0.95438 | −0.7709 | 0.586052 | −1.70633 | 2.00E−10 | 1 | −1 |
| TNFSF10 | −0.47291 | 0.720508 | −1.38791 | 0.649339 | 1.56845 | −0.63757 | 5.71E−01 | 1.485553 | −0.67315 |

| Commonly upregulated in PBMCs of SS and RA female patients | Sy fibroblast RA | | | PBMC (RA) | | |
|---|---|---|---|---|---|---|
| | logFC | FC | FC(−) | logFC | FC | FC(−) |
| ABCA1 | 0.661288 | 1.581494 | −0.63231 | 0.788051 | 1.72674 | −0.57913 |
| AIF1 | 0.766511 | 1.701151 | −0.58784 | 0.817847 | 1.762773 | −0.56729 |
| AZU1 | −0.10269 | 0.931296 | −1.07377 | 0.747249 | 1.678588 | −0.59574 |
| BPI | −1.02467 | 0.491522 | −2.0345 | 0.810083 | 1.753312 | −0.57035 |
| CA4 | −0.12376 | 0.917791 | −1.08957 | 0.725276 | 1.653217 | −0.60488 |
| CAMP | −0.21035 | 0.864327 | −1.15697 | 1.149719 | 2.218707 | −0.45071 |
| CTSG | −0.67001 | 0.628504 | −1.59108 | 0.737005 | 1.666712 | −0.59998 |
| DYNLT1 | −0.24181 | 0.845683 | −1.18248 | 0.70482 | 1.629941 | −0.61352 |
| EIF2AK2 | −0.27239 | 0.827948 | −1.20781 | 0.612933 | 1.529366 | −0.65387 |
| HMGB2 | −0.31247 | 0.805261 | −1.24183 | 0.793424 | 1.733183 | −0.57697 |
| LCN2 | −0.04099 | 0.971987 | −1.02882 | 0.668823 | 1.589775 | −0.62902 |
| LY96 | −0.09907 | 0.933638 | −1.07108 | 1.540281 | 2.908511 | −0.34382 |
| MMP9 | 0.004386 | 1.003044 | −0.99696 | 1.094061 | 2.134741 | −0.46844 |
| NUP214 | −0.83991 | 0.558679 | −1.78994 | 0.743879 | 1.674673 | −0.59713 |
| PADI4 | 0 | 1 | −1 | 0.602688 | 1.518544 | −0.65853 |
| PPBP | 0.522789 | 1.43673 | −0.69602 | 0.980735 | 1.97347 | −0.50672 |
| RETN | 0 | 1 | −1 | 0.868058 | 1.825204 | −0.54788 |
| RNASE2 | 0.647651 | 1.566616 | −0.63832 | 1.523153 | 2.874185 | −0.34792 |
| RNASE3 | 0.89758 | 1.862939 | −0.53679 | 0.814594 | 1.758803 | −0.56857 |
| S100A12 | −1.1621 | 0.446863 | −2.23782 | 0.822467 | 1.768427 | −0.56547 |
| S100A8 | −0.6609 | 0.632483 | −1.58107 | 1.789434 | 3.456793 | −0.28929 |
| S100A9 | −0.44514 | 0.734511 | −1.36145 | 1.145019 | 2.211491 | −0.45218 |
| SLC11A1 | 1.059354 | 2.083998 | −0.47985 | 0.596258 | 1.51179 | −0.66147 |
| SLPI | 0.33866 | 1.264582 | −0.79078 | 1.080609 | 2.114929 | −0.47283 |
| THBS1 | 1.252427 | 2.382419 | −0.41974 | 0.629399 | 1.54692 | −0.64645 |
| TLR5 | −0.50255 | 0.705857 | −1.41672 | 0.697811 | 1.622042 | −0.61651 |
| TNFSF10 | 0.108252 | 1.077921 | −0.92771 | 0.745898 | 1.677017 | −0.5963 |

TABLE 10

Table showing RA PBMC genes (≤−1.5 FC) in common with both SS and RA genes (1674) identified by CPA analysis and their respective FC values in three independent SS salivary gland and one RA synovial fluid data sets.

| Commonly downregulated in PBMCs of SS and RA female patients | minor SG | | | parotid gland | | | LSG | | |
|---|---|---|---|---|---|---|---|---|---|
| | logFC | FC | FC(−) | logFC | FC | FC(−) | logFC | FC | FC(−) |
| CD247 | 2.778806 | 6.862843 | −0.14571 | 1.057641 | 2.081525 | −0.48042 | 2.43E−01 | 1.183451 | −0.84489 |
| CD6 | −1.40251 | 0.378271 | −2.64361 | 0.431492 | 1.348628 | −0.74149 | −1.33E−10 | 1 | −1 |
| CD74 | 1.966877 | 3.909211 | −0.25581 | 1.193631 | 2.287277 | 0.4372 | 9.80E−09 | 1 | −1 |
| CD81 | −1.42127 | 0.373383 | −2.67822 | −0.40151 | 0.757067 | −1.32089 | 1.78E−15 | 1 | −1 |
| CD8A | 1.699666 | 3.248257 | −0.30786 | 1.665987 | 3.173308 | −0.31513 | 8.43E−01 | 1.793776 | −0.55748 |
| CD9 | 2.392951 | 5.252308 | −0.19039 | −1.20093 | 0.434995 | −2.29888 | 2.91E−01 | 1.223488 | −0.81734 |
| CXCR3 | 1.613125 | 3.059138 | −0.32689 | 0.990576 | 1.986979 | −0.50328 | 2.66E−15 | 1 | −1 |
| DNMT1 | 1.199162 | 2.296063 | −0.43553 | 0.126275 | 1.091472 | −0.91619 | 4.17E−01 | 1.335148 | −0.74898 |
| ETS1 | 1.746594 | 3.355655 | −0.298 | 1.788157 | 3.453734 | −0.28954 | 1.03 | 2.042024 | −0.48971 |
| HLA-DRB4 | 1.123421 | 2.17863 | −0.459 | 1.648651 | 3.135402 | −0.31894 | 4.67E−01 | 1.382232 | −0.72347 |
| IL2RB | 2.212902 | 4.636068 | −0.2157 | 1.756679 | 3.379194 | −0.29593 | 8.58E−01 | 1.812524 | −0.55172 |
| LEF1 | 1.912064 | 3.763471 | −0.26571 | 1.189176 | 2.280225 | 0.43855 | 1.45E−01 | 1.105731 | −0.90438 |
| PARP1 | −0.07306 | 0.950618 | −1.05195 | 0.816478 | 1.761101 | −0.56783 | 2.80E−09 | 1 | −1 |
| PSAP | −0.60125 | 0.659182 | −1.51703 | −0.56066 | 0.677993 | −1.47494 | 3.96E−01 | 1.315855 | −0.75996 |
| SNCA | −0.59877 | 0.660315 | −1.51443 | −0.73287 | 0.601707 | −1.66194 | 3.30E−01 | 1.257013 | −0.79554 |
| SRF | −0.58028 | 0.668832 | −1.49514 | −0.65992 | 0.632912 | −1.58 | 3.33E−10 | 1 | −1 |
| TNFRSF25 | 0.998359 | 1.997727 | −0.50057 | −0.27607 | 0.82584 | −1.21089 | 6.20E−09 | 1 | −1 |
| ZFP36 | −0.19988 | 0.870621 | −1.14861 | −0.77399 | 0.584799 | −1.70999 | −4.85E−01 | 0.714497 | −1.39959 |

| Commonly downregulated in PBMCs of SS and RA female patients | Sy fibroblast RA | | | PBMC(RA) | | |
|---|---|---|---|---|---|---|
| | logFC | FC | FC(−) | logFC | FC | FC(−) |
| CD247 | 0.024358 | 1.017027 | −0.98326 | −0.83718 | 0.559736 | −1.78656 |
| CD6 | 0.263473 | 1.200365 | −0.83308 | −0.66947 | 0.628738 | −1.59049 |
| CD74 | 0.843554 | 1.794465 | −0.55727 | −0.71144 | 0.610712 | −1.63743 |
| CD81 | −0.032 | 0.978066 | −1.02243 | −0.67837 | 0.624872 | −1.60033 |
| CD8A | −0.32114 | 0.800438 | −1.24932 | −0.62127 | 0.650098 | −1.53823 |
| CD9 | −0.03048 | 0.979093 | −1.02135 | −0.61644 | 0.65228 | −1.53308 |
| CXCR3 | 0.22721 | 1.170569 | −0.85429 | −0.65914 | 0.633257 | −1.57914 |
| DNMT1 | 0.120526 | 1.087131 | −0.91985 | −0.93947 | 0.521424 | −1.91783 |
| ETS1 | 0.517003 | 1.430979 | −0.69882 | −0.8879 | 0.540401 | −1.85048 |
| HLA-DRB4 | | 1 | −1 | −0.75835 | 0.591174 | −1.69155 |
| IL2RB | 0.243695 | 1.184021 | −0.84458 | −1.14397 | 0.452512 | −2.20989 |
| LEF1 | 1.222055 | 2.332788 | −0.42867 | −0.71124 | 0.610794 | −1.63721 |
| PARP1 | 0.0979 | 1.070215 | −0.93439 | −0.60657 | 0.656756 | −1.52264 |
| PSAP | 0.109239 | 1.078659 | −0.92708 | −0.5915 | 0.663654 | −1.50681 |
| SNCA | 0.575285 | 1.489971 | −0.67115 | −0.94666 | 0.518832 | −1.92741 |
| SRF | 0.242823 | 1.183306 | −0.84509 | −0.59926 | 0.660092 | −1.51494 |
| TNFRSF25 | 1.04872 | 2.068693 | −0.4834 | −0.65095 | 0.636862 | −1.5702 |
| ZFP36 | −0.74754 | 0.595619 | −1.67892 | −0.63215 | 0.645215 | −1.54987 |

TABLE 11

| | Fold change in | | | |
|---|---|---|---|---|
| Gene Symbol | MSG | PG | LSG | Mean |
| CHEK1 | 2.45 | 2.45 | 1 | 1.97 |
| CXCL10 | 15.53 | 4.66 | 4.95 | 8.38 |
| ETS1 | 3.35 | 3.45 | 2.04 | 2.95 |
| LEF1 | 3.76 | 2.28 | 1.1 | 2.38 |
| MMP9 | 11.12 | 4.76 | 1.48 | 5.79 |
| TIMP1 | −2.07 | −1.22 | −1.22 | −1.50 |
| TLR7 | 4.7 | 3.74 | 1.61 | 3.35 |

What is claimed is:

1. A method of identifying a subject as having Sjögren's syndrome (SS), or as having an increased risk of developing SS, comprising:

a) measuring a level of messenger RNA (mRNA) transcripts for the genes ETS1, LEF1, TIMP1, CHEK1, CXCL10, MMP9 and TLR7 in a saliva sample from the subject;

b) determining the DNA methylation status of the genes ETS1, LEF1, TIMP1, CHEK1, CXCL10, MMP9 and TLR7 in a saliva sample from the subject;

c) measuring the levels of long interspersed nuclear elements (LINEs) and the protein encoded by LINE1 (ORF1(p40)) in a saliva sample from the subject;

d) comparing the mRNA transcript levels of (a), the DNA methylation status of (b) and the levels of LINEs and the protein encoded by LINE1 of (c) with a level of messenger RNA (mRNA) transcripts for the genes ETS1, LEF1, TIMP1, CHEK1, CXCL10, MMP9 and TLR7 correlated with SS, DNA methylation status of the genes ETS1, LEF1, TIMP1, CHEK1, CXCL10, MMP9 and TLR7 correlated with SS and levels of LINEs and the protein encoded by LINE1 correlated with SS, wherein mRNA transcript levels, DNA methylation status and levels of LINEs and the protein encoded by LINE1 of the subject having similarity with mRNA transcript levels, DNA methylation status and levels of LINEs and the protein encoded by LINE1 correlated with SS identifies the subject as having SS or as having an increased risk of developing SS; and e) treating the subject for SS.

2. A method of identifying a subject having SS as having an increased likelihood of a poor prognosis, comprising:
   a) measuring a level of messenger RNA (mRNA) transcripts for the genes ETS1, LEF1, TIMP1, CHEK1, CXCL10, MMP9 and TLR7 in a saliva sample from the subject;
   b) determining the DNA methylation status of the genes ETS1, LEF1, TIMP1, CHEK1, CXCL10, MMP9 and TLR7 in a saliva sample from the subject;
   c) determining the levels of long interspersed nuclear elements (LINEs) and the protein encoded by LINE1 in a saliva sample from the subject;
   d) comparing the level of mRNA transcripts of (a), the DNA methylation status of (b) and the levels of LINEs and protein encoded by LINE1 of (c) with mRNA transcript levels of the genes ETS1, LEF1, TIMP1, CHEK1, CXCL10, MMP9 and TLR7 correlated with severe or advanced SS, the DNA methylation status of the genes ETS1, LEF1, TIMP1, CHEK1, CXCL10, MMP9 and TLR7 correlated with severe or advanced SS, and the levels of LINEs and the protein encoded by LINE1 correlated with severe or advanced SS,
   wherein mRNA transcript levels, DNA methylation status and levels of LINEs and the protein encoded by LINEs of the subject having similarity with the mRNA transcript levels, DNA methylation status and levels of LINEs and the protein encoded by LINE1 correlated with severe or advanced SS identifies the subject having SS as having an increased likelihood of a poor prognosis; and
   e) treating the subject for severe or advanced SS.

3. A method of monitoring a subject's response to treatment for SS, comprising:
   a) measuring a level of messenger RNA (mRNA) transcripts for the genes ETS1, LEF1, TIMP1, CHEK1, CXCL10, MMP9 and TLR7 in a saliva sample from the subject prior to treatment of the subject for SS;
   b) determining the DNA methylation status of the genes ETS1, LEF1, TIMP1, CHEK1, CXCL10, MMP9 and TLR7 in a saliva sample from the subject prior to treatment of the subject for SS;
   c) determining levels of long interspersed nuclear elements (LINEs) and protein encoded by LINE1 in a saliva sample from the subject prior to treatment of the subject for SS;
   d) initiating treatment of the subject for SS;
   e) measuring a level of messenger RNA (mRNA) transcripts for the genes ETS1, LEF1, TIMP1, CHEK1, CXCL10, MMP9 and TLR7 in a saliva sample from the subject at one or more time points after initiation of treatment of the subject for SS;
   f) determining the DNA methylation status of the genes ETS1, LEF1, TIMP1, CHEK1, CXCL10, TIMP1 and TLR7 in a saliva sample from the subject at one or more time points after initiation of treatment of the subject for SS;
   g) determining levels of long interspersed nuclear elements (LINEs) and protein encoded by LINE1 in a saliva sample from the subject at one or more time points after initiation of treatment of the subject for SS;
   h) comparing the mRNA transcript levels of (a) and (e), the DNA methylation status of (b) and (f) and the levels of LINEs and the protein encoded by LINE1 of (c) and (g), wherein mRNA transcript levels, DNA methylation status and levels of LINEs and the protein encoded by LINE1 determined after initiation of treatment for SS having less similarity with the mRNA transcript levels, DNA methylation status and levels of LINES and the protein encoded by LINE1 correlated with SS identifies the subject as having a positive response to the treatment and wherein mRNA transcript levels, DNA methylation status and levels of LINEs and the protein encoded by LINE1 determined after initiation of treatment for SS having no change or more similarity with mRNA transcript levels, DNA methylation status and levels of LINES and the protein encoded by LINE1 correlated with SS identifies the subject as having no response or a negative response to treatment; and
   i) continuing treatment and/or initiating a modified treatment and/or a different treatment for SS of the subject that has no response or a negative response to treatment and discontinuing or reducing treatment for SS of the subject that has a positive response to treatment.

4. A method of monitoring a subject's response to treatment for severe or advanced SS, comprising:
   a) measuring a level of messenger RNA (mRNA) transcripts for the genes ETS1, LEF1, TIMP1, CHEK1, CXCL10, MMP9 and TLR7 in a saliva sample from the subject prior to treatment of the subject for severe or advanced SS;
   b) determining the DNA methylation status of the genes ETS1, LEF1, TIMP1, CHEK1, CXCL10, MMP9 and TLR7 in a saliva sample from the subject prior to treatment of the subject for severe or advanced SS;
   c) determining levels of long interspersed nuclear elements (LINEs) and protein encoded by LINE1 in a saliva sample from the subject prior to treatment of the subject for severe or advanced SS;
   d) initiating treatment of the subject for severe or advanced SS;
   e) measuring a level of messenger RNA (mRNA) transcripts for the genes ETS1, LEF1, TIMP1, CHEK1, CXCL10, MMP9 and TLR7 in a saliva sample from the subject at one or more time points after initiation of treatment of the subject for severe or advanced SS;
   f) determining the DNA methylation status of the genes ETS1, LEF1, TIMP1, CHEK1, CXCL10, TIMP1 and TLR7 in a saliva sample from the subject at one or more time points after initiation of treatment of the subject for severe or advanced SS;
   g) determining levels of long interspersed nuclear elements (LINEs) and protein encoded by LINE1 in a saliva sample from the subject at one or more time points after initiation of treatment of the subject for severe or advanced SS;
   h) comparing the mRNA transcript levels of (a) and (e), the DNA methylation status of (b) and (f) and the levels of LINEs and the protein encoded by LINE1 of (c) and (g), wherein mRNA transcript levels, DNA methylation status and levels of LINEs and the protein encoded by LINE1 determined after initiation of treatment for severe or advanced SS having less similarity with the mRNA transcript levels, DNA methylation status and levels of LINES and the protein encoded by LINE1 correlated with severe or advanced SS identifies the subject as having a positive response to the treatment and wherein mRNA transcript levels, DNA methylation status and levels of LINEs and the protein encoded by LINE1 determined after initiation of treatment for severe or advanced SS having no change or more similarity with mRNA transcript levels, DNA methylation status and levels of LINES and the protein encoded by LINE1 correlated with severe or advanced SS identifies the subject as having no response or a negative response to the treatment; and i) continuing treatment and/or initiating a modified treatment and/or a different treatment for SS of the subject that has no response or a negative response to treatment and discontinuing or reducing treatment for SS of the subject that has a positive response to treatment.

* * * * *